US009913916B2

(12) United States Patent
DeSimone et al.

(10) Patent No.: US 9,913,916 B2
(45) Date of Patent: Mar. 13, 2018

(54) ASYMMETRIC BIFUNCTIONAL SILYL MONOMERS AND PARTICLES THEREOF AS PRODRUGS AND DELIVERY VEHICLES FOR PHARMACEUTICAL, CHEMICAL AND BIOLOGICAL AGENTS

(71) Applicant: The University of North Carolina at Chapel Hill, Chapel Hill, NC (US)

(72) Inventors: Joseph M. DeSimone, Chapel Hill, NC (US); Mathew Finniss, Sussex (CA); Mary Napier, Chapel Hill, NC (US); Ashish Pandya, Morrisville, NC (US); Matthew Parrott, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/283,574

(22) Filed: Oct. 3, 2016

(65) Prior Publication Data
US 2017/0021030 A1 Jan. 26, 2017

Related U.S. Application Data

(63) Continuation of application No. 14/482,624, filed on Sep. 10, 2014, now Pat. No. 9,457,098, which is a continuation of application No. 13/823,559, filed as application No. PCT/US2011/051775 on Sep. 15, 2011, now abandoned.

(60) Provisional application No. 61/383,651, filed on Sep. 16, 2010.

(51) Int. Cl.
A61K 47/48 (2006.01)
B82Y 5/00 (2011.01)
C07F 7/08 (2006.01)
C07F 7/18 (2006.01)
C07H 23/00 (2006.01)
C07K 19/00 (2006.01)
C12N 15/113 (2010.01)
A61K 47/60 (2017.01)
A61K 47/58 (2017.01)
A61K 47/61 (2017.01)
A61K 47/62 (2017.01)
A61K 47/69 (2017.01)

(52) U.S. Cl.
CPC .......... *A61K 47/4883* (2013.01); *A61K 47/58* (2017.08); *A61K 47/60* (2017.08); *A61K 47/61* (2017.08); *A61K 47/62* (2017.08); *A61K 47/6913* (2017.08); *A61K 47/6915* (2017.08); *A61K 47/6925* (2017.08); *A61K 47/6933* (2017.08); *B82Y 5/00* (2013.01); *C07F 7/083* (2013.01); *C07F 7/184* (2013.01); *C07F 7/1868* (2013.01); *C07H 23/00* (2013.01); *C07K 19/00* (2013.01); *C12N 15/113* (2013.01); *C12N 2310/14* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,904,563 | A | 2/1990 | Aoai et al. |
| 5,827,925 | A | 10/1998 | Tremont et al. |
| 6,030,959 | A | 2/2000 | Tremont et al. |
| 6,121,404 | A | 9/2000 | Liles |
| 6,413,945 | B1 | 7/2002 | Tremont et al. |
| 6,569,458 | B1 | 5/2003 | Gombotz et al. |
| 2008/0076882 | A1 | 3/2008 | Ozai |
| 2009/0317335 | A1 | 12/2009 | Lin et al. |
| 2011/0135571 | A1 | 6/2011 | Lin et al. |

FOREIGN PATENT DOCUMENTS

| | | | |
|---|---|---|---|
| CH | 569029 | | 11/1975 |
| DE | 1133133 | | 7/1962 |
| DE | 2044888 | | 3/1971 |
| EP | 0525392 | | 2/1993 |
| EP | 0754691 | | 1/1997 |
| EP | 1201672 | | 5/2002 |
| JP | 5-255348 | A | 10/1993 |
| WO | WO2009/132265 | * | 4/2009 |
| WO | WO-2009/132265 | A2 | 10/2009 |

OTHER PUBLICATIONS

"Silicon Compounds," Gelest, XP002533455, 2004, pp. 215-386.
Burkhard, C., "The Reaction of Chlorosilanes with 2-Methoxyethanol," Contribution from the Research Laboratory, General Electric Co., Jul. 13, 1949, pp. 106-107.
Chen, Yiwang, et al., "Preparation of Hollow Silica Nanospheres by Surface-Initiated Atom Transfer Radical Polymerization on Polymer Latex Templates," Advanced Functional Materials, Jan. 2005, pp. 113-117, vol. 15(1), Wiley-VCH Verlag GmbH & Co. KGaA, Weinheim.
Chung, et al., "Photopolymerization and curing shrinkage of silicon-containing multifunctional methacrylates", Journal of Materials Science Letters, 2002, pp. 1093- 1095, vol. 21.
Furusawa, et al., "New sila-analogues of cyclic nucleotides, 3', 5'-O-silanediyl nucleosides", Tetrahedron Letters, 1985, pp. 887-890, vol. 26, No. 7.
Garner, Philip et al., "Use of Silicon-Based Tethers to Control Diastereofacial Selectivity in Azomethine Ylide Cycloadditions", Journal of Organic Chemistry, Jan. 1, 1997, pp. 493-498, vol. 62.
Gratton, S., et al., "Nanofabricated particles for engineered drug therapies: A preliminary biodistribution study of PRINT™ nanoparticles", J. Control Release, Aug. 16, 2007, pp. 1-19, vol. 121 (1-2).
Kumagai, et al., "Cyclic di-t-butylsilylenediyl ether group as a convenient protective group for the glycoconjugate synthesis", Tetrahedron Letters, 2001, pp. 1953-1956, vol. 42.

(Continued)

Primary Examiner — Jeanette Lieb
(74) Attorney, Agent, or Firm — Alston & Bird LLP

(57) ABSTRACT

Asymmetric bifunctional silyl (ABS) monomers comprising covalently linked pharmaceutical, chemical and biological agents are described. These agents can also be covalently bound via the silyl group to delivery vehicles for delivering the agents to desired targets or areas. Also described are delivery vehicles which contain ABS monomers comprising covalently linked agents and to vehicles that are covalently linked to the ABS monomers. The silyl modifications described herein can modify properties of the agents and vehicles, thereby providing desired solubility, stability, hydrophobicity and targeting.

15 Claims, 14 Drawing Sheets

(56) References Cited

OTHER PUBLICATIONS

Mahkam, M. et al., "PH-sensitive hydrogel containing Acetaminophen silyl ethers for colon-specific drug delivery", *Designed Monomers and Polymers, VSP*, Utrecht, NL, Nov. 1, 2006, pp. 607-615, vol. 9, No. 6.

Parrott, Matthew C., et al., "Tunable Bifunctional Silyl Ether Cross-Linkers for the Design of Acid-Sensitive Biomaterials", *Journal of the American Chemical Society*, Nov. 24, 2010, pp. 17928-17932, vol. 132, No. 50.

Perkins, W.E., et al.., "Polymer Delivery of the Active Isomer of Misoprostol: A Solution to the Intestinal Side Effect Problem," *The Journal of Pharmacology and Experimental Therapeutics*, Dec. 13, 1993, pp. 151-156, vol. 269(1), The American Society for Pharmacology and Experimental Therapeutics.

Shea, K.J. et al., "Pericyclic Umpolung. Reversal of Regioselectivity in the Diels-Alder Reaction", *Tetrahedron Letters*, 1991, pp. 2715-2718, vol. 32, No. 24.

Themistou, E., et al., "Synthesis and Characterization of Star Polymers and Cross-Linked Star Polymer Model Networks Containing a Novel, Silicon-Based, Hydrolyzable Cross-Linker," *Macromolecules*, 2004, pp. 6734-6743, vol. 37.

Tremont, S.J. et al., "Catalytic Functionalization of Polymers: A Novel Approach to Site Specific Delivery of Misoprostol to the Stomach", *Journal of Medicinal Chemistry*, Jan. 1, 1993, pp. 3087-3097, vol. 36, No. 21, American Chemical Society, US.

Trost, et al., "The di-t-butylsilylene protecting group for diols", *Tetrahedron Letters*, 1981, pp. 4999-5002, vol. 22, No. 50.

\* cited by examiner

DRUGS AMENABLE TO SILYL ETHER PRODRUG SYSTEM

CHRONIC PAIN
HYDROMORPHONE, OXYCODONE, CODEIN, TRAMADO, LORAZEPAM, METHACARDANOL, DIFLINISOL, PIROZICAM, MORPHONE, OXYMORPHONE

ASTHMA
BAMBUTEROL, MONTELUKAST, CICLESONIDE, MOMETRASONE, ALBUTEROL, TERBUTALINE, LEVAIBUTEROL, METAPROTENENOL, ISOPROTERENO, AIMETEROL, FORMOTEROL, CROMOLYN, PLUTICASONE, BUDENOSIDE

ISCHEMIC HEART DISEASE
PROPANOLOI, METROPROLO, ATENOLOL, SOTALOL, PINDOLOL, ACEBUTOLOL, CARVEDILOL, RANOTAZINE, LABETOLOL, NAPOLOL, CHLORTHAIDONE, LOSARTAN, ATERNOLOL, METOPROLOL

PSYCHOSIS
FLUPHENAZINE, PERPHERAZINE, HALOPERIDOL, QUETIAPINE, PALIPERIDONE

DEPRESSION
VENLAFAXINE, DESUENIAFAXINE

HYPERTENSION
CHLORTHAIDONE, LOSARTAN, ATERNOLOL, METOPROLOL

COPD
IPRATROPIUM, TIOTROPIUM, ALBUTEROL, LEVALBUTEROL, PIRBUBEROL, SALMETEROL, FORMOTEROL, ARFORMOTEROL, FLUTICASONE

PARKINSON'S DISEASE
BROMOCRIPTINE, LEVODOPA, ROTIGOTINE, APOMORPHINE

HIV
RITONAVIE, DARUNAVIE, ATAZANAVIE, EMTRICITABINE, ABACAVIT, LAMIVUDINE, RAITRGRAVIR

CANCER
IRINOTECAN, GEMCITABINE, VINORELBINE, 5-FU, ETOPOSIDE, TENIPOSIDE, TOPOTECAN, PACLITAXEL, VINCRASTINE

DEMENTIA
GALANTAMINE

DIARRHEA
METRONIDAZOLE

*FIG. 8*

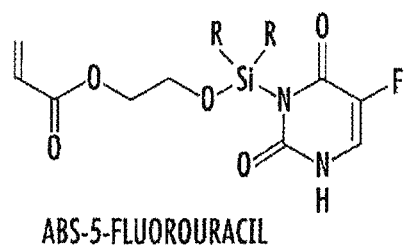
ABS-5-FLUOROURACIL
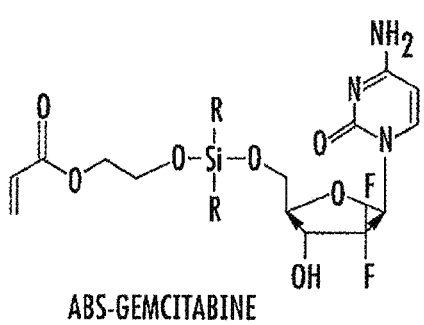
ABS-GEMCITABINE
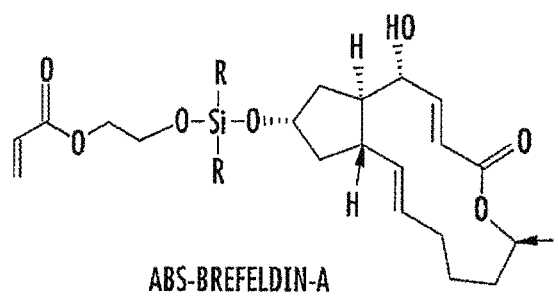
ABS-BREFELDIN-A
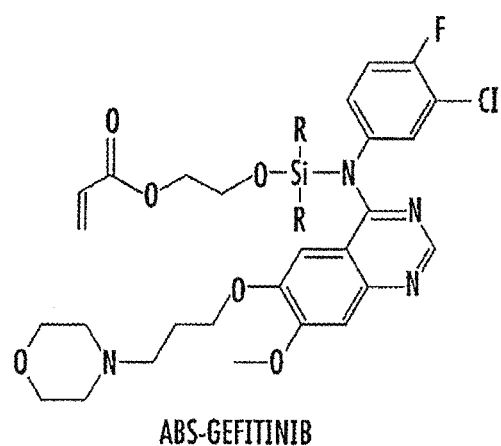
ABS-GEFITINIB
FIG. 10

ASYMMETRIC BIFUNCTIONAL SILYL MONOMERS AND PARTICLES THEREOF AS PRODRUGS AND DELIVERY VEHICLES FOR PHARMACEUTICAL, CHEMICAL AND BIOLOGICAL AGENTS

CROSS REFERENCE TO RELATED APPLICATIONS

This application is a continuation of U.S. application Ser. No. 14/482,624, filed Sep. 10, 2014, which is a continuation of U.S. National Stage application Ser. No. 13/523,559, filed Apr. 29, 2013, which is based on International Patent Application No. PCT/US2011/051775, filed Sep. 15, 2011, which claims the benefit of U.S. Provisional Application No. 61/383,651, filed Sep. 16, 2010, all of which are herein incorporated by reference in their entirety.

GOVERNMENT SUPPORT

This invention was made with government support under Grants 1-DP1-OD006432-01, CA119343 and CA151652 awarded by the National Institutes of Health. The government has certain rights in the invention.

FIELD OF THE INVENTION

The subject matter herein is directed to asymmetric bifunctional silyl (ABS) monomers, such as silyl ether containing pharmaceutical, chemical and biological agents and delivery vehicles for these agents as well as ABS modified delivery vehicles themselves, such as liposomes and nanoparticles.

BACKGROUND

Drug delivery technology has been exploited extensively for the purpose of delivering agents to desired targets for many years. Drug delivery technologies involve liposomes and nano or microparticles. Hydrophobic or hydrophilic compounds can be entrapped in the hydrophobic domain or encapsulated in the aqueous compartment, respectively. Liposomes can be constructed of natural constituents so that the liposome membrane is in principal identical to the lipid portion of natural cell membranes. It is considered that liposomes are quite compatible with the human body when used as drug delivery systems.

The cellular delivery of various therapeutic compounds, such as chemotherapeutic agents, is usually compromised by two limitations. First, the selectivity of a number of therapeutic agents is often low, resulting in high toxicity to normal tissues. Secondly, the trafficking of many compounds into living cells is highly restricted by the complex membrane systems of the cell. Specific transporters allow the selective entry of nutrients or regulatory molecules, while excluding most exogenous molecules such as nucleic acids and proteins.

The problems mentioned above are not adequately addressed by existing delivery vehicles or compositions. The presently disclosed subject matter addresses, in whole or in part, these and other needs in the art.

SUMMARY OF THE INVENTION

Asymmetric bifunctional silyl (ABS) monomers containing pharmaceutical, chemical and biological agents are described. These agents can be covalently bound via the Si atom, for example with a silyl ether linkage. The monomers themselves can be covalently bound via the Si atom to delivery vehicles, such as particles, for delivering the agents to desired targets or areas. Also described are delivery vehicles which contain an agent having a silyl ether linkage and to vehicles that are covalently linked to the silyl ether agent. The (ABS) modified agents described herein provide modified properties of the agents and vehicles, thereby providing desired solubility, stability, hydrophobicity and targeting.

BRIEF DESCRIPTION OF THE FIGURES

FIGS. 8-11 depict drugs and compounds that, in some embodiments, can be covalently bound to form ABS monomers and particle thereof.

DETAILED DESCRIPTION

Figure 1:
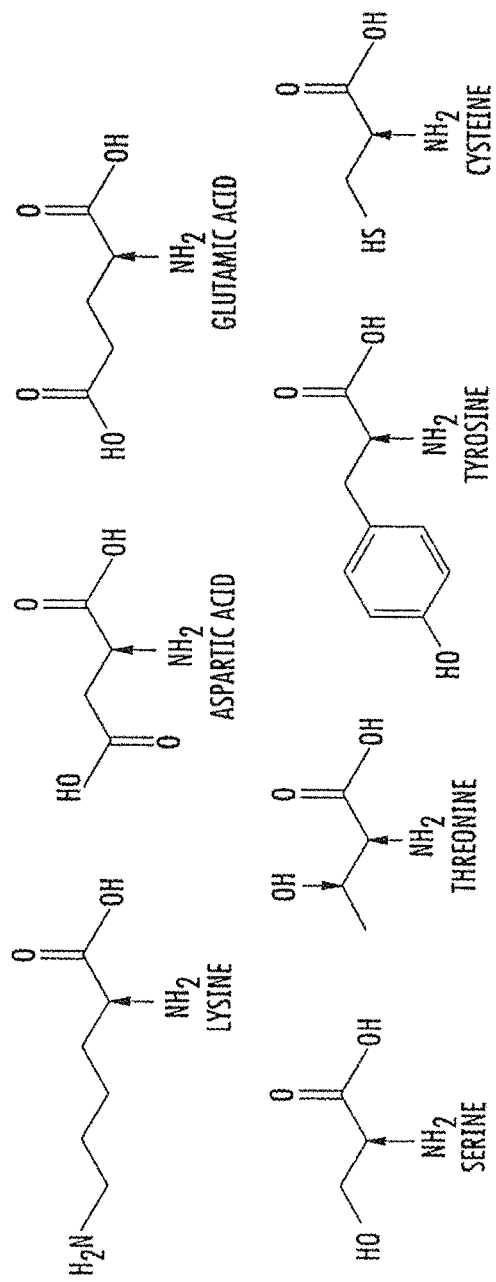
FIG. 1 depicts a representative group of amino acids that provide sites for silyl attachment.
Figure 2:
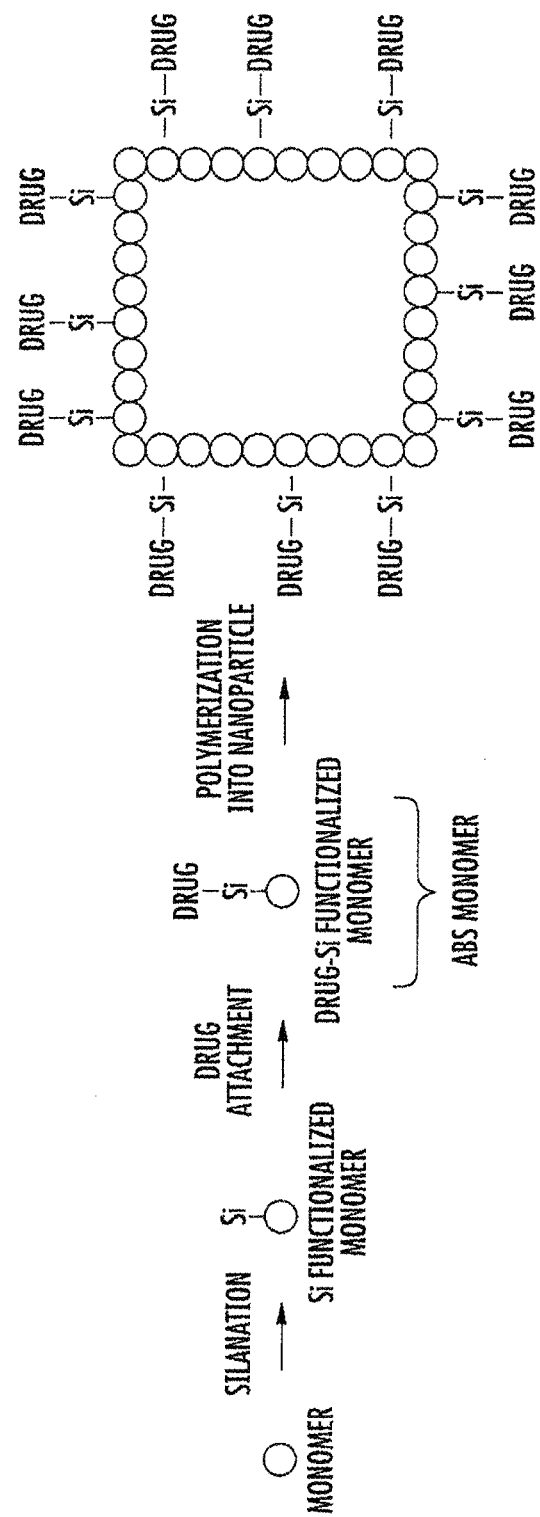
FIG. 2 depicts the preparation of asymmetric bifunctional silyl (ABS) monomers and their incorporation into a polymer particle. In each instance, the monomer residue and the drug residue may be the same or different from other ABS monomers within the polymer particle.
Figure 3A:
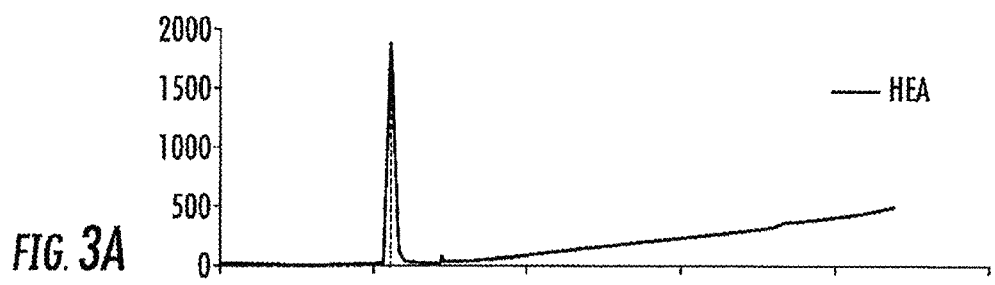
FIGS. 3A-D depict high performance liquid chromatograms of HEA, camptothecin, Et-CPT ABS prodrug, and the pro-drug after exposure to acid.
Figure 3B:
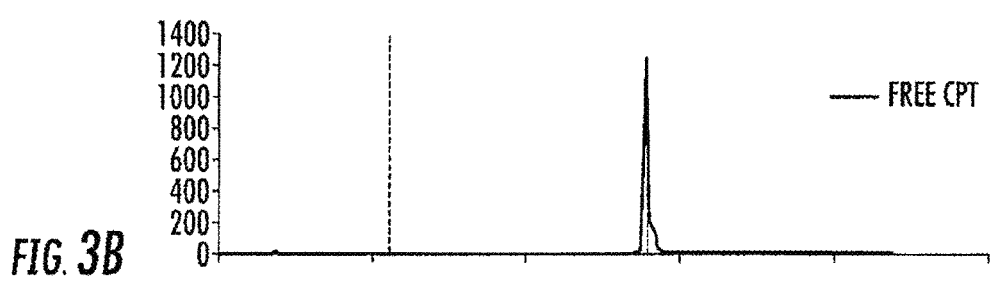
Figure 3C:
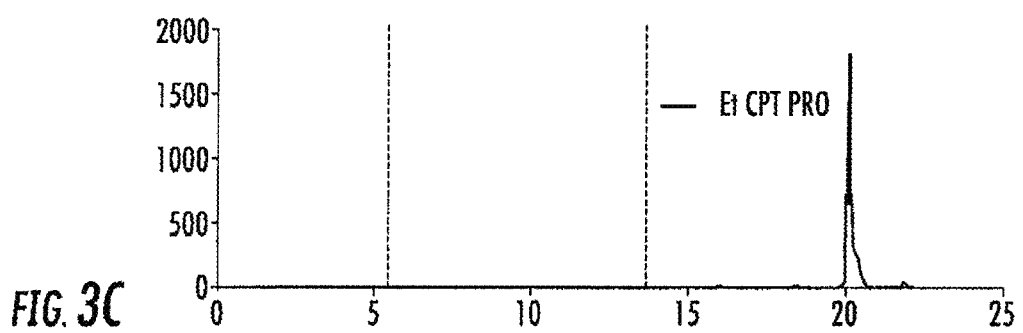
Figure 3D:
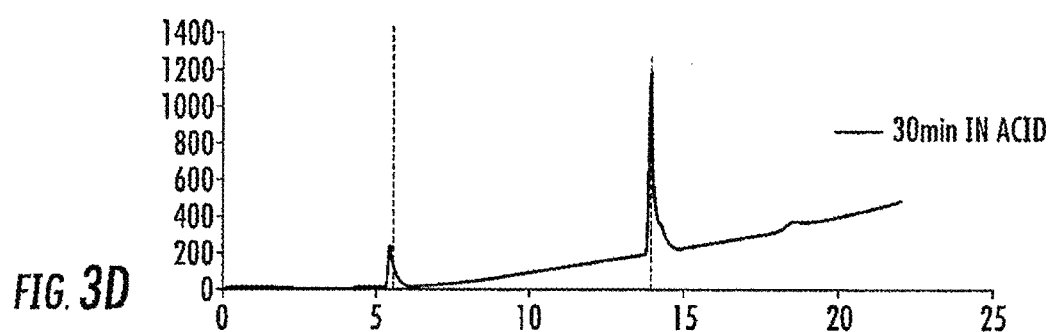

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

The tailorable ABS pro-drugs, monomers and particles described herein provide effective modifications of a parent drug, particle, such as molded particles to prepare compositons for targeted delivery of a drug or cargo. Advantages of the presently disclosed ABS compositions include: one-pot synthesis of ABS pro-drugs, monomers and particles; tunable release kinetics; wide ranges of biocompatibility; release of parent drug; stability under physiological conditions up to the desired target; higher drug loading over conventional silyl linked drugs; and targeted degradation under certain acidic conditions.

Disclosed herein are agents and delivery vehicles that have desirable properties. These properties are provided by covalently linking a silyl moiety to the agent or vehicle or both via covalent bond(s).

In embodiments, the present subject matter is directed to a functionalized drug delivery monomer comprising an asymmetric bifunctional silyl (ABS) prodrug having a formula.

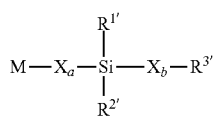

Ia wherein $R^{1'}$ and $R^{2'}$ are independently selected from the group consisting of alkyl, cycloalkyl, alkenyl, alkynyl, aryl, aralkyl, alkaryl, and a hydrophobic group, preferably $R^{1'}$ and $R^{2'}$ are independently selected from a $C_{1-4}$ alkyl;

wherein M is a residue of one of the following selected from the group consisting of a hydrogel, 2-Hydroxyethyl acrylate, 2-Hydroxyethyl methacrylate, vinyl pyrrolidone, acrylic acid, ethylene oxide or Poly(ethylene oxide) monomers, vinyl alcohol, a protein, an amino acid, and a polysaccharide;

wherein $X_a$ and $X_b$ are each independently selected from the group consisting of O, NH, S, and a carboxyl (COO); and wherein $R^{3'}$ is selected from the group consisting of a drug, a biologic, or fragments thereof.

In preferred monomers, at least one of $X_a$ and $X_b$ is O. More preferably, $X_a$ and $X_b$ are each O.

The ABS monomers described herein can advantageously be employed to prepare polymers containing any number of different ABS monomer units, wherein each monomer's components, i.e., specific values for the M, X and R' variables, can be independently selected from any other monomer's components. For example, an ABS monomer's component M can be selected from $M_1$, $M_1$, $M_3$, $M_4$ and so on. A second ABS monomer's component M can be the same or different from the first monomer's M component. Likewise, X and R' variables can be independently selected for each monomer. The advantageous result is highly tunable monomer units. These units, in turn, can be used to prepare uniquely tunable polymers by selecting the desired monomers to form the polymer. This is a superior method of preparing polymers because it yields a polymer containing not only different cargos, e.g. drugs, but the polymer can also exhibit different release rates for each cargo. Moreover, the amounts of cargo that can be incorporated into the polymer are substantially higher using the present method up to about 50 wt. %.

In embodiments, the present subject matter is directed to one or more molded polymer particles comprising ABS pro-drugs and/or ABS-monomers. Advantageously, the particles can comprise different ABS monomers and the corresponding covalently attached drug/cargo. As described herein, the monomers are tunable. In turn, preparing the present particles from the ABS monomers provides methods for incorporating many types of monomers and cargos in a single particle. Consequently, the particles themselves are highly tunable and novel. Indeed, the load of cargo measured by a ratio or wt. % of the present particles is superior. The present particles comprise a crosslinked network of the ABS monomers. Methods of preparing particles are described in US 2009/0028910; US 2009/0061152; WO 2007/024323; US 2009/0220789; US 2007/0264481; US 2010/0028994; US 2010/0196277; WO 2008/106503; US 2010/0151031; WO 2008/100304; WO 2009/041652; PCT/US2010/041797; US 2008/0181958; WO 2009/111588; and WO 2009/132206, each of which is hereby incorporated by reference in their entirety.

Preferably, the particles contain a cargo, such as an ABS pro-drug, which comprises a ratio of about 0.1 mg of drug to about 1 mg of particle. Also preferred are particles wherein the cargo, such as an ABS pro-drug, comprises from about 1 wt. % to about 50 wt. % of the particle; from about 1 wt. % to about 40 wt. % of the particle; from about 2 wt. % to about 20 wt. % of the particle; from about 3 wt. % to about 50 wt. %; from about 4 wt. % to about 50 wt. % of the particle; from about 5 wt. % to about 50 wt. % of the particle; from about 5 wt. % to about 25 wt. % of the particle; from about 5 wt. % to about 20 wt. %; and from about 5 wt. % to about 15 wt. % of the particle.

The particles are preferably molded wherein the molded particle further comprises a three-dimensional shape substantially mimicking the mold shape and a size less than about 50 micrometers in a broadest dimension. In further embodiments, the particles are preferably molded to have a three-dimensional shape substantially mimicking the mold shape and a size less than about 5 micrometers in a broadest dimension. Preferably, the molded particles have a first dimension of less than about 200 nanometers and a second dimension greater than about 200 nanometers.

In an embodiment, a molded particle comprises, two or more asymmetric bifunctional silyl pro-drug monomers having a formula

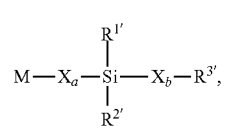

Ia wherein, in each monomer, $R^{1'}$ and $R^{2'}$, in each instance, are independently selected from the group consisting of alkyl, cycloalkyl, alkenyl, alkynyl, aryl, aralkyl, alkaryl, and a hydrophobic group, preferably both $R^{1'}$ and $R^{2'}$ are independently selected from a $C_{1-4}$ alkyl, wherein, in each monomer, M is a residue of one of the following selected from the group consisting of a hydrogel, 2-Hydroxyethyl acrylate, 2-Hydroxyethyl methacrylate, vinyl pyrrolidone, acrylic acid, ethylene oxide or Poly (ethylene oxide) monomers, vinyl alcohol, a protein, an amino acid, and a polysaccharide;

wherein, in each monomer, $X_a$ and $X_b$, in each instance, are each independently selected from the group consisting of O, NH, S, and a carboxyl; and wherein, in each monomer, $R^{3'}$ in each instance, is selected from the group consisting of a drug, a biologic, or fragments thereof, wherein in each monomer, the variables M and drug can be independently selected from each other monomer.

In another embodiment, the present subject matter is directed to a molded particle comprising, a first asymmetric bifunctional silyl pro-drug monomer having the structure

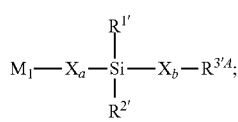
Ib and a second asymmetric bifunctional silyl pro-drug monomer having the structure

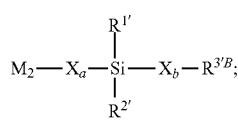
Ic wherein, in each monomer, $R^{1'}$ and $R^{2'}$, in each instance, are independently selected from the group consisting of alkyl, cycloalkyl, alkenyl, alkynyl, aryl, aralkyl, alkaryl, and a hydrophobic group, preferably both $R^{1'}$ and $R^{2'}$ are independently selected from a $C_{1-4}$ alkyl;

wherein, in each monomer, $M_1$ or $M_2$ is a residue of one of the following selected from the group consisting of a hydrogel, 2-Hydroxyethyl acrylate, 2-Hydroxyethyl methacrylate, vinyl pyrrolidone, acrylic acid, ethylene oxide or Poly(ethylene oxide) monomers, vinyl alcohol, a protein, an amino acid, and a polysaccharide;

wherein, in each monomer, $X_a$ and $X_b$, in each instance, are each independently selected from the group consisting of O, NH, S, and a carboxyl; and wherein, in each monomer, $R^{3'A}$ or $R^{3'B}$, in each instance, is selected from the group consisting of a drug, a biologic, or fragments thereof, wherein,
i. $M_1$ and $M_2$ are different,
ii. $R^{3'A}$ and $R^{3'B}$ are different,
iii. $M_1$ and M2 are the same, and $R^{3'A}$ and $R^{3'B}$ are different,
or
iv. $M_1$ and M2 are different, and $R^{3'A}$ and $R^{3'B}$ are the same.

In another aspect of this embodiment, the molded particle can further comprise a third asymmetric bifunctional silyl pro-drug monomer having the structure

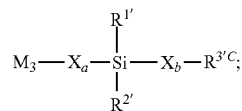
Id wherein, in each monomer, $R^{1'}$ and $R^{2'}$, in each instance, are independently selected from the group consisting of alkyl, cycloalkyl, alkenyl, alkynyl, aryl, aralkyl, alkaryl, and a hydrophobic group, preferably both $R^{1'}$ and $R^{2'}$ are independently selected from a $C_{1-4}$ alkyl;

wherein, in each monomer, M3 is a residue of one of the following selected from the group consisting of a hydrogel, 2-Hydroxyethyl acrylate, 2-Hydroxyethyl methacrylate, vinyl pyrrolidone, acrylic acid, ethylene oxide or Poly(ethylene oxide) monomers, vinyl alcohol, a protein, an amino acid, and a polysaccharide;

wherein, in each monomer, $X_a$ and $X_b$, in each instance, are each independently selected from the group consisting of O, NH, S, and a carboxyl; and wherein, in each monomer, $R^{3'C}$, in each instance, is selected from the group consisting of a drug, a biologic, or fragments thereof, wherein,
i. $M_1$ and M2 are different than M3,
or
ii. $R^{3'A}$ and $R^{3'B}$ are different than $R^{3'C}$.

The present particle can contain a fourth, fifth, sixth and so on asymmetric bifunctional silyl pro-drug monomer. Each monomer can be individualized by selecting desried values for each variable M, X and R'. Accordingly, the polymers/particles prepared from these monomers can include any number of cargos/drugs and, of course, are tunable themselves given the tenability of the monomers components.

A feature of the present particles is their release rates. In a preferred embodiment, $R^{1'}$ and $R^{2'}$ of the ABS monomer are each ethyl and the polymer particle formed therefrom has a release rate of 2.87 at pH 7.4 relative to a release rate at pH 5.0 of a particle having $R^{1'}$ and $R^{2'}$ of ethyl. In another preferred embodiment, wherein $R^1$ and $R^2$ are isopropyl, the particle has a release rate of 50.4 at pH 5.0 and 201 at pH 7.4 relative to a release rate at pH 5.0 of a particle having $R^{1'}$ and $R^{2'}$ of ethyl. In another preferred embodiment wherein $R^{1'}$ and $R^{2'}$ are t-butyl, the particle has a release rate of 4968 at pH 5.0 and 9675 at pH 7.4 relative to a release rate at pH 5.0 of a particle having $R^{1'}$ and $R^{2'}$ of ethyl.

In an embodiment, the present subject matter is directed to a composition comprising a plurality of substantially identically sized and shaped molded particles as described herein.

In embodiments, the present subject matter is directed to methods of preparing an ABS pro-drug or ABS monomer, the methods comprising, covalently linking a monomer and a silyl via an O, N, S or carboxyl of said monomer to prepare a silyl monomer;

covalently linking a drug to said silyl monomer to prepare a drug-silyl monomer;

cross-linking at least one of said drug-silyl monomers to another said drug-silyl monomer, to form a polymer wherein the monomer and/or the drug can be different in each drug-silyl monomer, wherein each of said covalent linkages is reversible. Preferably, the monomer is degradable.

Preferably, the covalent linking of the monomer with the silyl is via a carbon-oxygen bond.

In another embodiment, the present subject matter is directed to a method for reversibly modifying a characteristic of a particle comprising,
  i. reversibly bonding a silyl group with a particle through a covalent bond, wherein said particle comprises a drug; and
  ii. reversibly bonding to said silyl group a lipid or polymer through a covalent bond;
wherein the lipid or polymer modifies a characteristic of said particle, wherein i. and ii. can be performed in any order. The method can further comprise reversing the covalent bonds in any manner thereby releasing the parent cargo/drug or lipid or polymer. The covalent bonds are selected from Si—O; Si—N; Si—S or Si—COO.

Useful chracteristics of a particle that can be modified include the hydrophobic or hydrophilic characteristic of the particle. Known lipids and polymers in the art can be used via the chemical handles on the particles and the lipid or polymer itself by the methods described herein as well as the information incorporated by reference.

In some embodiments of the present invention, reversible silyl ether, silyl ester, silyl amine or silyl thio ether moieties are attached to the surface of a particle to attach i) lipids, ii) water soluble polymers (e.g. poly(ethylene glycol)), and iii) reversible silyl ether, ester, amine or thio ether pro-drugs with the particle and iv) targeting ligands. Additionally, reversible silyl ether, ester, amine or thio ether chemistry is used to iv) introduce silyl ether, ester, amine or thio ether pro-drugs to the interior of a nanoparticle. According to such embodiments, the particle can facilitate delivery of a cargo, such as a drug for example, in vivo safely and securely until a give a biological or chemical condition is reached which triggers reversing of the link chemistry and therefore release of the cargo.

In embodiments, the present subject matter is directed to methods of reversibly modifying a characteristic of an agent comprising,
  i. reversibly bonding a silyl group with an agent through a covalent bond; and
  ii. reversibly bonding to the silyl group a lipid or polymer through a covalent bond;
wherein the lipid or polymer modifies a characteristic of said particle, wherein i. and ii. can be performed in any order. The method can further comprise reversing the covalent bonds in any manner thereby releasing the parent agent or lipid or polymer. The covalent bonds are selected from Si—O; Si—N; Si—S or Si—COO.

Useful chracteristics of an agent that can be modified include the hydrophobic or hydrophilic characteristic of the agent. Known lipids and polymers in the art can be used via the chemical handles on the agent and the lipid or polymer itself by the methods described herein as well as the information incorporated by reference. The term "active", "active agent", "active pharmaceutical agent", "active drug" or "drug" as used herein means any active pharmaceutical ingredient ("API"), including its pharmaceutically acceptable salts (e.g. the hydrochloride salts, the hydrobromide salts, the hydroiodide salts, and the saccharinate salts), as well as in the anhydrous, hydrated, and solvated forms, in the form of prodrugs, and in the individually optically active enantiomers of the API as well as polymorphs of the API.

As used herein the term "mammal" refers to humans as well as all other mammalian animals. As used herein, the term "mammal" includes a "subject" or "patient" and refers to a warm blooded animal.

As used herein, the terms "cancer" and "cancerous" refer to or describe the physiological condition in mammals that is typically characterized by unregulated cell growth. Examples of cancer include, but are not limited to, melanoma, carcinoma, lymphoma, blastoma, sarcoma, and leukemia or lymphoid malignancies. More particular examples of cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

As used herein, the term "therapeutically effective" and "effective amount," is defined as the amount of the pharmaceutical composition that produces at least some effect in treating a disease or a condition. For example, in a combination according to the invention, an effective amount is the amount required to inhibit the growth of cells of a neoplasm in vivo. The effective amount of active compound(s) used to practice the present invention for therapeutic treatment of neoplasms (e.g., cancer) varies depending upon the manner of administration, the age, body weight, and general health of the subject. It is within the skill in the art for an attending physician or veterinarian to determine the appropriate amount and dosage regimen. Such amounts may be referred to as "effective" amounts.

An "active agent moiety" in reference to a prodrug conjugate of the invention, refers to the portion or residue of the umodified parent active agent up to the covalent linkage resulting from covalent attachment of the drug (or an activated or chemically modified form thereof) to a polymer of the invention. Upon hydrolysis of the linkage between the active agent moiety and the multi-armed polymer, the active agent per se is released.

As used herein, the term "ligand" refers to a molecule that can be used to target a desired area or tissue. The ligand will have an affinity for the desired tissue based on intrinsic properties of the ligand and the target.

As used herein, "wt. %" can be determined by the weight of the silyl pro-drug moeity covalently bound to the particle relative to the weight of the particle or the weight of particular ABS monomers incorporated into the polymer relative to the weight of the polymer particle.

As used herein, the term "substantially mimicking" means a molded particle that has a shape that is predetermined from the mold used to prepare the particle. This term includes variance in the shape, size, volume, etc. of the particle from the mold itself. However, the particles shape, size, volume etc. cannot be random since they are prepared from molds and substantially mimic the mold's shape, size, volume, etc.

As used herein, the term "residue" refers to the parent drug, monomer or particle wherein an O, N, S or carboxyl moiety on the parent is covalently bound to a Si atom in the ABS molecule. Upon cleavage of the reversible Si bond and the residue, the parent drug, monomer or particle is released.

As used herein, the term "alkyl" refers to both straight, branched carbon chains and cyclic hydrocarbon groups; references to individual alkyl groups are specific for the straight chain (e.g. butyl=n-butyl). In one embodiment of alkyl, the number of carbons atoms is 1-20, in other embodiments of alkyl, the number of carbon atoms is 1-12, 1-10 or 1-8 carbon atoms. In yet another embodiment of alkyl, the number of carbon atoms is 1-4 carbon atoms. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyls, are referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The term "alkenyl" refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in other embodiments of alkenyl, the number of carbon atoms is 2-12, 2-10 or 2-8. In yet another embodiment of alkenyl, the number of carbon atoms is 2-4. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "alkynyl" refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in other embodiments of alkynyl, the number of carbon atoms is 2-12, 2-10 or 2-8. In yet another embodiment of alkynyl, the number of carbon atoms is 2-4. The term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "aryl" refers to a $C_6$-$C_{14}$ aromatic carbocyclic ring structure having a single ring or multiple fused rings. Aryl groups include, but are not limited to, phenyl, biphenyl, and naphthyl. In some embodiments aryl includes tetrahydronapthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)-amino, di(alkynyl) amino, or $SF_5$. In one embodiment of aryl, the moiety is phenyl, naphthyl, tetrahydronapthyl, phenylcyclopropyl and indanyl; in another embodiment of aryl, the moiety is phenyl. The term "alkaryl" refers to an alkyl substituted aryl.

The term "aralkyl" refers to an alkyl where at least one hydrogen is substituted with an aryl group. Examples include phenyl $C_{1-4}$ alkyl and benzyl.

As used herein, a silyl ether, ester, amine or thio ether has the general structure:

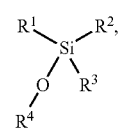

wherein $R^1$, $R^2$, $R^3$ and $R^4$ are independently hydrogen, alkyl or a pharmaceutical, chemical or biological agent, wherein at least one of $R^1$, $R^2$, $R^3$ and $R^4$ represents a pharmaceutical, chemical or biological agent and $R^4$ represents a lipid, a tracer, a ligand, a particle as described herein, a polymer, a monomer or a drug delivery vehicle. In another embodiment, when $R^4$ represents a drug delivery vehicle, $R^1$ is a pharmaceutical, chemical or biological agent, a lipid, a tracer or a ligand and $R^1$ and $R^2$ are independently hydrogen or alkyl.

As used herein, a silyl ether, ester, amine or thio ether can also have the general structure:

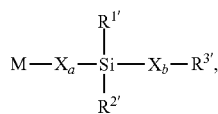

Ia wherein M, $X_a$, $X_b$, $R^{1'}$, $R^{2'}$ and $R^{3'}$ are as described herein.

According to the present invention, generally any nucleophilic particle will facilitate a silyl ether linkage. "Nucleophile" refers to an ion or atom or collection of atoms that may be ionic, having a nucleophilic center, i.e., a center that is seeking an electrophilic center, and capable of reacting with an electrophile. "Electrophile" refers to an ion, atom, or collection of atoms that may be ionic, having an electrophilic center, i.e., a center that is electron seeking, capable of reacting with a nucleophile. Specifically, particles comprised of poly(alcohols), poly(amines), poly(carboxylates), and poly(thiols), and the like will facilitate a silyl ether linkage. Compositions including sugars (e.g. lactose, glucose,) polysaccharides (e.g. dextran, cyclodextran), glycerol, poly(ethylene glycol), poly(vinyl alcohol), poly(amino ethyl methacrylate), poly(aminopropyl methacrylate), poly(carboxyethyl acrylate) are ideal for this chemistry. In a particular embodiment, a particle composition can include 40 wt % human serum albumin, 40 wt % lactose and 20 wt % glycerol.

In one embodiment, a pharmaceutical, chemical or biological agent is covalently linked to a silyl ether, ester, amine or thio ether moeity. In this embodiment, the resulting compound can act as a pro-drug of the agent. Thus, in structure I above, the residue of an agent can be $R^1$, $R^2$ or $R^3$, wherein an atom on the agent is bound to the silicon atom. The atom or moiety contained in the structure of the agent is generally an O, N, S or carboxyl, thereby forming a silyl ether, ester, amine or thio ether bond. The remaining R groups can be unsubstituted or substituted with the variables described above. Methods of preparing such silyl ether, ester, amine or thio ether compounds, also referred to as ABS pro-drugs or ABS monomers, are described herein.

Additional specific embodiments of the present disclosure include: A delivery vehicle for pharmaceutical, chemical or biological agents, said vehicle comprising a silyl ether. Preferably in this delivery vehicle, the silyl ether is present on an exterior or interior surface of said vehicle. Also preferred in this delivery vehicle, the silyl ether is covalently linked to the exterior or interior surface. Preferably, the silyl ether comprises a lipid, polymer, ligand, tracer, chemical agent, pharmaceutical agent or biological agent. Preferably, the polymer is a water soluble polymer. More preferably, the polymer is a PEG, PLGA, PMMA, or other biocompatible, biodegradable, or the like polymer. Useful delivery vehicles are selected from the group consisting of a liposome, particle, microparticle and nanoparticle. Most preferably, the vehicle is a molded micro- or nanoparticle.

Another embodiment is directed to a compound having a silyl ether covalent linkage bound to a pharmaceutical, chemical or biological agent. In this embodiment, the silyl ether covalent linkage is bound to a pharmaceutical agent. Preferably, the pharmaceutical agent is selected from the group consisting of analgesics, anti-cancer agents, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids, and mixtures thereof. More preferably, the pharmaceutical agent is an anti-cancer agent. It is also preferred that the pharmaceutical or biological agent is selected from quinoline alkaloids, taxanes, anthracyclines, nucleosides, kinase inhibitors, tyrosine kinase inhibitors, antifolates, proteins and nucleic acids. More preferably, the pharmaceutical or biological agent is selected from the group consisting of Camptothecin, Topotecan, Irinotecan, SN-38, Paclitaxel, Docetaxel, Daunorubicin, Doxorubicin, Epirubicin, Idarubicin Gemcitabine, Cytarabine, Brefeldin-A Imatinib, Gefitinib, Lapatinib, Sunitinib, Methotrexate, Folinic Acid, Efflux Inhibitors, ATP-Binding Inhibitors, Cytochrome-C, Ovalbumin, siRNA Anti-Luciferase, siRNA Androgen Receptor and RNA Replicon. Also preferred are compounds where the silyl ether covalent linkage is bound to a biological agent. These biological agents are preferably DNA, RNA, siRNA, cDNA, proteins or immunoglobulins. Also preferred are compounds where the silyl ether covalent linkage is bound to a chemical agent. Useful chemical agents include a pesticide, fungicide, insecticide, herbicide or biocide. The silicon atom of the silyl ether can further be covalently bound to a lipid, polymer, ligand or tracer.

In another embodiment, the present subject matter is directed to a method of treating a mammal, comprising administering a delivery vehicle as disclosed herein, wherein the compound comprises a pharmaceutical or biological agent.

In another embodiment, the present subject matter is directed to a method of modifying a property of an agent, comprising preparing a silyl ether covalently linked to the agent, wherein the agent is a pharmaceutical, chemical or biological agent. In a preferred aspect of this embodiment, the silicon atom of the silyl ether is further covalently bound to a lipid, polymer, ligand or tracer. Preferably, the property modified by the present method is solubility in an aqueous milieu Another preferred property modified by the present method is is stability. Yet, another preferred property modified by the present method is is hydrophobicity.

In another embodiment, the present subject matter is directed to a method of preparing a silyl ether compound, comprising contacting a nucleophile with a silane, wherein a silyl ether compound is prepared. In this method, it is preferred that the nucleophile is selected from the group consisting of hydroxyl, amine, carboxyl and thiol. Preferably, the nucleophile is covalently linked to a pharmaceutical, chemical or biological agent.

Preferred pharmaceutical agents include silyl ethers, esters, amines and thio ethers connected to, but not limited to, Camptothecin, Topotecan, Irinotecan, SN-38, Paclitaxel, Docetaxel Daunorubicin, Doxorubicin, Epirubicin, Idarubicin Gemcitabine, Cytarabine Brefeldin-A Imatinib, Gefitinib, Lapatinib, Sunitinib Methotrexate, Folinic Acid Efflux Inhibitors, ATP-Binding Inhibitors Cytochrome-C, Ovalbumin siRNA Anti-Luciferase, siRNA Androgen Receptor, and RNA Replicon. Other agents include Busulfan, Chlorambucil, Cyclophosphamide, melphalan, Carmustine, Lomustine, Cladribine, Cytarabine (Cytosine Arabinoside), Floxuridine (FUDR, 5-Fluorodeoxyuridine), Fludarabine, 5-Fluorouracil (5FU), Hydroxyurea, 6-Mercaptopurine (6 MP), Methotrexate (Amethopterin), 6-Thioguanine, Pentostatin, Pibobroman, Tegafur, Trimetrexate, Glucuronate, 5-Fluorouracil (5-FU), Pemetrexed, Antitumor antibiotics including Aclarubicin, Bleomycin, Dactinomycin (Actinomycin D), Mitomycin C, Mitoxantrone, Plicamycin (Mithramycin), Mitotic inhibitors include plant alkaloids and other natural agents that can inhibit either protein synthesis required for cell division or mitosis, Docetaxel, Vinblastine sulfate, Vincristine, Etoposide (VP16), Carboplatin, cisplatin and oxaliplatin.

A combination drug or fixed-dose combination (FDC) is a formulation of two or more active ingredients combined in a single dosage form, available in certain fixed doses. Fixed-dose combination drug products may improve medication compliance by reducing the pill burden of patients, as well as any usual advantages of combination therapy. Multiple ABS pro-drugs, monomers and particles as described herein can be co-encapsulated into a single particle or capsule, etc. or co-delivered in separate particles or capsules, etc. In either scenario, the drug release rates can be tuned as described herein to the therapeutic indication by changing the subsituent group on the silicon atom. For example, delivery of a chemotherapeutic that induces DNA damage, such as cisplatin along with a DNA repair-blocking drug such as a cdk-inhibitor therapy can improve the efficacy of the chemotherapeutic. In another example, the co-encapsulation or co-delivery of anti-nausea or pain medication with a chemotherapeutic could provide benefits as the release of these drugs can be individually tuned to release at the same time or at staggered times. Drug cocktails of antiretrovirals are usually recommended for the treatment of AIDS. Below in Table 1 are some combinations of fixed dose combinations of multiple antiretroviral drugs combined into a single pill.

TABLE 1

FDC of Antiretrovirals

| Brand Name | Drug Names (INN) | Date of FDA Approval | Company |
| --- | --- | --- | --- |
| Combivir | zidovudine + lamivudine | Sep. 26, 1997 | GlaxoSmithKline |
| Trizivir | abacavir + zidovudine + lamivudine | Nov. 15, 2000 | GlaxoSmithKline |
| Kaletra | lopinavir + ritonavir | Sep. 15, 2000 | Abbott Laboratories |
| Epzicom (in USA) Kivexa (in Europe) | abacavir + lamivudine | Aug. 2, 2004 | GlaxoSmithKline |
| Truvada | emtricitabine + tenofovir | Aug. 2, 2004 | Gilead Sciences |
| Atripla | efavirenz + emtricitabine + tenofovir | Jul. 12, 2006 | Gilead Sciences and Bristol-Myers Squibb |

Other therapeutic indications which may benefit from drug cocktails include treatment of cancer, i.e., the combination of chemotherapy and pain/nausea medications, mental illness, cardiovascular disease, asthma and arthritis; vaccines that contain antigen-adjuvants known in the art and protein-polysaccharides known in the art. In further embodiments the subject matter disclosed herein can be utilized with the particles and compositions disclosed in the following co-pending patent application publications, each of which are incorporated herein by reference in their entirety: US 2009/0028910; US 2009/0061152; WO 2007/024323; US 2009/0220789; US 2007/0264481; US 2010;0028994; US 2010;0196277; WO 2008/106503; US 2010/0151031; WO 2008/100304; WO 2009/041652; PCT/US2010/041797; US 2008/0181958; WO 2009/111588; and WO 2009/132206.

In some embodiments, the drug solubility is increased through the linkage of the present invention. The linkage of the present invention will block or protect polar functional groups, such as for example, OH, $NH_2$, COO—, SH thereby making the drug attached thereto more hydrophobic. In some embodiments where it is not desired to make the drug more hydrophobic, the particle of the present invention can be configured using highly charged or polar monomers/polymers.

According to some embodiments of the present invention, the drug concentration available at a target biologic system or location is increased through use of the linkage of the present invention. According to such embodiments, the present invention provides a system to covalently attach a drug to a particle for controlled or protected delivery. Covalently attaching the drug to the surface or interior of a particle, according to the present invention, eliminates diffusion of the drug out of or away from the particle. In some embodiments, by covalently attaching the drug to the particle ensures that the amount of drug charged (concentration before particle fabrication) and the amount of drug encapsulated (concentration after particle fabrication) are substantially similar Typically, non-covalently encapsulated drugs can be washed away from the particle leading to a considerable difference between the amount of drug charged and the amount of encapsulated drug. Moreover, due to the covalent nature of the silyl linkage, such linkage will provide particle-drug stability that is greater than the affinity binding (hydrogen bonding) found between avidin/biotin as a linker.

According to some embodiments of the present invention, utilizing the chlorosilane chemistry reaction with the particle and/or its cargo for delivery to a target location provides a reaction that is fast, simple and affordable. In some embodiments, the silane linkage can be tailored to degrade at different rates based on i) the substituent on the silicon atom, ii) the degree of lipidization, or iii) the degree of surface cross-linking. In further embodiments, the properties of a particle can be changed from hydrophobic to hydrophilic or from slowly degrading to rapidly degrading using identical reaction conditions and the chemistry is completely reversible and all modifications to the surface of the particle or drug will eventually disappear. According to some aspects of the present invention, the chlorosilane chemistry is reactive with water and therefore the reactions disclosed in the present invention should be carried out under anhydrous conditions and the particle used in association with the present invention need to be capable of withstanding anhydrous conditions.

In some embodiments, the present invention provides pro-drug linkages that are acid labile and degradable under in vivo conditions, such as for example, inflammation tumor, endosomal, or lysosomal conditions, or the like. In some embodiment, the reversible nature of the linkages facilitates releasing the linked cargo for treating or diagnosing a target in vivo condition. Di-alkyl silane linkages are acid labile and can degrade under conditions found in vivo (sights of inflammation, tumor tissue, endosomes in cells, and lysosomes in cells). These linkages can be utilized to alter the properties of a nanoparticle/liposome ranging from lipophilic to hydrophilic. Due to the reversible nature of these linkages, once the particle has reached an area of low acidity the properties of the particle can be completely reversed.

In some embodiments, the polymer is "PEG" or "poly (ethylene glycol)" as used herein, is meant to encompass any water-soluble poly(ethylene oxide). Typically, PEGs for use in the present invention will comprise the following structure: "—$(CH_2CH_2O)_n$—". The variable (n) is 3 to 3,000, or about 3 to about 30,000; about 3 to about 10,000 or about 3 to about 5,000. The terminal groups and architecture of the overall PEG may vary. PEGs having a variety of molecular weights, structures or geometries as is known in the art. "Water-soluble", in the context of a water soluble polymer is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

An "end-capping" or "end-capped" group is an inert group present on a terminus of a polymer such as PEG. An end-capping group is one that does not readily undergo chemical transformation under typical synthetic reaction conditions. An end capping group is generally an alkoxy group, —OR, where R is an organic radical comprised of 1-20 carbons and is preferably lower alkyl (e.g., methyl, ethyl) or benzyl. "R" may be saturated or unsaturated, and includes aryl, heteroaryl, cyclo, heterocyclo, and substituted forms of any of the foregoing. When the polymer has an end-capping group comprising a detectable label, the amount or location of the polymer and/or the moiety (e.g., active agent) to which the polymer is coupled, can be determined by using a suitable detector. Such labels include, without limitation, fluorescers, chemiluminescers, moieties used in enzyme labeling, calorimetric (e.g., dyes), metal ions, radioactive moieties, and the like.

As used herein, the term "tracers" include, without limitation, fluorescers, chemiluminescers, moieties used in enzyme labeling, calorimetric (e.g., dyes), metal ions, radioactive moieties, and the like.

Lipids include natural or synthetic triglycerides or mixtures of same, monoglycerides and diglycerides, alone or mixtures of same or with e.g. triglycerides, self-emulsifying modified lipids, natural and synthetic waxes, fatty alcohols, including their esters and ethers and in the form of lipid peptides, or any mixtures of same.

Practice of the method of the present invention comprises administering to a subject a therapeutically effective amount of a silyl ether compound as described herein or a delivery vehicle containing such a compound.

Routes of administration for a therapeutically effective amount of a silyl ether composition or delivery vehicle include but are not limited to intravenous or parenteral administration, oral administration, topical administration, transmucosal administration and transdermal administration. For intravenous or parenteral administration, i.e., injection or infusion, the composition may also contain suitable pharmaceutical diluents and carriers, such as water, saline, dextrose solutions, fructose solutions, ethanol, or oils of animal, vegetative, or synthetic origin. It may also contain preservatives, and buffers as are known in the art. When a therapeutically effective amount is administered by intravenous, cutaneous or subcutaneous injection, the solution can also contain components to adjust pH, isotonicity, stability, and the like, all of which is within the skill in the art. The pharmaceutical composition of the present invention may also contain stabilizers, preservatives, buffers, antioxidants, or other additive known to those of skill in the art. Typically, compositions for intravenous or parenteral administration comprise a suitable sterile solvent, which may be an isotonic aqueous buffer or pharmaceutically acceptable organic solvent. The compositions can also include a solubilizing agent as is known in the art if necessary. Compositions for intravenous or parenteral administration can optionally include a local anesthetic to lessen pain at the site of the injection. Generally, the ingredients are supplied either separately or mixed together in unit dosage form in a hermetically sealed container such as an ampoule or sachette. The pharmaceutical compositions for administration by injection or infusion can be dispensed, for example, with an infusion bottle containing, for example, sterile pharmaceutical grade water or saline. Where the pharmaceutical compositions are administered by injection, an ampoule of sterile water for injection, saline, or other solvent such as a pharmaceutically acceptable organic solvent can be provided so that the ingredients can be mixed prior to administration.

The duration of intravenous therapy using the pharmaceutical composition of the present invention will vary, depending on the condition being treated or ameliorated and the condition and potential idiosyncratic response of each individual mammal. The duration of each infusion is from about 1 minute to about 1 hour. The infusion can be repeated as necessary.

Systemic formulations include those designed for administration by injection, e.g., subcutaneous, intravenous, intramuscular, intrathecal or intraperitoneal injection. Useful injectable preparations include sterile suspensions, solutions or emulsions of the active compound(s) in aqueous or oily vehicles. The compositions also can contain solubilizing agents, formulating agents, such as suspending, stabilizing and/or dispersing agent. The formulations for injection can be presented in unit dosage form, e.g., in ampules or in multidose containers, and can contain added preservatives. For prophylactic administration, the compound can be administered to a patient at risk of developing one of the previously described conditions or diseases. Alternatively, prophylactic administration can be applied to avoid the onset of symptoms in a patient suffering from or formally diagnosed with the underlying condition.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art coupled with the general and specific examples disclosed herein.

Oral administration of the composition or vehicle can be accomplished using dosage forms including but not limited to capsules, caplets, solutions, suspensions and/or syrups.

Such dosage forms are prepared using conventional methods known to those in the field of pharmaceutical formulation and described in the pertinent texts, e.g., in *Remington: The Science and Practice of Pharmacy* (2000), supra.

The dosage form may be a capsule, in which case the active agent-containing composition may be encapsulated in the form of a liquid. Suitable capsules may be either hard or soft, and are generally made of gelatin, starch, or a cellulosic material, with gelatin capsules preferred. Two-piece hard gelatin capsules are preferably sealed, such as with gelatin bands or the like. See, for e.g., *Remington: The Science and Practice of Pharmacy* (2000), supra, which describes materials and methods for preparing encapsulated pharmaceuticals.

Capsules may, if desired, be coated so as to provide for delayed release. Dosage forms with delayed release coatings may be manufactured using standard coating procedures and equipment. Such procedures are known to those skilled in the art and described in the pertinent texts (see, for e.g., *Remington: The Science and Practice of Pharmacy* (2000), supra). Generally, after preparation of the capsule, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained-release dosage forms provide for drug release over an extended time period, and may or may not be delayed release. Generally, as will be appreciated by those of ordinary skill in the art, sustained-release dosage forms are formulated by dispersing a drug within a matrix of a gradually bioerodible (hydrolyzable) material such as an insoluble plastic, a hydrophilic polymer, or a fatty compound. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Topical administration of a silyl ether composition or delivery vehicle can be accomplished using any formulation suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams, and gels.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy* (2000), supra, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight (See, e.g., *Remington: The Science and Practice of Pharmacy* (2002), supra).

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels-are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are cross-linked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are as described elsewhere herein.

Transmucosal administration of a silyl ether composition or delivery vehicle can be accomplished using any type of formulation or dosage unit suitable for application to mucosal tissue. For example, a silyl ether composition or delivery vehicle may be administered to the buccal mucosa in an adhesive patch, sublingually or lingually as a cream, ointment, or paste, nasally as droplets or a nasal spray, or by inhalation of an aerosol formulation or a non-aerosol liquid formulation.

Preferred buccal dosage forms will typically comprise a therapeutically effective amount of a silyl ether composition or delivery vehicle and a bioerodible (hydrolyzable) polymeric carrier that may also serve to adhere the dosage form to the buccal mucosa. The buccal dosage unit is fabricated so as to erode over a predetermined time period, wherein drug delivery is provided essentially throughout. The time period is typically in the range of from about 1 hour to about 72 hours. Preferred buccal delivery preferably occurs over a time period of from about 2 hours to about 24 hours. Buccal drug delivery for short-term use should preferably occur over a time period of from about 2 hours to about 8 hours, more preferably over a time period of from about 3 hours to about 4 hours. As needed buccal drug delivery preferably will occur over a time period of from about 1 hour to about 12 hours, more preferably from about 2 hours to about 8 hours, most preferably from about 3 hours to about 6 hours. Sustained buccal drug delivery will preferably occur over a time period of from about 6 hours to about 72 hours, more preferably from about 12 hours to about 48 hours, most preferably from about 24 hours to about 48 hours. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver.

The "therapeutically effective amount" of a silyl ether composition or delivery vehicle in the buccal dosage unit will of course depend on the potency and the intended dosage, which, in turn, is dependent on the particular individual undergoing treatment, the specific indication, and the like. The buccal dosage unit will generally contain from about 1.0 wt. % to about 60 wt. % active agent, preferably on the order of from about 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with a silyl ether composition or delivery vehicle and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (Carbopol®, which may be obtained from B. F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Sublingual and lingual dosage forms include creams, ointments and pastes. The cream, ointment or paste for sublingual or lingual delivery comprises a therapeutically effective amount of the selected active agent and one or more conventional nontoxic carriers suitable for sublingual or lingual drug administration. The sublingual and lingual dosage forms of the present invention can be manufactured using conventional processes. The sublingual and lingual dosage units are fabricated to disintegrate rapidly. The time period for complete disintegration of the dosage unit is typically in the range of from about 10 seconds to about 30 minutes, and optimally is less than 5 minutes.

Other components may also be incorporated into the sublingual and lingual dosage forms described herein. The additional components include, but are not limited to binders, disintegrants, wetting agents, lubricants, and the like. Examples of binders that may be used include water, ethanol, polyvinylpyrrolidone; starch solution gelatin solution, and the like. Suitable disintegrants include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual and lingual dosage forms are known, or will be apparent, to those skilled in this art (See, e.g., *Remington: The Science and Practice of Pharmacy* (2000), supra).

Other preferred compositions for sublingual administration include, for example, a bioadhesive to retain a silyl ether composition or delivery vehicle sublingually; a spray, paint, or swab applied to the tongue; or the like. Increased residence time increases the likelihood that the administered invention can be absorbed by the mucosal tissue.

Transdermal administration of a silyl ether composition or delivery vehicle through the skin or mucosal tissue can be accomplished using conventional transdermal drug delivery systems, wherein the agent is contained within a laminated structure (typically referred to as a transdermal "patch") that serves as a drug delivery device to be affixed to the skin.

Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present, the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, those enhancers listed below in transmucosal compositions.

Formulations can comprise one or more anesthetics. Patient discomfort or phlebitis and the like can be managed using anesthetic at the site of injection. If used, the anesthetic can be administered separately or as a component of the composition. One or more anesthetics, if present in the composition, is selected from the group consisting of lignocaine, bupivacaine, dibucaine, procaine, chloroprocaine, prilocaine, mepivacaine, etidocaine, tetracaine, lidocaine and xylocaine, and salts, derivatives or mixtures thereof.

The present subject matter is further described herein by the following non-limiting examples which further illustrate the invention, and are not intended, nor should they be interpreted to, limit the scope of the invention.

EXAMPLES

1. Reversible Lipidization of Particles

Chlorosilane lipids are used to "lipidize" the surface of a particle or liposome. Chemical modification by lipidization could improve oral bioavailability, minimize enzymatic degradation of the particle and/or its cargo, alter the circulation profiles of the nanoparticles, alter the biodistribution profile, alter the hydrophilic/hydrophobic character of the drug/cargo and/or change the charge of the drug until the particle or liposome contacts a pH range whereby the covalent Si linker is cleaved and the parent cargo/drug becomes available. The reversible nature of the attachment of the lipid allows for the loss of the lipid under controlled conditions. Once the particle has reached the target, e.g., the tumor, tissue, organ, cell of interest, etc., the lipid can be cleaved under slightly acidic conditions, that allows for better accessibility and easier release of the drug. In preferred embodiments, a drug as described elsewhere herein is incorporated in the particle by a manner as described fully herein. Scheme 1 depicts a general synthetic route to prepare particles, nanoparticles or liposomes and a list of commercially available lipids.

Scheme 1

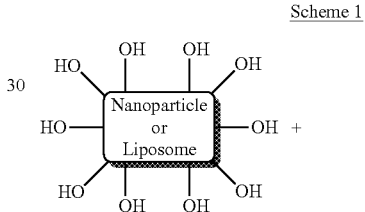

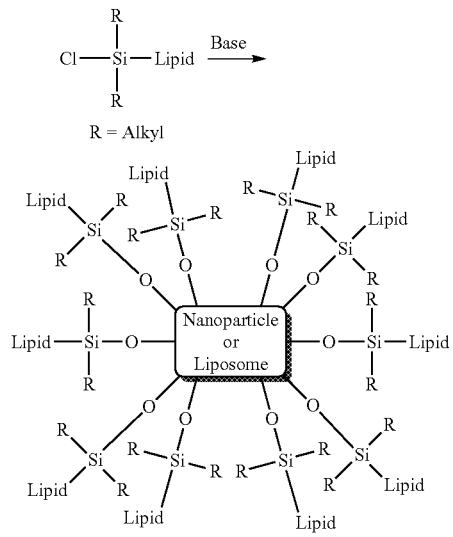

Lipids:

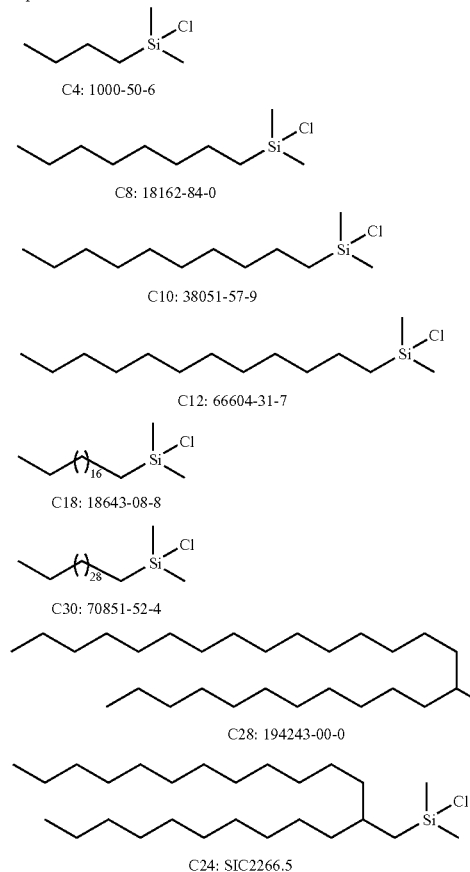

C4: 1000-50-6

C8: 18162-84-0

C10: 38051-57-9

C12: 66604-31-7

C18: 18643-08-8

C30: 70851-52-4

C28: 194243-00-0

C24: SIC2266.5

2. Reversible PEGylation of Nanoparticles

Chlorosilane poly(ethylene glycol) moieties are used to "PEGylate" the surface of a nanoparticle or liposome. Chemical modification by PEGylation can improve water solubility, circulation in vivo, and the stealth properties of the particle. The reversible nature of the attachment of the PEG allows for the cleavage of the PEG residue under desired conditions. For example, once the particle has reached the tumor, tissue, organ, cell of interest, etc. the PEG can be cleaved under slightly acidic conditions. This allows for improved accessibility to the particle and desired release of of cargo. The properties of the reversible bonds are tunable as described elsewhere herein. Scheme 2 depicts a general synthetic route to prepare particles, nanoparticles or liposomes and a list of commercially available lipids.

Poly(ethylene glycol):

SIM6492.57

36493-41-1

228700-87-6

3. Reversible PEGylation of Nanoparticles

Chlorosilane agents, which can be a pharmaceutical drug, biological or chemical agent, are used to coat the surface of a particle, nanoparticle or liposome with a payload of the agent(s). The agent is attached by a reversible silyl ether, ester, amine or thio ether linkage, which can be degraded, for example, in vivo. This chemical derivation can modify drug solubility, circulation and ensure a large concentration reaches the desired tissue. Sheme 3 depicts a general synthetic route to prepare the nanoparticles.

Scheme 2

R = Alkyl

Scheme 3

R = Alkyl

-continued

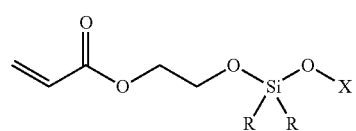

Drug: Drug-OH
Drug-NH$_2$
Drug-SH

4. Surface Modification with a Reversibly Attached Targeting Ligand

In an embodiment, a targeting ligand can also be reversibly attached to a nanoparticle through the ABS monomer system of the present invention. The targing ligand can direct the particle and drug to the cell or tissue of interest. Once the particle reaches the cell and is internalized, the targeting ligand can be cleaved allowing for better accessibility to the particle and easier release of the drug.

5. Methods of Preparing Reversible Asymmetric Silyl Ether Pro-drugs and Biologics A polymerizable chlorosilane is used to incorporate therapeutics within the interior of a nanoparticle or liposome. The therapeutic can be i) a drug/chemotherapeutic, ii) a protein, iii) a peptide, or iv) a nucleic acid (DNA, RNA, siRNA). The therapeutic is attached by a reversible silyl ether linkage, which can be degraded in vivo. This chemical modification can provide improved solubility and biodistibution to a targeted area or tissue. Additionally, having the drug inside the particle provides protection, which minimizes untimely degradation. The following structure II is an example of compounds described herein:

II wherein "X" represents a pharmaceutical, chemical or biological agent. The following schemes depict synthetic routes for the preparation of the above compounds. The selection of the alkyl substituent, R (e.g. methyl, ethyl, isopropyl, phenyl, or tert-butyl) on the Si atom can provide tunable rates of degradation. For example, a relatively bulky tert-butyl substituent leads to a more stable, less-degradable linkage. However, when a methyl or ethyl substituent was bound to the Si atom, the rate of acid catalyzed hydrolysis increases by orders of magnitude.

6. Syntheses of ABS of Camptothecin-Silyl Ether Acrylate

Scheme 4

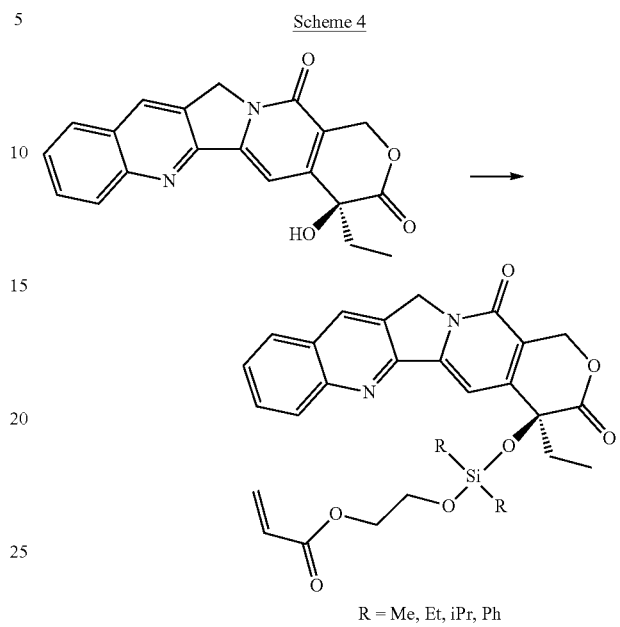

R = Me, Et, iPr, Ph a. Diethyl ABS of Camptothecin (Et-CPT)

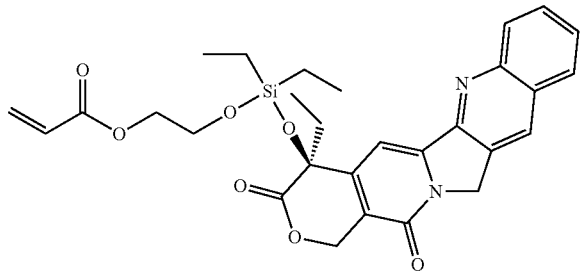

Chemical Formula: C$_{29}$H$_{32}$N$_2$O$_7$Si
Exact Mass: 548.1979

Scheme 5

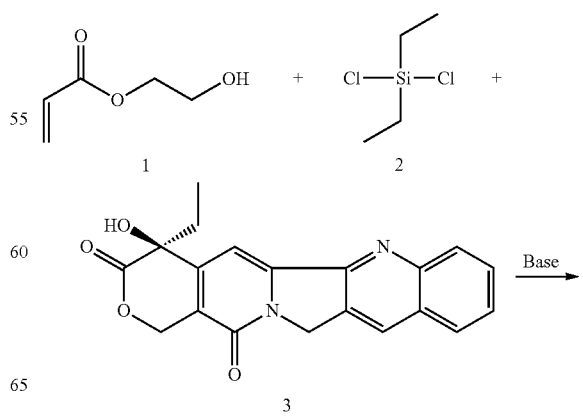

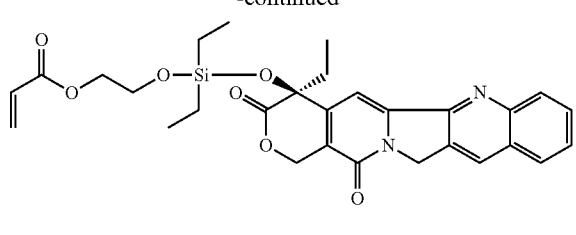

i. Method 1

To a flame-dried round-bottom flask equipped with a magnetic stir bar (under inert atmosphere), camptothecin (CPT) (0.250 g, 0.718 mmol) was suspended in 10 mL of dimethylformamide (DMF). Dimethylaminopyridine (DMAP) (0.090 g, 0.718 mmol, 1 eq.) and imidazole (0.342 g, 5.02 mmol, 7 eq.) were added to the suspension. After 10 minutes, dichlorodiethyl silane (0.338 g, 2.15 mmol, 3 eq.) was added to the suspension and allowed to react for 72 hours. Throughout the course of the reaction the heterogeneous suspension completely dissolves into the DMF solvent. Hydroxyethyl Acrylate (HEA) (0.429 g, 3.59 mmol, 5 eq.) was added and allowed to react for an additional 12 hours. The reaction solution was dissolve in 100 mL of ethyl acetate and washed with 3×50 mL of saturated sodium chloride to remove the DMF. The ethyl acetate was removed by rotary evaporation in vacuo and the product was isolated by flash chromatography using 1:1 dichloromethane:ethyl acetate as eluent. Yield: 43 mg (11%), yellow oil. $^1$H NMR (400 MHz, CDCl$_3$):δ=0.80 (m, 4H), 1.00 (m, 9H), 1.95 (quart., 2H), 4.08 (t, 2H), 4.32 (t, 2H), 5.30 (m, 3H), 5.75 (m, 2H), 6.13 (dd, 1H), 6.38 (d, 1H), 7.62 (s, 1H), 7.65 (t, 1H), 7.93 (t, 1H), 8.27 (d, 1H), 8.40 (s, 1H). HR-MS (m/z) calcd for C$_{29}$H$_{32}$N$_2$O$_7$Si, [M]$^+$=548.1979, [M+Na]$^{30}$=571.1876; found [M+Na]$^+$ m/z=571.1821.

ii. Method 2

In a dry 20 mL scintillation vial equipped with a magnetic stir bar (purged with argon), camptothecin (501 mg, 1.44 mmols), imidazole (684 mg, 10.05 mmols) and 4-DMAP (182 mg, 1.49 mmols) were dissolved in anhydrous DMF (13 mL) to form a heterogeneous mixture. A clear reaction mixture was achieved after dichlorodiethyl-silane (0.6 mL, 4.05 mmols) was added and allowed to react for 30 minutes. After 92 hours hydroxyethyl acrylate (1 mL, 9.56 mmols) was added and stirred for an additional 90 minutes. The reaction mixture was diluted with ethyl acetate (150 mL) and washed with saturated NaCl (150 mL) to remove the DMF. The organic layer was removed by rotary evaporation in vacuo, and the product was isolated by column chromatography. The product was eluted using a mixture of dichloromethane and ethyl acetate (8:2). Any residual solvent was removed in vacuo to yield an off-white liquid, 165 mg (0.30 mmols, 20.8%). $^1$H-NMR (600 MHz, CDCl$_3$):δ=0.71 (m, 2H, J=7.8 Hz), 0.84 (m, 2H, J=7.8 Hz), 0.94-1.07 (m, 6H, J=7.8 Hz), 4.10 (m, 2H), 4.31 (m, 2H), 5.33 (s, 2H), 5.40 (d, 1H, J=16.2 Hz), 5.56 (d, 1H, J=16.2 Hz), 5.80 (dd, 1H, J=1.8 Hz, J=10.2 Hz), 6.14 (dd, 1H, J=10.2 Hz, J=17.4 Hz), 6.32 (dd, 1H, J=1.8 Hz, J=17.4 Hz), 7.52 (s, 1H), 7.72 (t, 1H, J=7.2 Hz), 7.88 (t, 1H, J=7.2 Hz), 7.96 (s, 2H), 8.11 (d, 1H, J=7.8 Hz), 8.22 (d, 1H, J=8.4 Hz), 8.68 (s, 1H). MS (m/z) calcd for C$_{29}$H$_{32}$N$_2$O$_7$Si, [M]$^+$=548.1979, [M+Na]$^+$=571.1877, [M+Cs]$^+$=681.1033; found [M+Na]$^+$ m/z=571.1862, [M+Cs]$^+$=783.1003.

b. Synthesis of Dimethyl ABS of Camptothecin (Me-CPT)

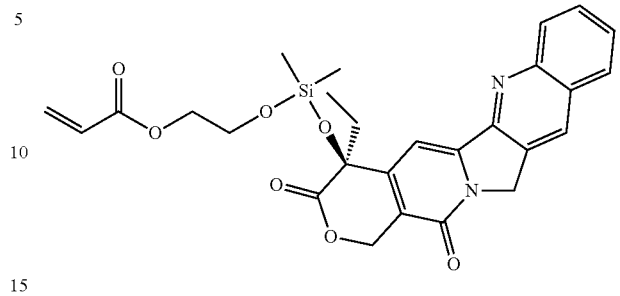

Chemical Formula: C$_{27}$H$_{28}$N$_2$O$_7$Si
Exact Mass: 520.1666

In a dry 20 mL scintillation vial equipped with a magnetic stir bar (purged with N$_2$), camptothecin (0.500 g, 1.43 mmol), 4-dimethylaminopyridine (4-DMAP) (0.175 g, 1.43 mmol) and imidazole (0.681 g, 10.01 mmol) were dissolved in anhydrous DMF (12 mL) to form a heterogeneous mixture. A clear reaction mixture was achieved after dichlorodimethyl silane (0.553 g, 4.29 mmol) was added and allowed to react for 30 minutes. After 3.5 h hydroxyethyl acrylate (HEA) (0.830 g, 7.15 mmol) was added and stirred for an additional 2 h. The reaction mixture was diluted with ethyl acetate (150 mL) and washed with saturated NaCl (150 mL) to remove the DMF. The organic layer was removed by rotary evaporation in vacuo, and the product was isolated by column chromatography. The product was eluted using a mixture of hexanes, ethyl acetate and methanol (7:2:1). The resulting solid was dried in vacuo. Yield: 107.6 mg (14.4%), yellow solid. $^1$H NMR (400 MHz, DMSO-d$_6$):δ=0.067 (s, 3H), 0.27 (s, 3H), 0.90 (t, 3H, J=7.0 Hz), 1.93 (m, 2H), 3.99 (s, 2H), 4.28 (s, 2H), 5.29 (s, 2H), 5.49 (s, 2H), 5.85 (d, 1H, J=10.2 Hz), 6.16 (dd, 1H, J=10.28 Hz, 17.24 Hz), 6.28 (d, 1H, J=17.32 Hz), 7.37 (s, 1H), 7.71 (t, 1H, J=7.4 Hz), 7.86 (t, 1H, J=8.0 Hz), 8.14 (t, 2H, J=9.48 Hz), 8.69 (s, 1H). $^{13}$C NMR (150 MHz CDCl$_3$):δ=−0.680, −0.577, 8.060, 32.686, 50.183, 61.164, 65.895, 66.241, 76.291, 98.307, 118.988, 128.142, 128.212, 128.260, 128.537, 128.625, 130.019, 130.739, 130.916, 131.221, 146.222, 149.019, 151.146, 152.517, 157.728, 166.359, 172.052. HR-MS (m/z) calcd for C$_{27}$H$_{28}$N$_2$O$_7$Si, [M]$^+$=520.1666, [M+Na]$^+$=543.1566, [M+Cs]$^+$=653.0766; found [M+Cs]$^+$=653.0720+2.8 ppm.

c. Synthesis of Diisopropyl ABS of Camptothecin (iPr—CPT)

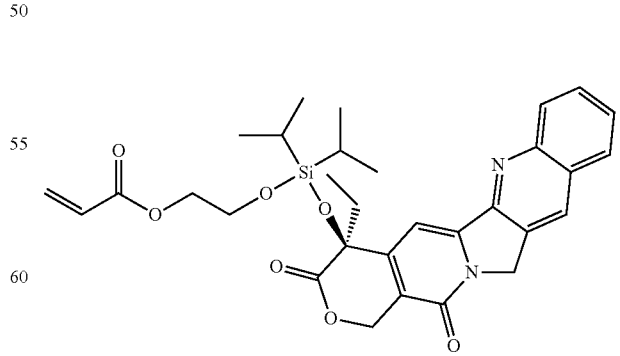

Chemical Formula: C$_{31}$H$_{36}$N$_2$O$_7$Si
Exact Mass: 576.2292

In a dry 20 mL scintillation vial equipped with a magnetic stir bar (purged with argon), camptothecin (250 mg, 0.718 mmols), imidazole (342 mg, 5.02 mmols) and 4-DMAP (90 mg, 0.737 mmols) were dissolved in anhydrous DMF (8 mL) to form a heterogeneous mixture. A clear reaction mixture was achieved after dichlorodiisopropyl silane (0.4 mL, 2.22 mmols) was added and allowed to react for 30 minutes. After 92 hours hydroxyethyl acrylate (1 mL, 9.56 mmols) was added and stirred for an additional 90 minutes. The reaction mixture was diluted with ethyl acetate (100 mL) and washed with saturated NaCl (100 mL) to remove the DMF. The organic layer was removed by rotary evaporation in vacuo, and the product was isolated by column chromatography. The product was eluted using a mixture of dichloromethane and ethyl acetate (1:1). Any residual solvent was removed in vacuo to yield an off-white liquid, 118 mg (0.21 mmols, 29.3%). $^1$H-NMR (600 MHz, CDCl$_3$): δ=0.90-1.40 (m, 14H), 1.95-2.15 (m, 2H), 4.13 (m, 2H), 4.33 (m, 2H), 5.32 (s, 2H), 5.70 (d, 1H, J=25.2 Hz), 5.77 (dd, 1H, J=1.8 Hz, J=15.6 Hz), 6.11 (dd, 1H, J=15.6 Hz, J=26.4 Hz), 6.38 (dd, 1H, J=1.8 Hz, J=26.4 Hz), 7.67 (m, 2H), 7.83 (t, 1H, J=10.8 Hz), 7.94 (d, 1H, J=12 Hz), 8.26 (d, 1H, J=13.2 Hz), 8.40 (s, 1H). MS (m/z) calcd for $C_{31}H_{36}N_2O_7Si$, [M]$^+$=576.2292, [M+H]$^+$=577.2370, [M+Na]$^+$=599.2189, [M+Cs]$^+$=709.1346; found [M+H]$^+$=577.2362, [M+Na]$^+$=599.2207, [M+Cs]$^+$=709.1329.

d. Synthesis of Diphenyl ABS of Camptothecin (Ph-CPT)

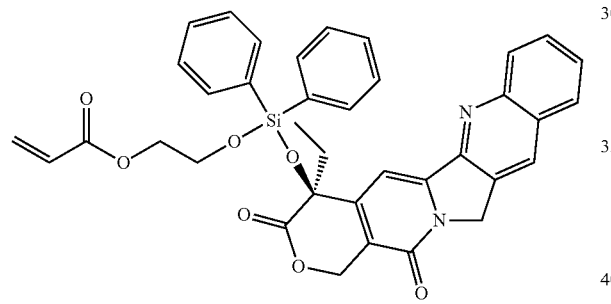

Chemical Formula: $C_{37}H_{32}N_2O_7Si$
Exact Mass: 644.1979

In a dry 20 mL scintillation vial equipped with a magnetic stir bar (purged with argon), camptothecin (500 mg, 1.44 mmols), imidazole (684 mg, 10.05 mmols) and 4-DMAP (180 mg, 1.47 mmols) were dissolved in anhydrous DMF (15 mL) to form a heterogeneous mixture. A clear reaction mixture was achieved after dichlorodiphenyl silane (1.0 mL, 4.74 mmols) was added and allowed to react for 45 minutes. After 92 hours hydroxyethyl acrylate (1 mL, 9.56 mmols) was added and stirred for an additional 60 minutes. The reaction mixture was diluted with ethyl acetate (150 mL) and washed with saturated NaCl (150 mL) to remove the DMF. The organic layer was removed by rotary evaporation in vacuo, and the product was isolated by column chromatography. The product was eluted using a mixture of dichloromethane and ethyl acetate (8:2). Any residual solvent was removed in vacuo to yield a pale yellow solid, 178 mg (0.28 mmols, 19.4%). $^1$H-NMR (600 MHz, CDCl$_3$):δ=1.01 (t, 3H), 2.08-2.30 (m, 2H), 4.12 (br, 2H), 4.37 (br, 2H), 5.26 (m, 3H), 5.47 (d, 1H, J=16.8 Hz), 5.77 (d, 1H, J=10.2 Hz), 6.07 (m, 1H), 6.35 (d, 1H, J=17.4 Hz), 7.30-7.50 (m, 4H), 7.57 (s, 1H), 7.70 (br, 5H), 7.87 (t, 1H, J=7.2 Hz), 7.97 (d, 1H, J=7.8 Hz), 8.24 (d, 1H, J=8.4 Hz), 8.40 (s, 1H). MS (m/z) calcd for $C_{37}H_{32}N_2O_7Si$, [M]$^+$=644.1979, [M+Na]$^+$=667.1876, [M+Cs]$^+$=777.1033; found [M+Cs]$^+$=777.1141.

According to some embodiments, reversible linkages based on dialkylchloro silanes are used to change the intrinsic characteristics of nanoparticles and liposomes. Each chlorosilane was investigated using particles fabricated from the Particle Replication In Non-wetting Templates (PRINT) process.

7. Additional ABS of Alkaloids—Silyl Ether Quinoline Alkaloids

Scheme 6 depicts Topotecan and a preferred attachment:

Scheme 6

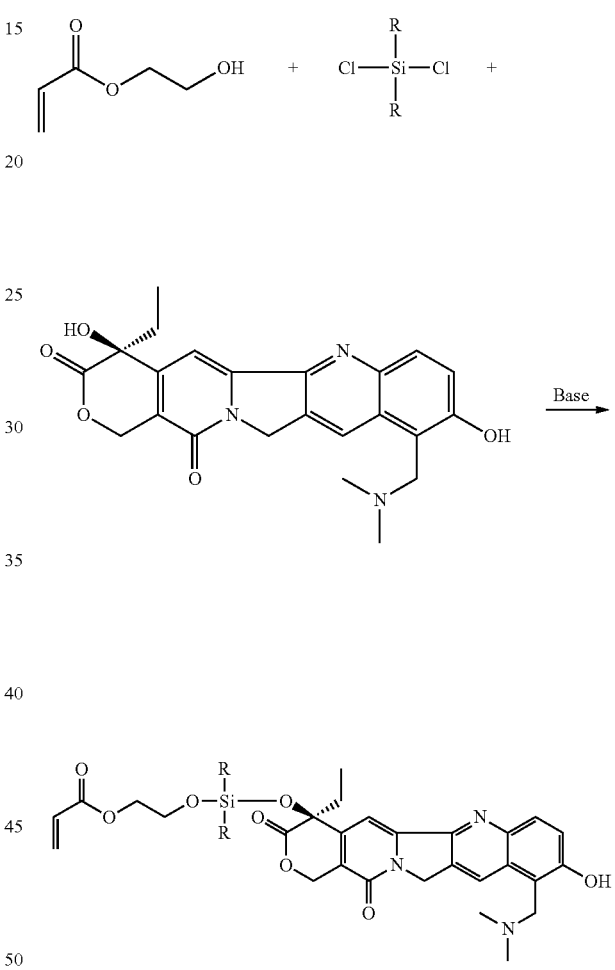

However, other potential sights of silane attachment are denoted with X in the following structure III:

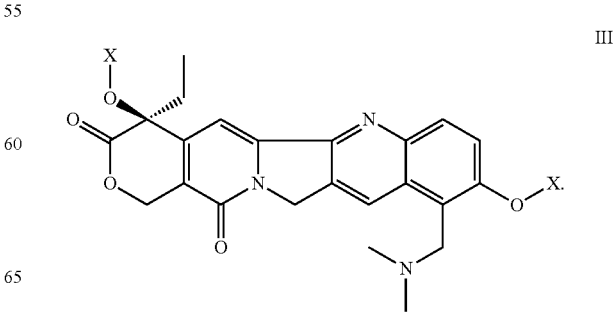

III

Scheme 7 depicts Irinotecan and a preferred attachment:
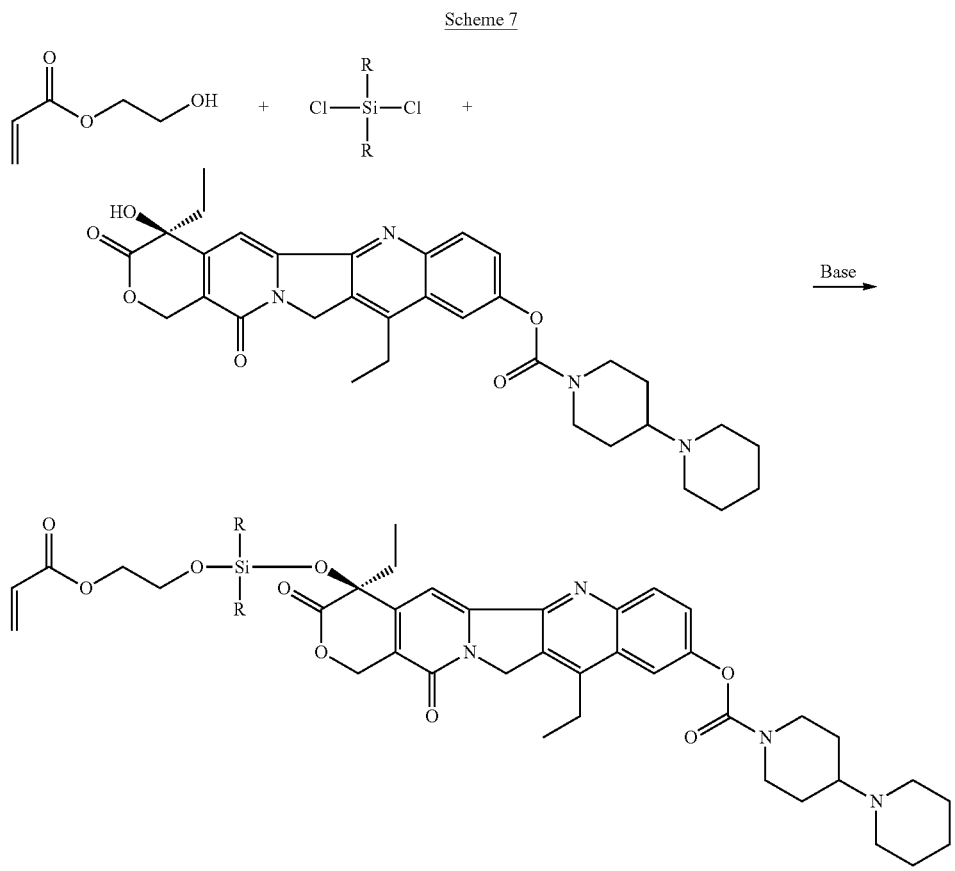
Scheme 8 depicts SN-38 and a preferred attachment:
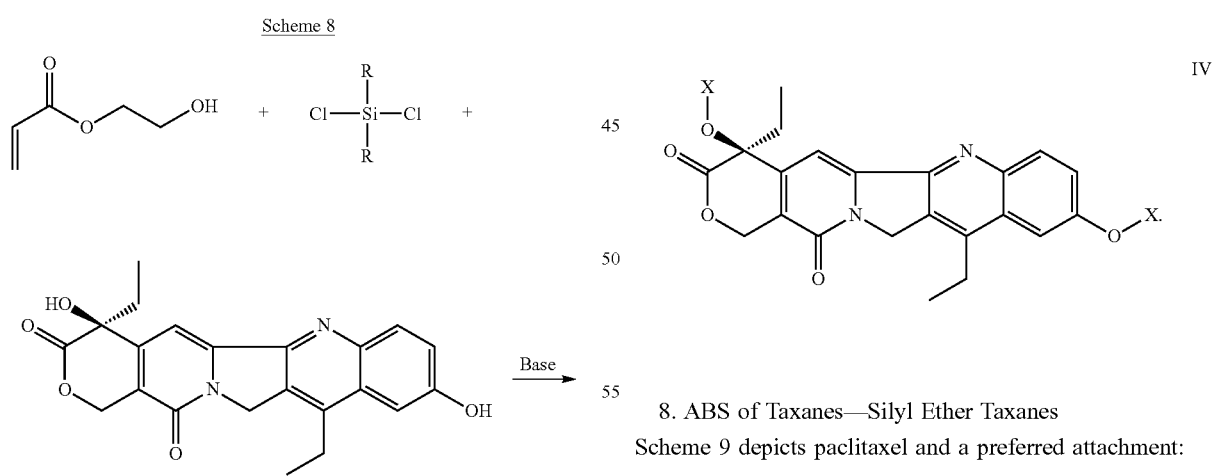
However, other potential sights of silane attachment are denoted with X in the following structure IV:
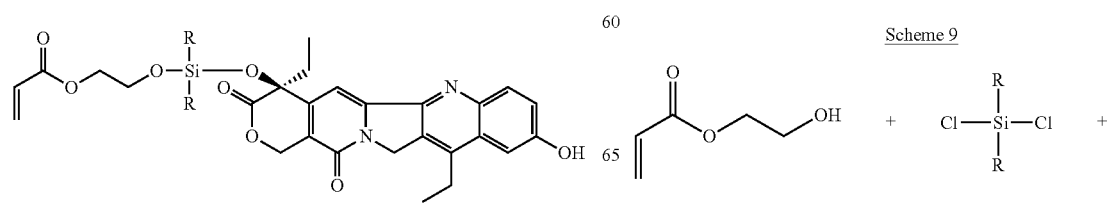
8. ABS of Taxanes—Silyl Ether Taxanes
Scheme 9 depicts paclitaxel and a preferred attachment:

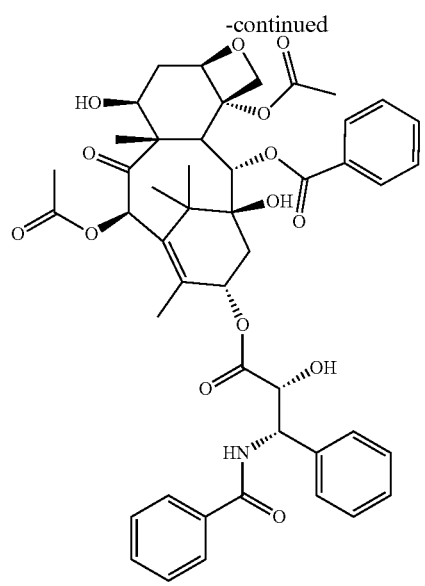
Scheme 10 depicts Docetaxel and a preferred attachment:
Scheme 10
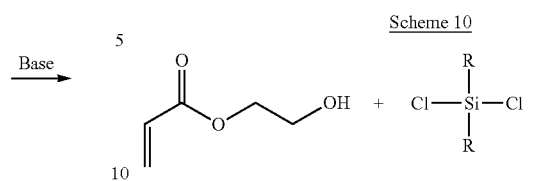
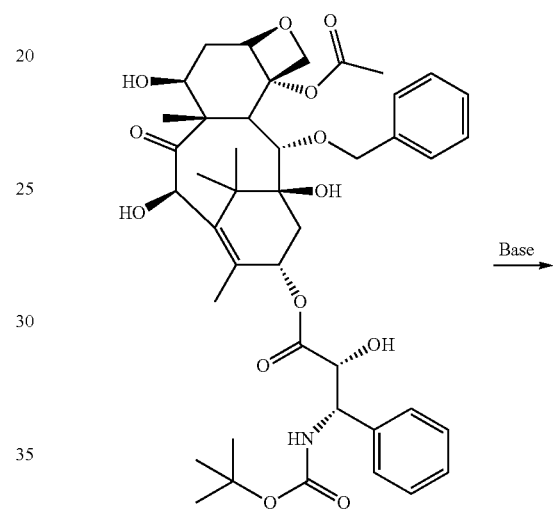
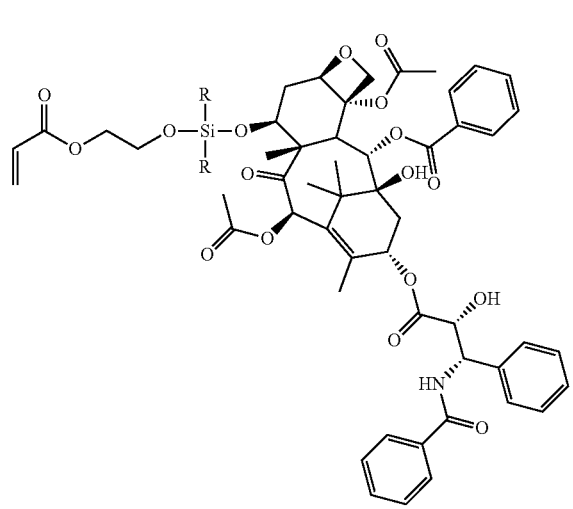
However, other potential sights of silane attachment are denoted with X in the following structure:
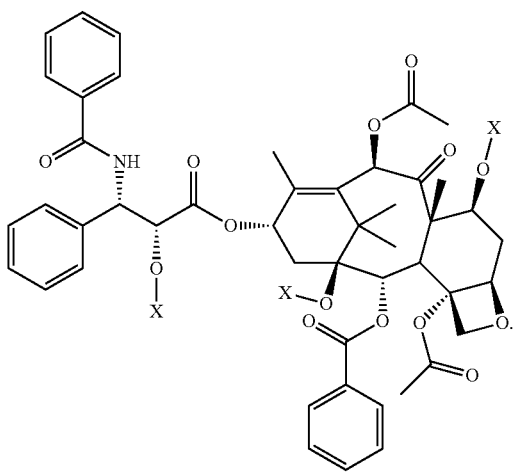
IV
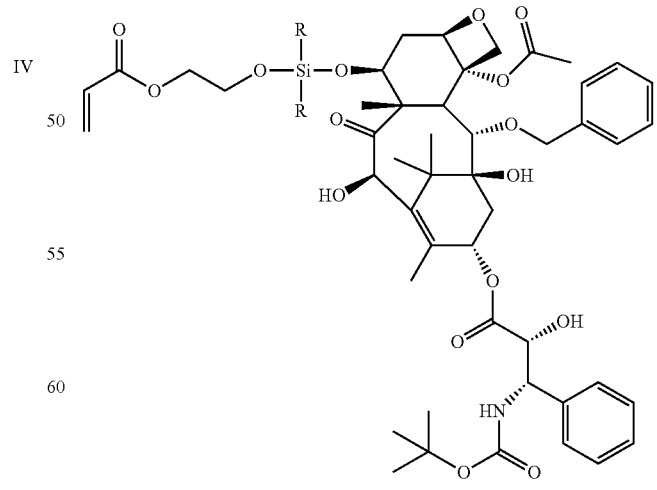
However, other potential sights of silane attachment are denoted with X in the following structure V:

9. ABS of Anthracyclines—Silyl Ether Anthracyclines

Scheme 11 depicts Daunorubicin and a preferred attachment:

Scheme 11

However, other potential sights of silane attachment are denoted with X in the following structure VI:

Scheme 12 depicts Doxorubicin and a preferred attachment:

Scheme 12

However, other potential sights of silane attachment are denoted with X in the following structure VII:

Scheme 13 depicts Epirubicin and a preferred attachment:

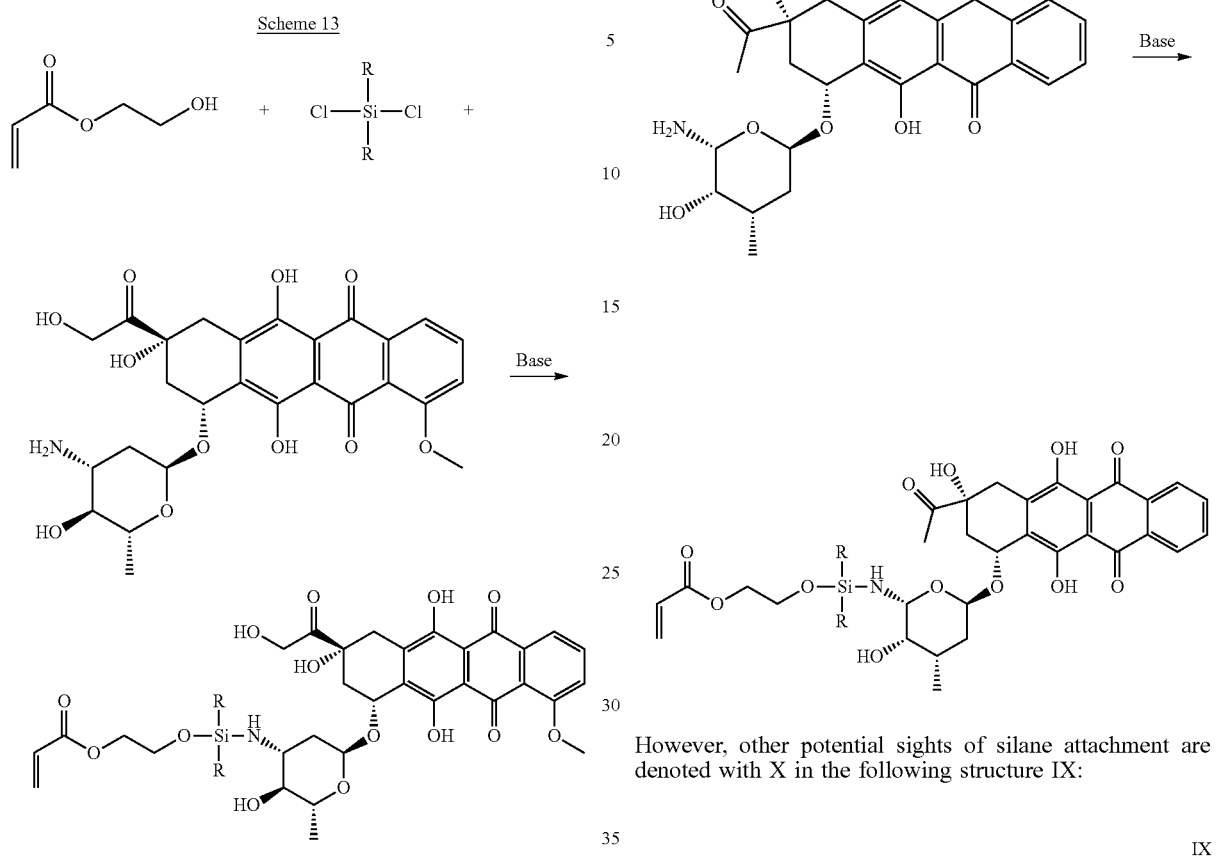

However, other potential sights of silane attachment are denoted with X in the following structure VIII:

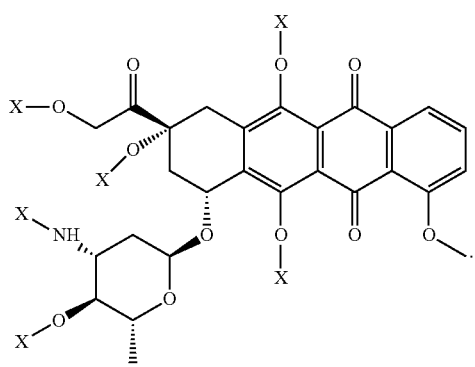

VIII

Scheme 14 depicts Idarubicin and a preferred attachment:

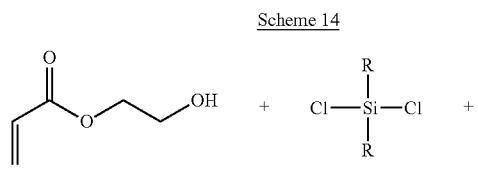

However, other potential sights of silane attachment are denoted with X in the following structure IX:

IX

10. ABS of Nucleosides—Silyl Ether Nucleosides

Scheme 15

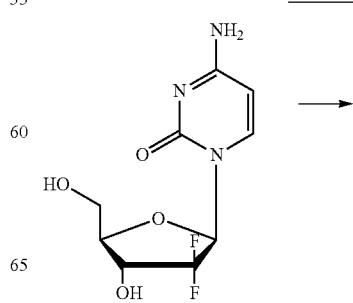

-continued

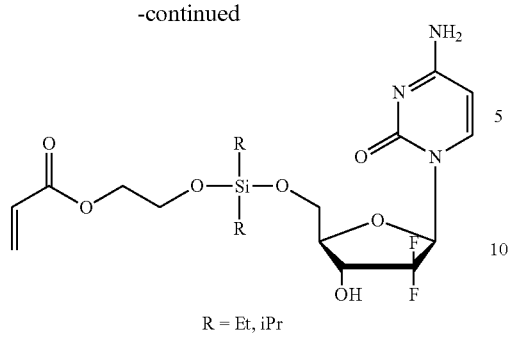

R = Et, iPr

Scheme 16 depicts Gemcitabine and a preferred attachment:

Scheme 16

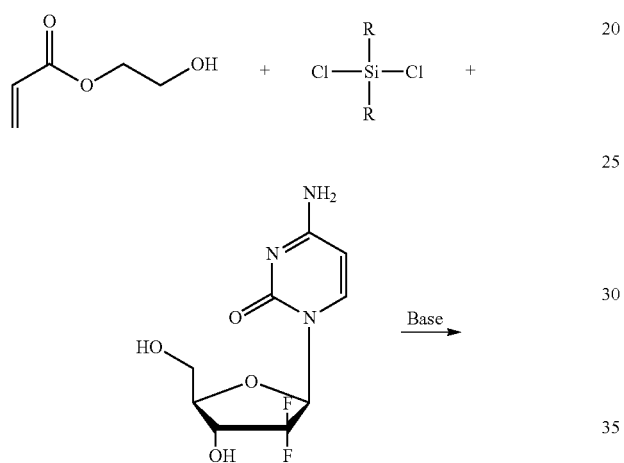

However, other potential sights of silane attachment are denoted with X in the following structure X':

X'

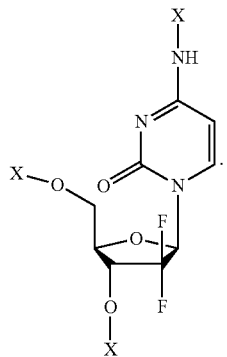

Scheme 17 depicts Cytarabine and a preferred attachment:

Scheme 17

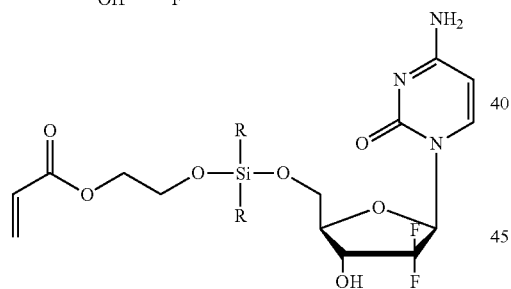

However, other potential sights of silane attachment are denoted with X in the following structure XI:

XI

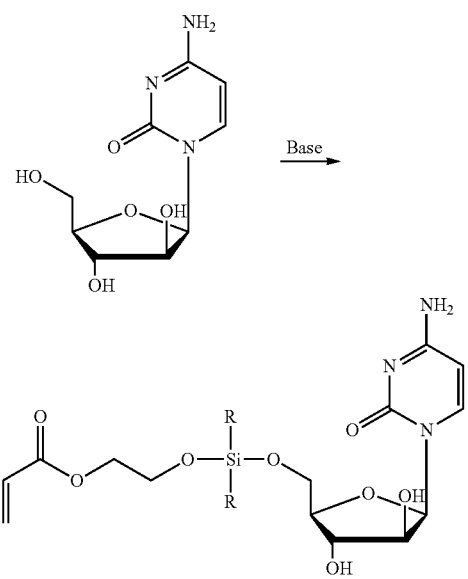

a. Diethyl ABS of Gemcitabine (Et-GEM)

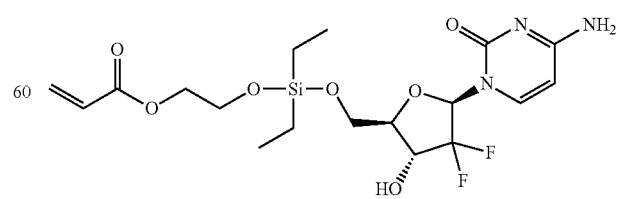

Chemical Formula: $C_{18}H_{27}F_2N_3O_7Si$
Exact Mass: 463.1586

In a dry 20 mL scintillation vial equipped with a magnetic stir bar (purged with argon), gemcitabine hydrochloride (500 mg, 1.67 mmols), imidazole (264 mg, 3.88 mmols) and 4-DMAP (204 mg, 1.67 mmols) were dissolved in anhydrous DMF (15 mL). After 15 minutes dichlorodiethyl silane (0.2 mL, 1.35 mmols) was added and allowed to react. After 60 minutes hydroxyethyl acrylate (1 mL, 9.56 mmols) was added and stirred for an additional 30 minutes. The reaction mixture was diluted with ethyl acetate (150 mL) and washed with saturated NaCl (150 mL) to remove the DMF. The organic layer was removed by rotary evaporation in vacuo, and the product was isolated by column chromatography. The product was eluted using a mixture of dichloromethane and methanol (9:1). Any residual solvent was removed in vacuo to yield a clear and colorless liquid (1° isomer) with a yield of 282 mg (0.61 mmols, 38.4%). $^1$H-NMR (600 MHz, CDCl$_3$):δ=0.66 (m, 4H, J=7.8 Hz), 0.96 (t, 6H, J=7.8 Hz), 1.50-2.30 (br, 1H), 3.90-4.18 (m, 5H), 4.20-4.40 (m, 3H), 5.80-5.90 (m, 2H), 6.10-6.20 (dd, 1H, J=10.2 Hz, J=17.4 Hz), 6.31 (t, 1H, J=7.2 Hz), 6.42 (dd, 1H, J=1.2 Hz, J=17.4 Hz), 7.70 (d, 1H, J=7.8 Hz). $^{13}$C-NMR (150 MHz, CDCl$_3$):δ=3.67, 6.35, 6.36, 50.98, 60.35, 60.93, 61.37, 65.70, 66.36, 69.31 (t, CF$_2$ coupling, J$_{C-F}$=22.5 Hz), 80.75, 84.31 (m, CF$_2$ coupling), 95.55, 122.52 (t, CF$_2$ coupling, J$_{C-F}$=258 Hz), 128.18, 131.57, 131.66, 140.93, 156.01, 165.92, 166.68. MS (m/z) calcd for C$_{18}$H$_{27}$F$_2$N$_3$O$_7$Si, [M]$^+$= 463.1586, [M +Na]$^+$=486.1484, [M+Cs]$^+$=596.0641; found [M+Na]$^+$ m/z=486.1483, [M+Cs]$^+$=596.0662.

Additionally, the 2° isomer was also isolated as a foamy semi-solid, 195 mg (0.42 mmols, 26.5%). $^1$H-NMR (600 MHz, CDCl$_3$):δ=0.69 (q, 4H, J=7.8 Hz), 0.98 (t, 6H, J =7.8 Hz), 1.50-2.20 (br, 3H), 3.80 (dd, 1H, J=2.4 Hz, 12.6 Hz), 3.91 (d, 1H, J=8.4 Hz), 3.95 (t, 2H, J=4.8 Hz), 4.04 (d, 1H, J=12 Hz), 4.22-4.30 (m, 2H, J=6.6 Hz, 4.8 Hz), 4.43-4.63 (br, 1H), 5.85 (dd, 2H, J=1.2 Hz, 10.8 Hz), 6.05-6.35 (br and dd, 2H, J=10.2 Hz, J=17.4 Hz), 6.42 (dd, 1H, J=1.2 Hz, 17.4 Hz), 7.10-7.50 (br, 1H), 7.58 (d, 1H, J=7.2 Hz). $^{13}$C-NMR (150 MHz, CDCl$_3$):δ=3.82, 3.89, 6.11, 6.14, 59.38, 61.01, 65.55, 69.76 (t, CF$_2$ coupling, J$_{C-F}$=22.5 Hz), 81.06, 84.90 (m, CF$_2$ coupling), 96.34, 122.31 (t, CF$_2$ coupling, J$_{C-F}$=258 Hz), 128.24, 131.40, 141.13, 156.18, 166.22, 166.46. MS (m/z) calcd for C$_{18}$H$_{27}$F$_2$N$_3$O$_7$Si, [M]$^+$= 463.1586, [M+Na]$^+$=486.1484, [M+Cs]$^+$=596.0641; found [M+Na]$^+$ m/z=486.1467, [M+Cs]$^+$=596.0649.

b. Diisopropyl ABS of Gemcitabine (iPr-GEM)

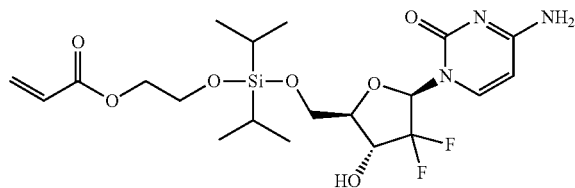

Chemical Formula: C$_{20}$H$_{31}$F$_2$N$_3$O$_7$Si
Exact Mass: 491.1899

In a dry 20 mL scintillation vial equipped with a magnetic stir bar (purged with argon), gemcitabine hydrochloride (507 mg, 1.69 mmols), imidazole (271 mg, 3.98 mmols) and 4-DMAP (209 mg, 1.71 mmols) were dissolved in anhydrous DMF (13 mL). After 15 minutes dichlorodiisopropyl silane (0.25 mL, 1.39 mmols) was added and allowed to react. After 135 minutes hydroxyethyl acrylate (1 mL, 9.56 mmols) was added and stirred for an additional 60 minutes. The reaction mixture was diluted with ethyl acetate (150 mL) and washed with saturated NaCl (150 mL) to remove the DMF. The organic layer was removed by rotary evaporation in vacuo, and the product was isolated by column chromatography. The product was eluted using a mixture of dichloromethane and methanol (9:1). Any residual solvent was removed in vacuo to yield a white solid (1° isomer) with a yield of 260 mg (0.53 mmols, 33%). $^1$H-NMR (600 MHz, CDCl$_3$):δ=1.05 (d, 14H, J=2.4 Hz), 3.99 (t, 2H, J=4.8 Hz), 4.01-4.45 (m, 6H), 4.70-5.60 (br, 1H), 5.85 (m, 2H), 6.15 (dd, 1H, J=10.8 Hz, J=17.4 Hz), 6.26 (br, 1H), 6.35 (t, 1H, J=7.8 Hz), 6.42 (dd, 1H, J=1.2 Hz, J=17.4 Hz), 7.64 (d, 1H, J=7.2 Hz), 7.86 (br, 1H). $^{13}$C-NMR (150 MHz, CDCl$_3$): δ=11.85, 11.92, 17.11, 17.13, 17.17, 60.61, 61.10, 61.14, 65.53, 65.57, 66.49, 69.41 (t, CF$_2$ coupling, J$_{C-F}$=22.5 Hz), 72.89, 80.84, 84.02 (q, CF$_2$ coupling, J$_{C-F}$ =24 Hz, 36 Hz), 95.50 (d, J=6 Hz), 96.26, 122.37 (t, CF$_2$ coupling, J$_{C-F}$=258 Hz), 128.10, 131.47, 139.92 (br, CF$_2$ coupling), 140.80, 155.51, 155.86, 165.82, 166.55. MS (m/z) calcd for C$_{20}$H$_{31}$F$_2$N$_3$O$_7$Si, [M]$^+$=491.1899, [M+Na]$^+$=514.1797, [M+Cs]$^+$=624.0954; found [M+Na]$^+$ m/z=514.1765, [M+Cs]$^+$=624.0959.

Additionally, the 2° isomer was also isolated as a clear oil, 193 mg (0.39 mmols, 24.3%). $^1$H-NMR (600 MHz, CDCl$_3$): δ=1.03 (s, 14H), 3.79 (d, 1H, J=10.8 Hz), 3.88 (d, 1H, J=7.8 Hz), 4.00 (t, 2H, J=4.8 Hz), 4.05 (d, 1H, J=12.6 Hz), 4.27 (m, 2H, J =5.4 Hz, J=6.6 Hz), 4.51 (br, 2H), 5.85 (t, 2H, J=9.6 Hz, 7.2 Hz), 6.12 (dd, 1H, J=10.5 Hz, J=17.4 Hz), 6.22 (br, 1H), 6.41 (d, 1H, J=17.4 Hz), 6.80 (br, 1H), 7.53 (d, 1H, J=7.8 Hz), 7.90 (br, 1H). $^{13}$C-NMR (150 MHz, CDCl$_3$): δ=11.87, 11.99, 16.70, 16.80, 16.85, 16.88, 50.67 (p, J=7.5 Hz, J=3 Hz), 59.37, 61.27, 65.39, 69.79 (t, CF$_2$ coupling, J$_{C-F}$=22.5 Hz), 81.21, 84.90 (br, CF$_2$ coupling), 96.12, 122.15 (t, CF$_2$ coupling, J$_{C-F}$=258 Hz), 128.04, 131.34, 141.01, 155.97, 165.97, 166.37. MS (m/z) calcd for C$_{20}$H$_{31}$F$_2$N$_3$O$_7$Si, [M]$^+$=491.1899, [M+Na]$^+$=514.1797, [+Cs]$^+$=624.0954; found [M+Na]$^+$ m/z=514.1780, [M+Cs]$^+$= 624.0894.

c. Di-tert-butyl ABS of Gemcitabine (tBu-GEM)

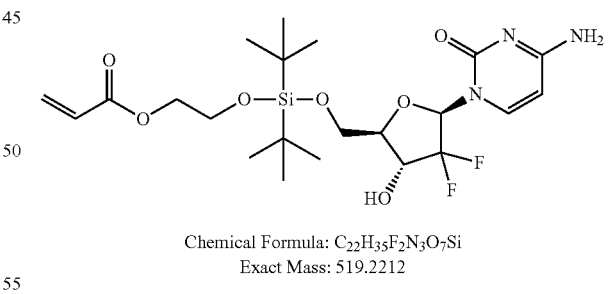

Chemical Formula: C$_{22}$H$_{35}$F$_2$N$_3$O$_7$Si
Exact Mass: 519.2212

To a 50 mL round bottom flask equipped with a magnetic stir bar (purged with argon) di-tert-butylsilyl bis(trifluoromethanesulfonate) (0.84 g, 1.90 mmol) was dissolved in anhydrous DMF (12 mL) and anhydrous pyridine (1 mL) and cooled in an ice bath. Hydroxyethyl acrylate (0.22 g, 1.90 mmol) was diluted in 6 mL of anhydrous DMF and added to the reaction in a drop wise fashion over one hour. The reaction was allowed to stir and warm to room temperature for 2 hours after which gemcitabine (0.50 g, 1.90 mmol) was added and allowed to react overnight. The reaction mixture was diluted with ethyl acetate (150 mL) and washed with saturated NaCl (150 mL) to remove the DMF. The organic layer was removed by rotary evaporation in vacuo, and the product was isolated by column chromatography. The product was eluted using a mixture of dichloromethane and methanol (92:8 ratio). Any residual solvent was removed in vacuo and gave colourless foam with a yield of 192 mg (0.37 mmol, 20%). $^1$H-NMR (400 MHz, CDCl$_3$): δ=1.00 (d, 18H, J=2.0 Hz), 4.00-4.23 (m, 5H), 4.23-4.37 (m, 3H), 5.84 (d, 1H, J=10.4 Hz), 5.89 (d, 1H, J=7.6 Hz), 6.10 (dd, 1H, J=10.4 Hz, 17.4 Hz), 6.27 (t, 1H, J=8.0 Hz), 6.39 (dd, 1H, J=1.6 Hz, 17.4 Hz), 7.54 (d, 1H, J=7.2 Hz). $^{13}$C-NMR (150 MHz, CDCl$_3$):δ=21.27, 21.33, 27.81, 27.87, 61.85, 62.22, 65.87, 69.90 (dd, J$_{CF}$=18.0 Hz, 27.0 Hz), 81.51, 83.99 (m), 96.20, 119.35, 120.67, 122.40, 124.12, 128.28, 131.69, 141.04, 155.90, 165.36, 166.78. MS (m/z) calcd for C$_{22}$H$_{35}$F$_2$N$_3$O$_7$Si, [M]$^+$=519.2212, [M+Na]$^+$=542.2110, [M+Cs]$^+$=652.1267; found [+Na]$^+$ m/z=542.17, [M+Cs]$^+$=652.08.

11. Silyl Ether Brefeldin-A

Scheme 18 depicts ABS Brefeldin-A and a preferred attachment:

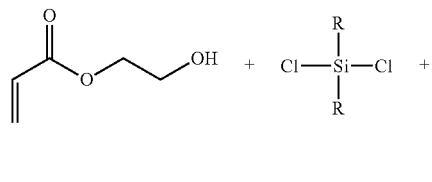

Scheme 18

However, other potential sights of silane attachment are denoted with X in the following structure XII:

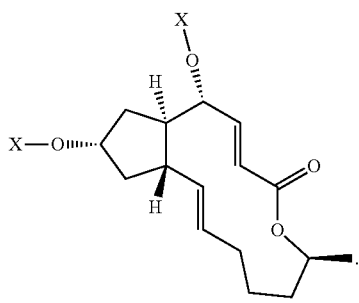

XII

12. Silyl Ether Tyrosine Kinase Inhibitors

Scheme 19 depicts Cytarabine and a preferred attachment:

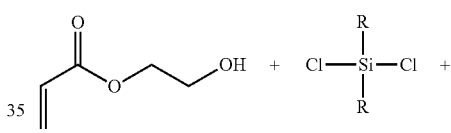

Scheme 19

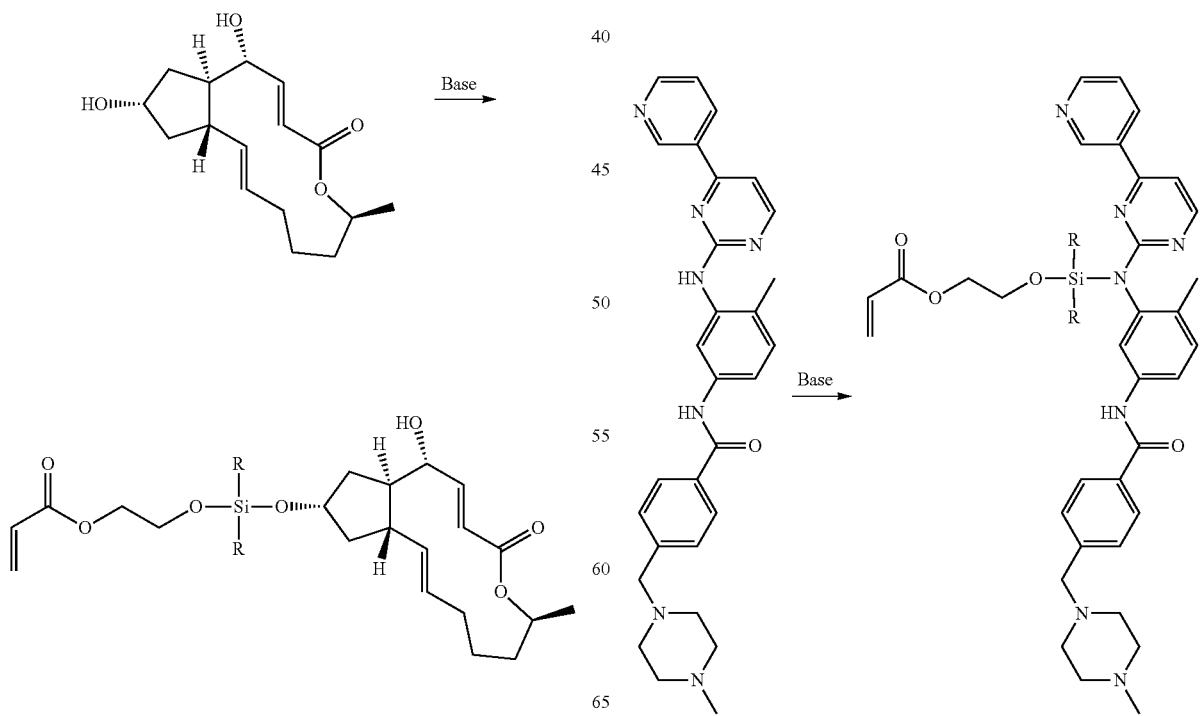

Scheme 20 depicts Gefitinib and a preferred attachment:
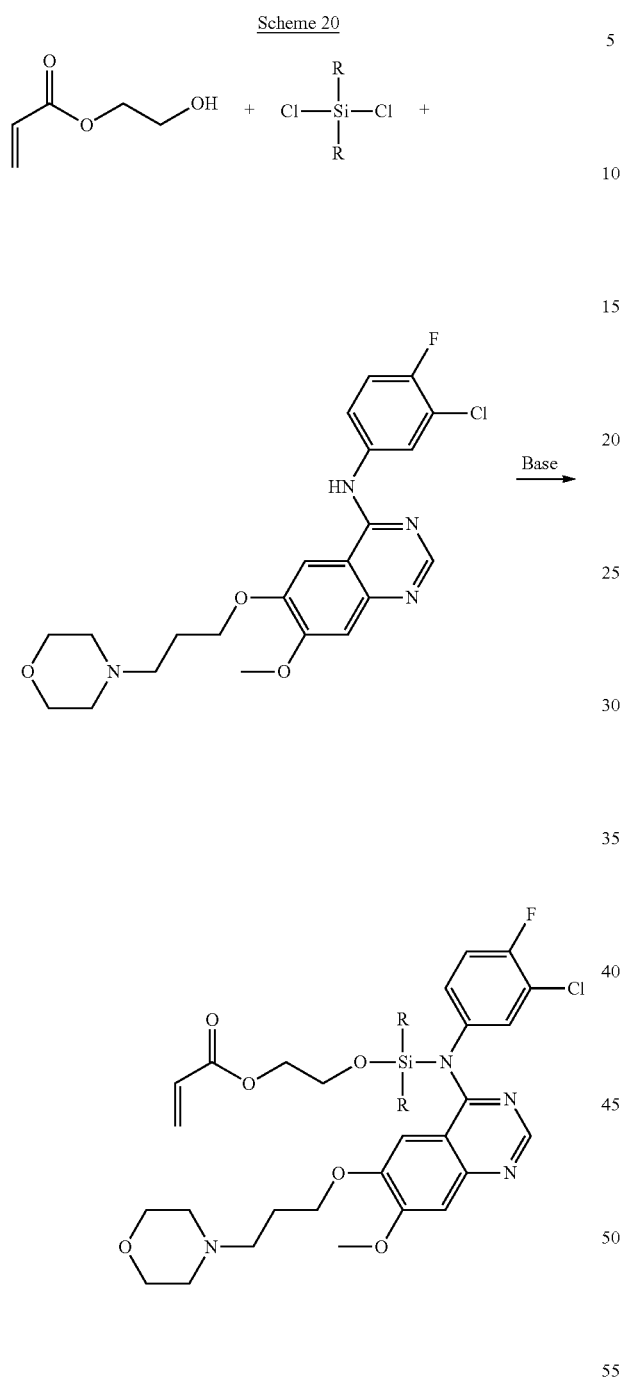
Scheme 21 depicts Lapatinib and a preferred attachment:
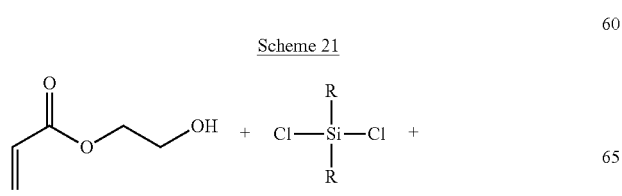
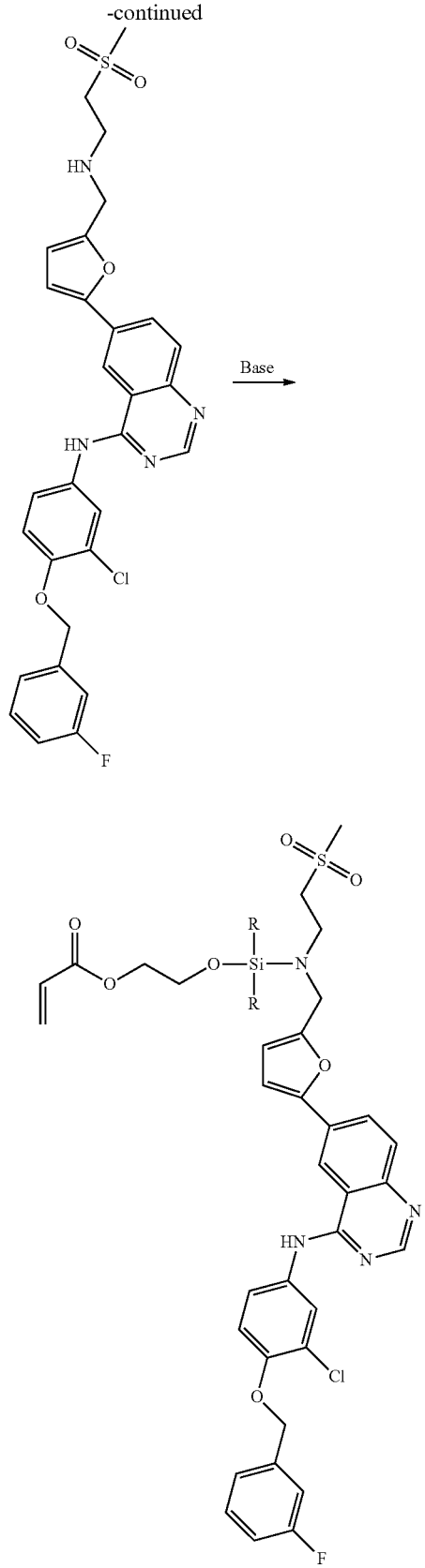
However, other potential sights of silane attachment are denoted with X in the following structure XIII:

XIII
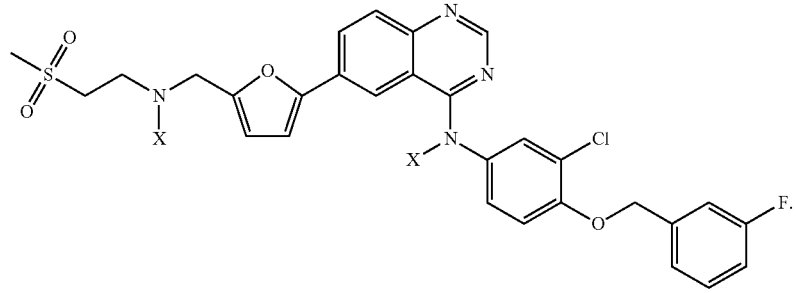
Scheme 22 depicts Sunitinib and a preferred attachment:
Scheme 22
-continued
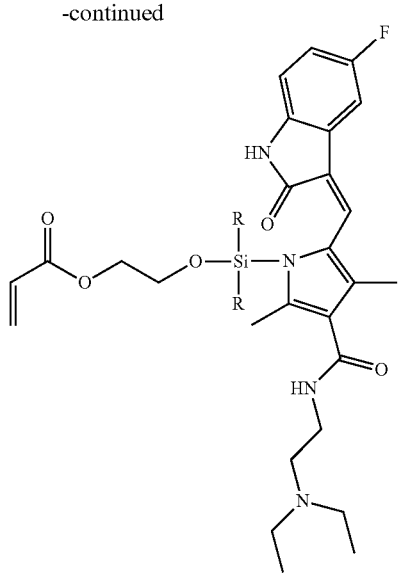
13. Silyl Ether Antifolates
Scheme 23 depicts Methotrexate and a preferred attachment:
Scheme 23
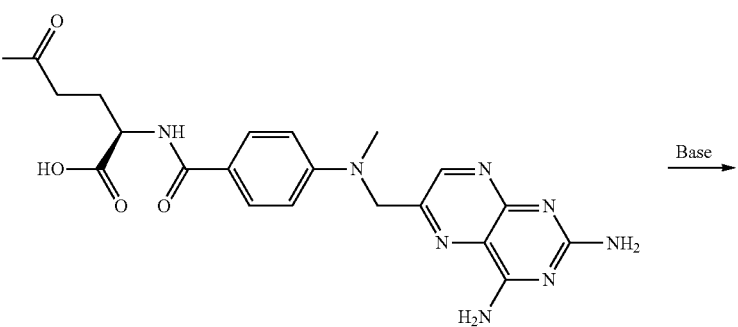

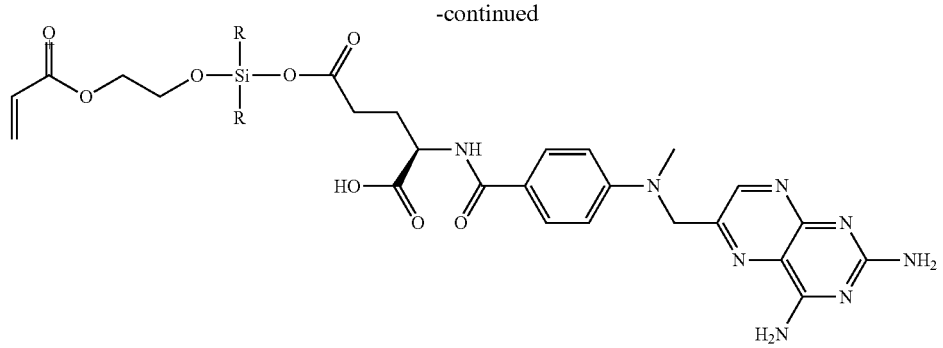
However, other potential sights of silane attachment are denoted with X in the following structure XIV:
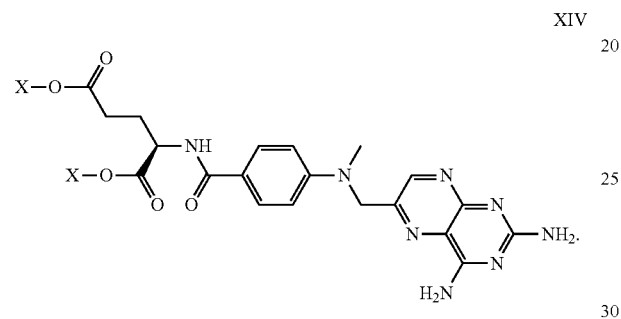
Scheme 24 depicts Folinic Acid and a preferred attachment:
Scheme 24
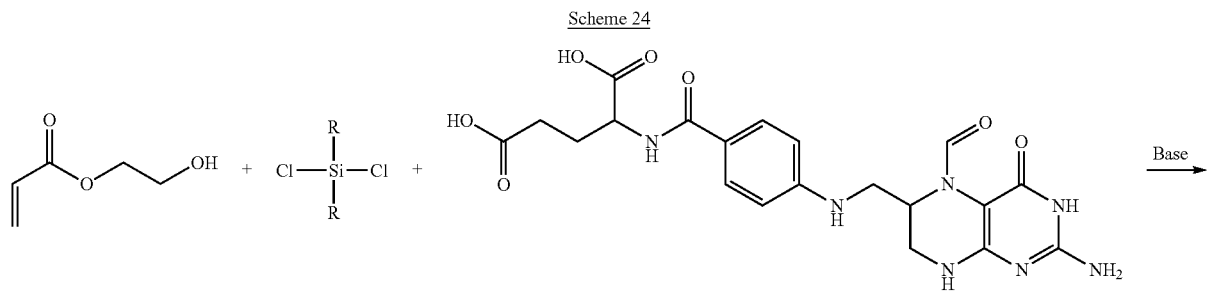
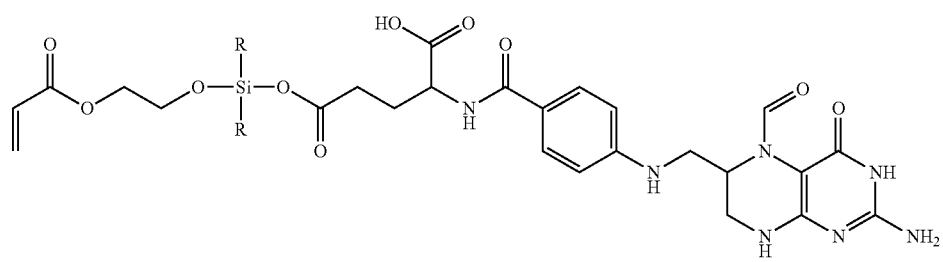

However, other potential sights of silane attachment are denoted with X in the following structure XV:

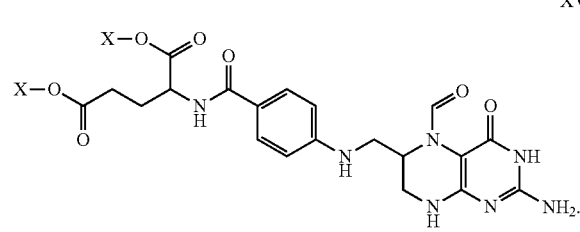

14. Silyl Ether Proteins

Scheme 25 depicts Ctochrome C, Ovalbumin, etc. and a preferred attachment at side group:

Scheme 25

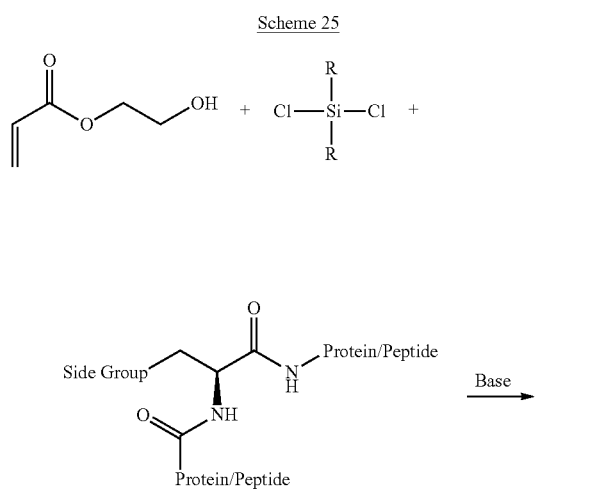

15. Silyl Ether Nucleic Acids

Silyl ether nucleic acids such as RNA, siRNA, RNA Replicon, etc. can be prepared. Scheme 26 depicts a synthetic route via functionalization of the hydroxyls on the side of the RNA chain.

Scheme 26

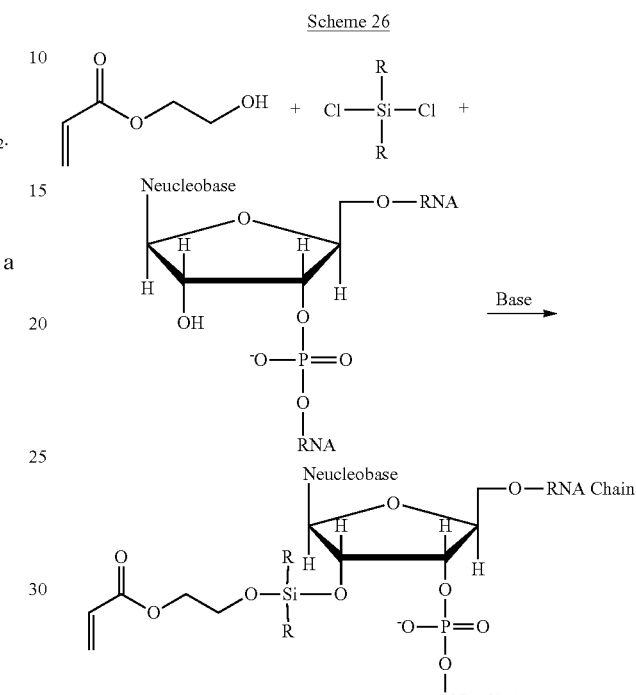

Scheme 27 depicts a synthetic route via functionalization of the hydroxyls on the end of the RNA chain.

Scheme 27

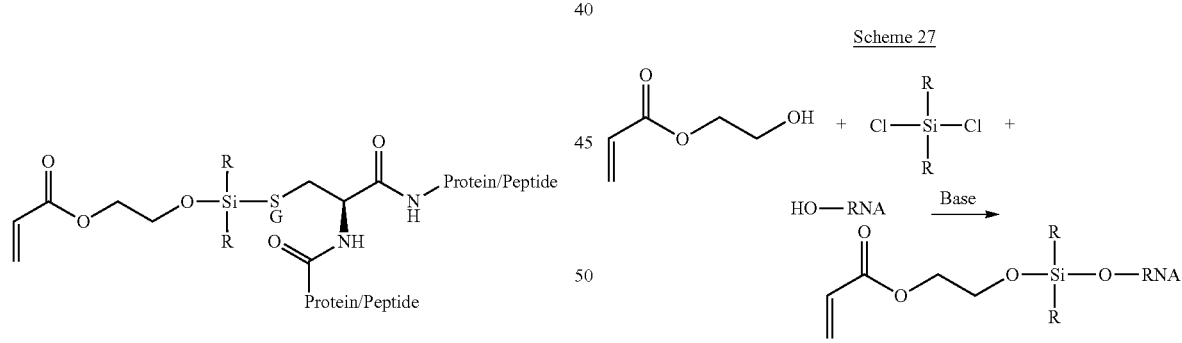

FIG. 1 depicts exemplary amino acid residues that can provide a sight of silane attachment.

16. ABS of Dasatinab

Scheme 28

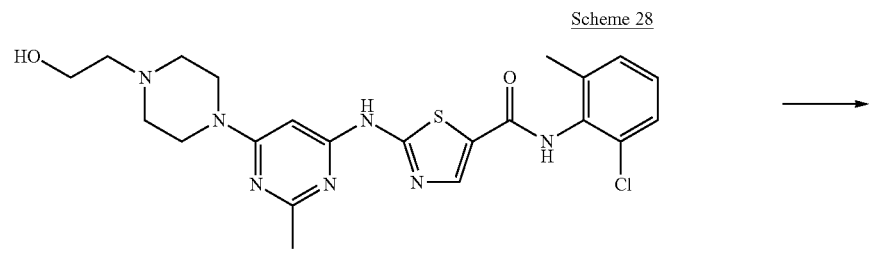

-continued

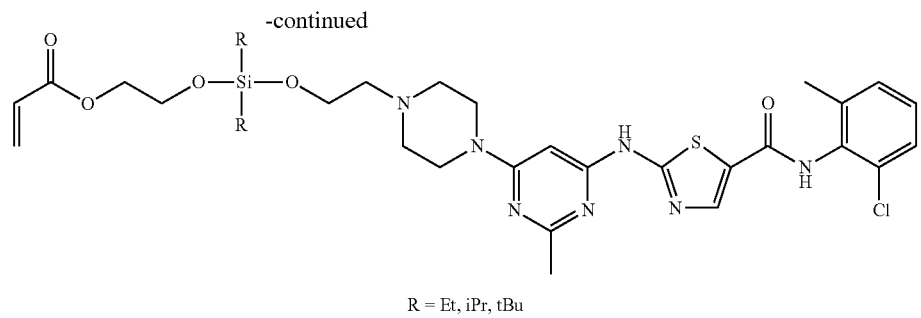

R = Et, iPr, tBu a. Diethyl ABS of Dasatinab (Et-DAS)

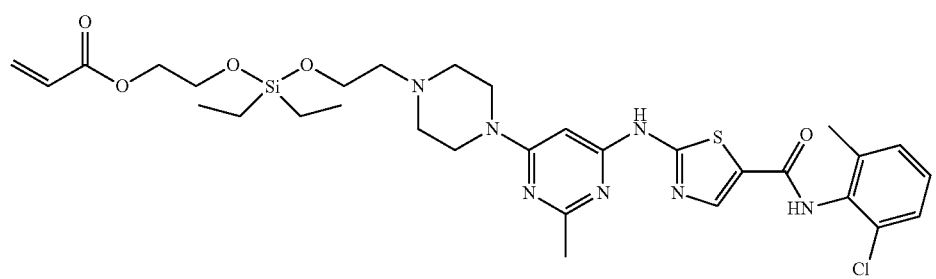

Chemical Formula: $C_{31}H_{42}ClN_7O_5SSi$
Exact Mass: 687.2426
Molecular Weight: 688.3126

In a dry 20 mL scintillation vial equipped with a magnetic stir bar (purged with N2), dasatinib (0.500 g, 1.024 mmol, 1.0 eq.), 4-dimethylaminopyridine (4-DMAP) (0.1245 g, 1.019 mmol, 1.0 eq.) and imidazole (0.4860 g, 7.139 mmol, 7.0 eq.) were dissolved in 12 mL of anhydrous DMF. After 30 minutes dichlorodiethyl silane (0.4807 g, 3.059 mmol, 3.0 eq.) was added to the mixture. After 2.5 hours hydroxyethyl acrylate (0.592 g, 5.098 mmol, 5.0 eq.) was added and allowed to react for an additional 1 hour.

The reaction mixture was diluted with ethyl acetate (150 mL) and washed with saturated NaCl (150 mL) to remove the DMF. The organic layer was removed by rotary evaporation in vacuo, and the product was isolated by column chromatography. The product was eluted using a mixture of hexanes, ethyl acetate and methanol (7:2:1). The resulting solid was dried in vacuo. Yield: 122.1 mg (17.3%), white solid. $^1$H NMR (400 MHz, DMSO-d$_6$):δ=0.58 (q, 4H, J=8.04 Hz), 0.91 (t, 6H, J=7.88 Hz), 2.23 (s, 3H), 2.40 (s, 3H), 2.62* (m, 6H), 3.44 (s, 1H), 3.49 (s, 4H), 3.78 (t, 2H, J=6.0 Hz), 3.90 (m, 2H), 4.20 (m, 2H), 5.96 (dd, 1H, J=1.56 Hz, 10.28 Hz), 6.04 (s, 1H), 6.19 (dd, 1H, J=10.32 Hz, 17.26 Hz), 6.34 (dd, 1H, J=1.56 Hz, 17.26 Hz), 7.28 (m, 2H), 7.39 (m, 1H), 8.21 (s, 1H), 9.87 (s, 1H), 11.46 (s, 1H). $^{13}$C NMR (150 MHz DMSO-d$_6$):δ=3.041, 3.315, 6.383, 6.449, 18.371, 25.640, 43.639, 49.844, 52.819, 59.777, 59.817, 59.997, 60.313, 65.442, 82.701, 125.703, 127.060, 128.216, 128.248, 129.074, 131.765, 132.477, 133.568, 138.868, 140.887, 157.016, 159.976, 162.410, 162.651, 165.195, 165.523. HR-MS (m/z) calcd for $C_{31}H_{42}ClN_7O_5SSi$, [M]$^+$=687.2426, [M+H]$^+$=688.2426, [M+Cs]$^+$=820.1480; found [M+H]$^+$ m/z=688.2504+5.9 ppm, [M+Cs]+=820.1480+5.3 ppm. (*Determined using MeOD-d$_4$)

b. Diisopropyl ABS of Dasatinib (iPr-DAS)

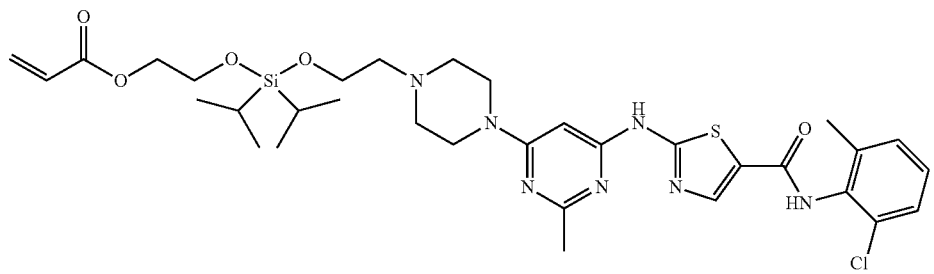

Chemical Formula: $C_{33}H_{46}ClN_7O_5SSi$
Exact Mass: 715.2739
Molecular Weight: 716.3657

In a dry 20 mL scintillation vial equipped with a magnetic stir bar (purged with N₂), dasatinib (0.500 g, 1.024 mmol, 1.0 eq.), 4-dimethylaminopyridine (4-DMAP) (0.124 g, 1.014 mmol, 1.0 eq.) and imidazole (0.486 g, 7.139 mmol, 7.0 eq.) were dissolved in 15 mL of anhydrous DMF. After 15 minutes, dichlorodiisopropyl silane (0.568 g, 3.067 mmol, 3.0 eq.) was added to the mixture. After 45 minutes hydroxyethyl acrylate (HEA) (0.594 g, 5.11 mmol, 5.0 eq.) was added and allowed to react for an additional 45 minutes. The reaction mixture was diluted with ethyl acetate (150 mL) and washed with saturated NaCl (150 mL) to remove the DMF. The organic layer was removed by rotary evaporation in vacuo, and the product was isolated by column chromatography. The product was eluted using a mixture of hexanes, ethyl acetate and methanol (7:2:1). The resulting solid was dried in vacuo. Yield: 161.8 mg (22.1%), white solid. ¹H NMR (400 MHz, DMSO-$d_6$):δ=0.99 (s, 14H), 2.23 (s, 3H), 2.40 (s, 3H), 2.65*(m, 6H), 3.49 (s, 4H), 3.84 (t, 2H, J=6.04 Hz), 3.96 (m, 2H), 4.23 (m, 2H), 5.96 (dd, 1H, J=1.6 Hz, 10.28 Hz), 6.04 (s, 1H), 6.18 (dd, 1H, J=10.28 Hz, 17.34 Hz), 6.34 (dd, 1H, J=1.6 Hz, 17.28 Hz), 7.27 (m, 2H), 7.39 (m, 1H), 8.21 (s, 1H), 9.87 (s, 1H), 11.46 (s, 1H). ¹³C NMR (150 MHz DMSO-$d_6$):δ=11.397, 17.132, 17.137, 18.317, 25.592, 43.641, 52.837, 59.755, 60.643, 60.703, 65.341, 82.645, 125.701, 127.023, 128.131, 128.244, 129.042, 131.666, 132.440, 133.521, 138.830, 140.830, 156.952, 159.924, 162.388, 162.564, 165.178, 165.477. HR-MS (m/z) calcd for $C_{33}H_{46}Cl_1N_7O_5SSi$, $[M]^+$=715.2739, $[M+Na]^+$=738.2636; found $[M+Na]^+$ m/z=738.2637+2.8 ppm, $[M+Cs]^+$=848.1793+4.9 ppm. (*Determined using MeOD-$d_4$)

c. Di-tertbutyl ABS of Dasatinib (tBu-DAS)

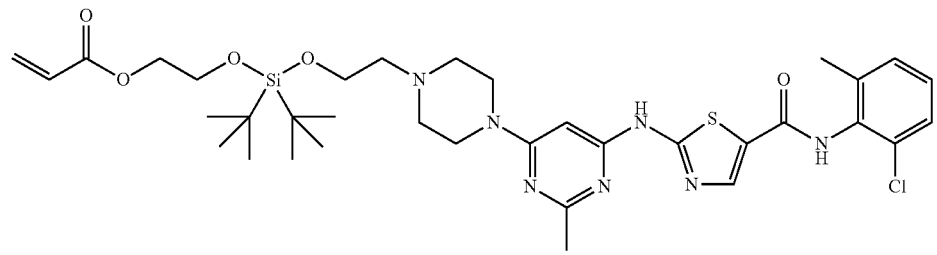

Chemical Formula: $C_{35}H_{50}ClN_7O_5SSi$
Exact Mass: 743.3052
Molecular Weight: 744.4189

In a dry 20 mL scintillation vial equipped with a magnetic stir bar (purged with N₂), dasatinib (0.500 g, 1.024 mmol, 1.0 eq.), 4-dimethylaminopyridine (4-DMAP) (0.1245 g, 1.019 mmol, 1.0 eq.) and imidazole (0.4860 g, 7.139 mmol, 7.0 eq.) were dissolved in 12 mL of anhydrous DMF. After 10 minutes, ditertbutylsilylbis(trifluoromethanesulfonate) (1.34 g, 3.042 mmol, 3.0 eq.) was added to the mixture. After 45 minutes hydroxyethyl acrylate (HEA) (0.592 g, 5.095 mmol, 5 eq.) was added and allowed to react for an additional 45 minutes. The reaction mixture was diluted with ethyl acetate (150 mL) and washed with saturated NaCl (150 mL) to remove the DMF. The organic layer was removed by rotary evaporation in vacuo, and the product was isolated by column chromatography. The product was eluted using a mixture of hexanes, ethyl acetate and methanol (7:2:1). The resulting solid was dried in vacuo. Yield: 167.1 mg (22%), white solid. ¹H NMR (400 MHz, DMSO-$d_6$):δ=0.97 (s, 18H), 2.23 (s, 3H), 2.40 (s, 3H), 2.66*(m, 6H), 3.49 (s, 4H), 3.94 (t, 2H, J=5.96 Hz), 4.05 (m, 2H), 4.24 (m, 2H), 5.96 (dd, 1H, J=1.56 Hz, 10.28 Hz), 6.04 (s, 1H), 6.17 (dd, 1H, J=10.32 Hz, 17.26 Hz), 6.34 (dd, 1H, J=1.56 Hz, 17.24 Hz), 7.27 (m, 2H), 7.39 (m, 1H), 8.21 (s, 1H), 9.88 (s, 1H), 11.46 (s, 1H). ¹³C NMR (150 MHz DMSO-$d_6$):δ=18.378, 20.783, 25.640, 27.580, 43.681, 52.911, 59.923, 61.683, 65.398, 82.697, 125.734, 127.057, 128.204, 128.279, 129.068, 131.656, 132.482, 133.575, 138.866, 140.881, 157.001, 159.980, 162.405, 162.633, 165.188, 165.469. HR-MS (m/z) calcd for $C_{35}H_{50}ClN_7O_5SSi$, $[M]^+$=743.3052, $[M+Na]^+$=766.2949, $[M+Cs]^+$=876.2106; found $[M+Na]^+$ m/z=766.2950−2.0 ppm, $[M+Cs]^+$=876.2106+3.7 ppm. (*Determined using MeOD-$d_4$).

17. ABS of Cisplatin a. Cisplatin Silyl Pro-drugs

Cisplatin is a hydrophilic drug that is water soluble. Because of its hydrophilic nature, it cannot easily be incorporated into polymer particle compositions. For example, it is not miscible with the PLGA polymers, which are hydrophobic. One difficulty is achieving a homogeneous delivery sheet with high loading of cisplatin in the PLGA. Any drug associated with the particle is lost quickly in a burst release profile.

Cisplatin is more miscible in PEG hydrogel. However, because it is a small molecule, it is difficult to retain drug in the PEG particle and it quickly leaks out over time. These problems can be overcome by modifying cisplatin, or any hydrophilic small molecule, agent, drug, biologic or fragment thereof, etc. to be more compatible with PLGA or PEG particle systems.

One method is to attach a lipophilic molecule to the cisplatin to make it more hydrophobic and more compatible with PLGA. By changing the lipophilicity of the cisplatin, it would be possible to cast homogeneous delivery sheets with higher loading of drug. The attachment of the lipophilic entity would be through the cleavable silyl ether. Under acidic condition the lipid molecule would be cleaved and the drug returned to its native state. PLGA particles with cisplatin encapsulated will have higher drug loading with improved release profiles.

A second method is directed to a co-polymerization of the drug into the PEG particle through the acid degradable silyl ether linkage. In the structure below, X represents the covalently-bound residue of the drug. The acrylate group of the structure below can be used to polymerize the silyl ether pro-drug into to the particle.

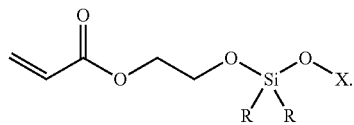

b. Starting Material Synthesis

In one embodiment, the Hard System (e.g. PLGA) involves conversion of alcohols into lipid chains This allows for noncovalent incorporation of hydrophobic cisplatin silyl ether pro-drugs into PRINT® nanoparticles, particularly into PLGA/PLLA particles. As discussed above, the hydrophilic nature of Cisplatin requires that it be made more hydrophobic for effective incorporation into the PLGA particle.

SCHEME 29

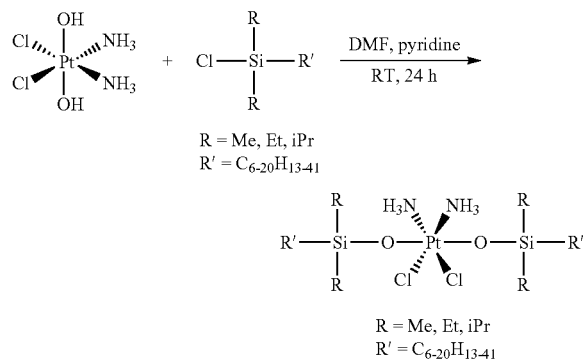

In one embodiment, the Soft System (e.g. Hydrogels) involves conversion of alcohols into polymerizable acrylates. This allows for covalent incorporation of cisplatin silyl ether pro-drugs into PRINT® nanoparticles, preferably a PEG hydrogel.

SCHEME 30

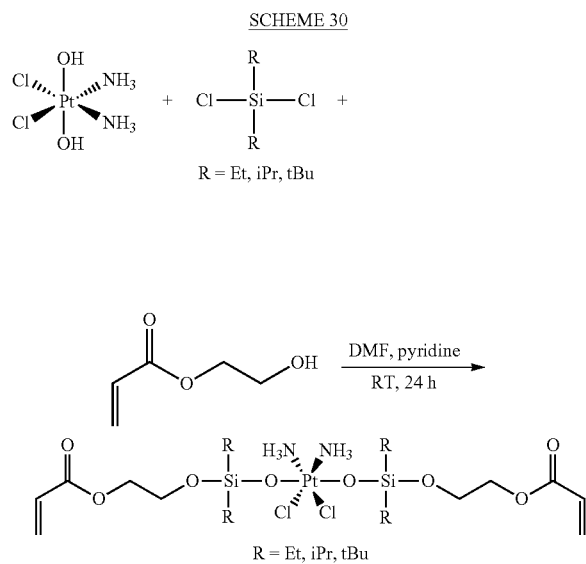

SCHEME 31

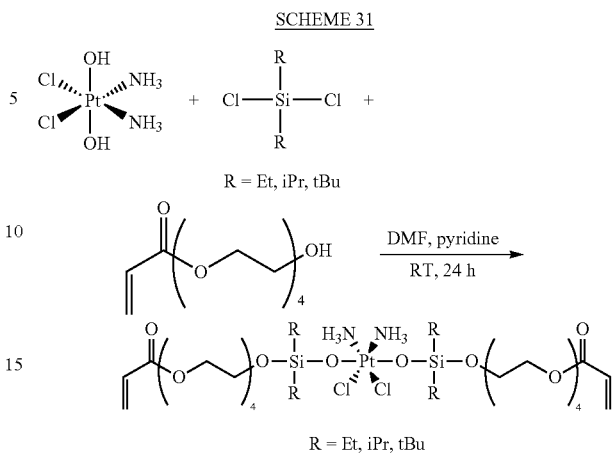

c. Targeted Release of Drug

SCHEME 32

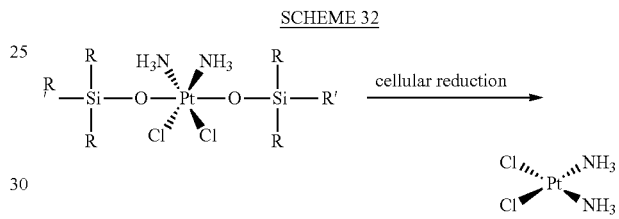

18. ABS Pro-drugs via Covalent Carboxyl Linkage

The following examples depict the conversion of carboxylic acid/ester moieties of a drug into polymerizable asymmetric silyl acrylates. This modification provides a chemical handle for covalent incorporation of silyl ester pro-drugs into PRINT® nanoparticles.

a. Ibuprofen

SCHEME 33

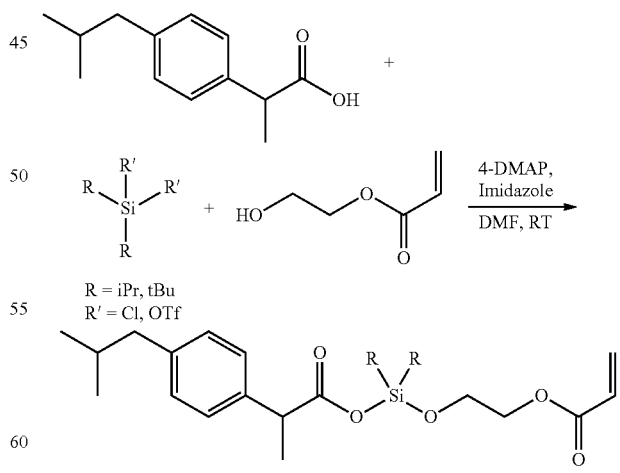

$^1$H NMR and HR-MS data confirm the preparation of $^i$Pr and $^t$Bu silyl ester ibuprofen pro-drugs having the following structures:

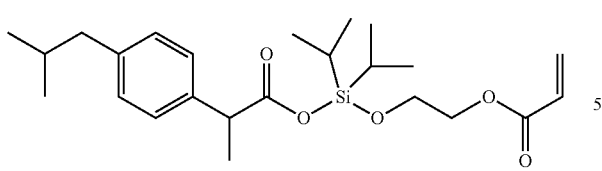

Chemical Formula: C$_{24}$H$_{38}$O$_5$Si
Exact Mass: 434.2499
Molecular Weight: 434.6410

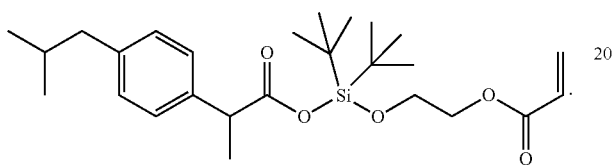

Chemical Formula: C$_{26}$H$_{42}$O$_5$Si
Exact Mass: 462.2802
Molecular Weight: 462.6942 b. Methotrexate

The synthetic strategy above will be used to synthesize pro-drugs of chemotherapeutics containing at least one carboxylic acid moiety. Methotrexate is a class of anti-metabolite drugs used in the treatment of cancer and auto immune diseases. Schemes 31, 32 and 33 depict a proposed synthesis of a silyl ester prodrug of methotrexate using at least one available carboxyl group of methotrexate.

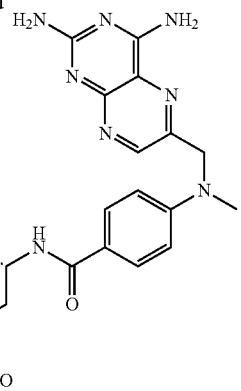

R= Et, iPr, tBu

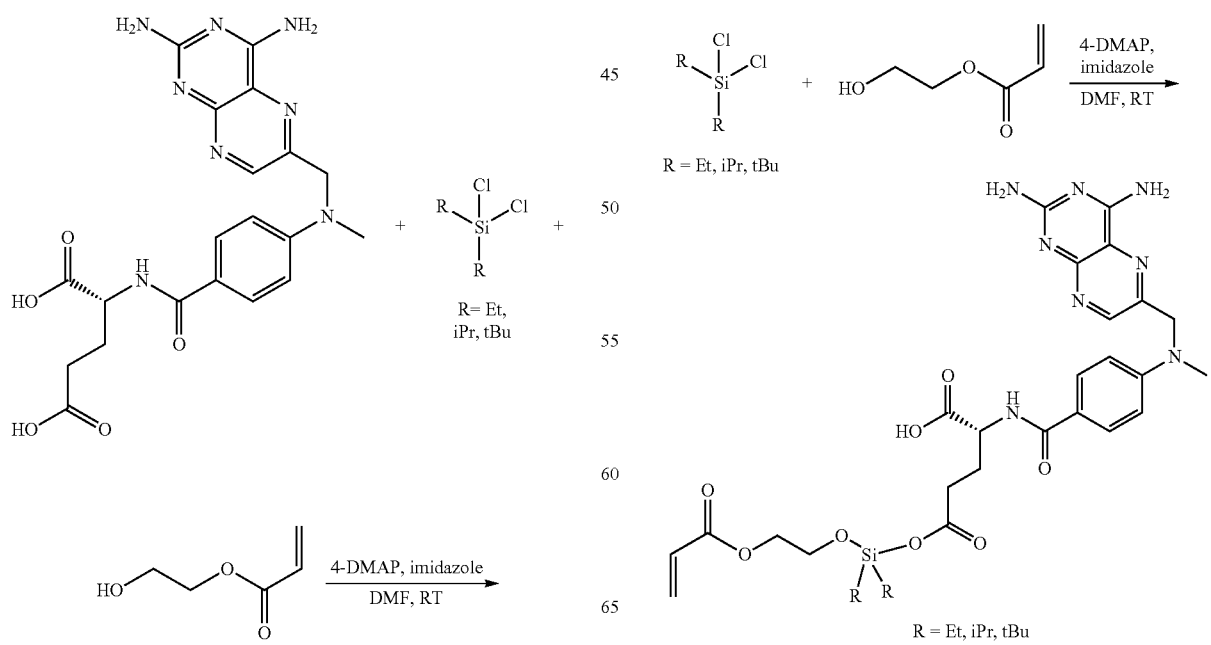

SCHEME 36

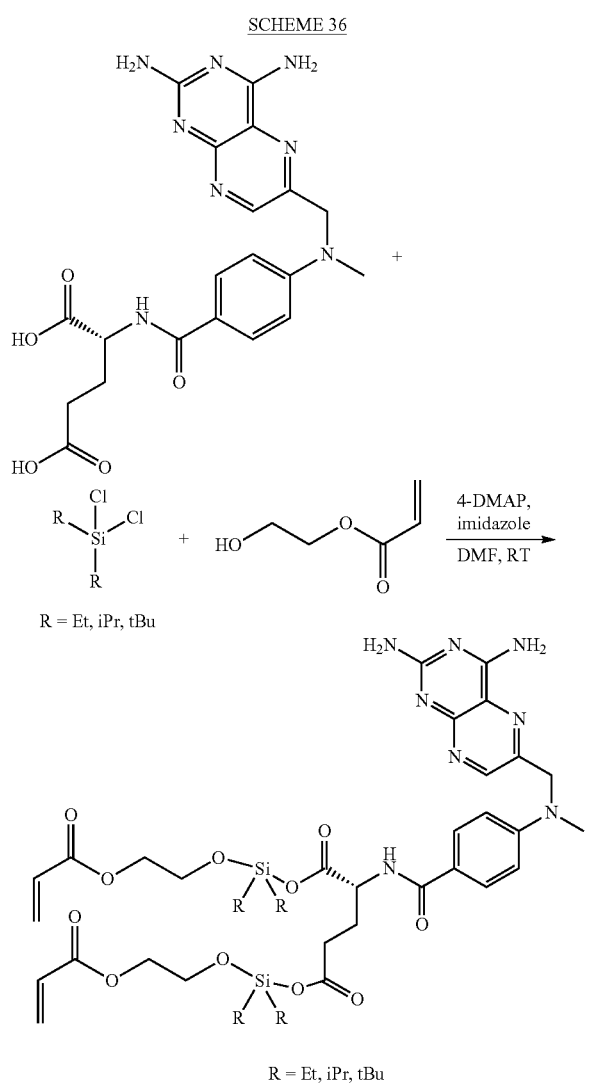

19. General Synthetic Routes for Preparing ABS Prodrugs a. Drugs Containing an Alcohol Moeity

SCHEME 37

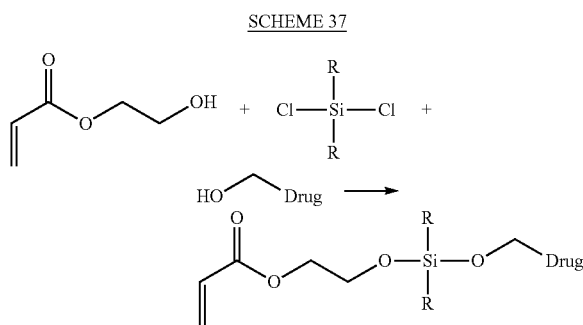

In embodiments, modification of the alcohol with a dichlorodialkyl silane yielded a monochloro-silane intermediate, which was rapidly converted to a polymerizable monomer, for example, with the addition of hydroxyl ethyl acrylate (HEA). In this non-limiting example, attachment of the polymerizable HEA unit provided the chemical handle required for photopolymerization during the fabrication of PRINT particles.

b. Drugs Containing an Amine Moeity

SCHEME 38

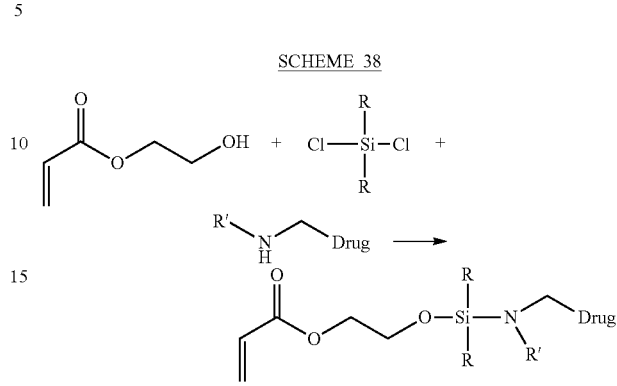

20. Biodegradation of PEG hydrogel Particles, Silyl Ether Pro-drug Encapsulation, Release, and In Vitro Analysis The hydrolysis of PEG hydrogel particles under physiologically relevant conditions are shown in this example to estimate the fate of the particles in vivo. The parameters examined were the amount of photoinitiator, the degradation rates of the bulk material compared to the particles and the degradation conditions. Data is shown in Tables 2 and 3 below.

The samples were degraded with the following protocol:
1) A ~20 mg/ml sample of hydrogel was placed in a scintillation vial.
2) The sample was immersed in 3 mL (excess buffer to accommodate swelling) of pH 5 buffer.
3) A stir bar was added and the hot plate set to 900 rpm and temperature of 37C.
4) A temperature probe and beaker of water was used to control temperature fluctuation.
5) 200 ul aliquots were collected at 1 hr, 4 hrs, 1 day, 3 weeks, and 6 weeks.

Using GPC and visual inspection, the bulk samples were shown to degrade to polyacrylic acid and short PEG oligomer (1-10 units in length). The higher the photoinitiator concentration, the more quickly the bulk samples degraded. The higher amounts of photoinitiator resulted in shorter chain lengths and fewer entangled units resulting in moieties which should be able to be renally cleared. It is of note that renal clearance is typically between a molecular weight of 30-50K.

HP4A—Hydroxy PEG Acrylate with 4 ethylene glycol units

TABLE 2

| Bulk sample composition | |
|---|---|
| Amount of HPA (mg) | Amount of Photoinitiator (mg) |
| 99.5 | 0.5 |
| 99.0 | 1.0 |

TABLE 2-continued

Bulk sample composition

| Amount of HPA (mg) | Amount of Photoinitiator (mg) |
|---|---|
| 98.5 | 1.5 |
| 98.0 | 2.0 |

Particles: 1 micron, 200×200 nm, 80×320

TABLE 3

Pre-particle Solution Composition:

| Amount of HPA (mg) | Amount of Photoinitiator (mg) | PEG-DA (mg) |
|---|---|---|
| 89.5 | 0.5 | 10 |
| 89.0 | 1.0 | 10 |
| 88.5 | 1.5 | 10 |
| 88.0 | 2.0 | 10 |

21. Degradation of ABS of Diisopropyl Gencitabine Silyl Ether (iPr-GEM)

A model degradation of an ABS pro-drug of gemcitabine attached via a di-isopropyl silyl ether linkage (iPr-GEM) was conducted. The results show that the molecule is acid sensitive and reverts back to the original starting materials. The HPLC chromatograms of this experiment, shown in FIGS. 3A-D, show that the starting material, HEA and camptothecin (CPT), where converted to the Et-CPT ABS pro-drug in high purity. Upon exposure to acid the silyl ether linkage degraded to yield both unmodified camptothecin and HEA The ABS pro-drugs of gemcitabine were separately incorporated into "Trojan Horse" nanoparticles using particle replication in nonwetting templates a particle fabrication technique known as PRINT. PRINT is a top-down technique used to manufacture microparticles and nanoparticles with well-defined shape and size. See, US 2009/0028910; US 2009/0061152; WO 2007/024323; US 2009/0220789; US 2007/0264481; US 2010/0028994; US 2010;0196277; WO 2008/106503; US 2010/0151031; WO 2008/100304; WO 2009/041652; PCT/US2010/041797; US 2008/0181958; WO 2009/111588; and WO 2009/132206. Cylindrical nanoparticles with dimensions of 200 nm×200 nm where fabricated with 20 wt % of the ABS pro-drug, and the remaining bulk of the particle was comprised of a crosslinker (PEGi000diacrylate), a positive charge agent (aminoethyl methacrylate-hydrochloride, AEM-HCl), a fluorescent dye (FOA) and a photo-initiator (HCPK). Each particle fabricated with a gemcitabine ABS pro-drug had a typical size range of 280±10 nm and a zeta potential of 20±5.

Figure 4:
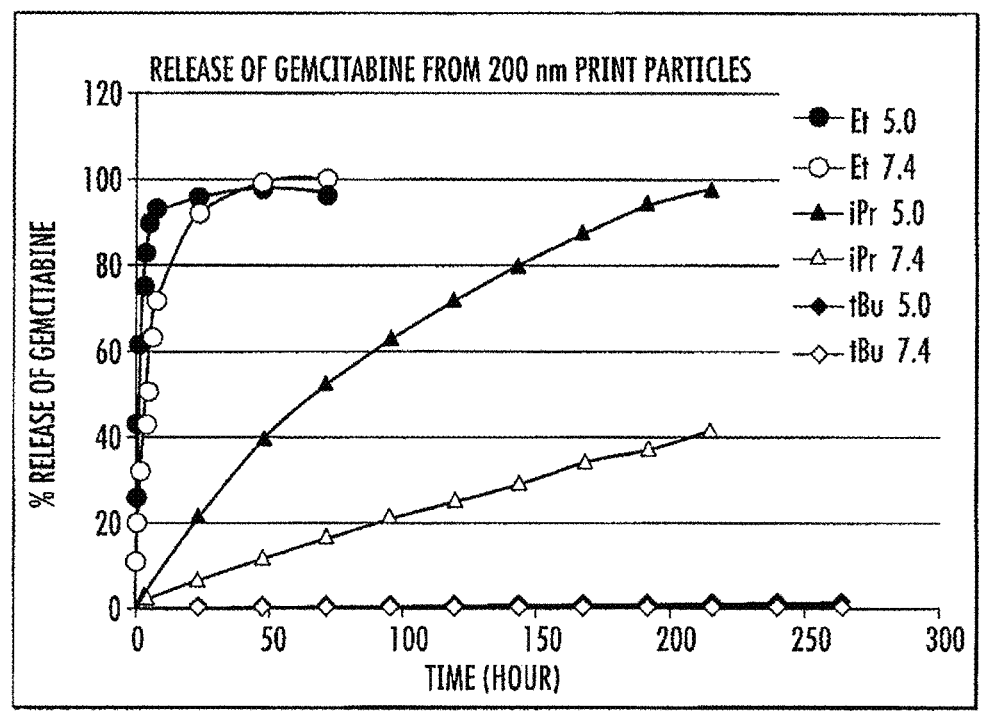
FIG. 4 depicts a percent release of gemcitabine vs time for 200 nm×200 nm PRINT particles fabricated from Et-GEM (circle), iPr-GEM (triangle), and tBu-GEM (diamond) ABS pro-drugs. Closed symbols represent particles degraded at pH 5.0 and open symbols represent particles degraded at pH 7.4.

A quantitative analysis of gemcitabine release was performed on particles fabricated with Et-GEM, iPr-GEM and tBu-GEM. The particles were degraded in solutions buffered at pH 5.0 and pH 7.4 and maintained at 37° C. Aliquots of the solution were removed, filtered, and the supernatant was injected into an HPLC. The plot of gemcitabine release versus time for each particle showed an increase in the rate of drug release when the particles were degraded under acidic conditions (FIG. 4). Additionally, as the steric bulk around the silicon atom increased the rate of drug release decreased. For example, data on half-life release rates of different particles are shown (t-Bu GEM was extrapolated) in Table 4 below. This demonstrates that the particles can release gemcitabine efficiently and the rate of release can be tuned based on the substituents on the silicon atom. Furthermore, particles degraded under physiological conditions (pH 7.4) showed a significantly slow rate of release when compared to the particles degraded at pH 5.0.

TABLE 4

Degradation half-lives ($t_{1/2}$) and relative rates of release from 200 nm × 200 nm PRINT particles.

| | Ethyl-GEM | | Isopropyl-GEM | | t-Butyl-GEM | |
|---|---|---|---|---|---|---|
| | | | pH | | | |
| | 5.0* | 7.4* | 5.0* | 7.4* | 5.0† | 7.4* |
| $t_{1/2}$ (h) | 1.36 | 3.91 | 68.5 | 274 | 6995 | 13055 |
| Rel. rate | 1 | 2.88 | 50.4 | 201 | 5143 | 9599 |

*Fitted to an exponential growth.
†Linear Fit

Intracellular degradation of the gemcitabine ABS pro-drugs was monitored by cell viability experiments. This was accomplished by separately dosing all three particle sets (Et-GEM, iPr-GEM, and tBu-GEM) onto the LnCAP cell line and comparing the cell viability against commercially available gemcitabine.

22. Composition and In Vitro Efficacy of Particles a. Composition

Figure 5:
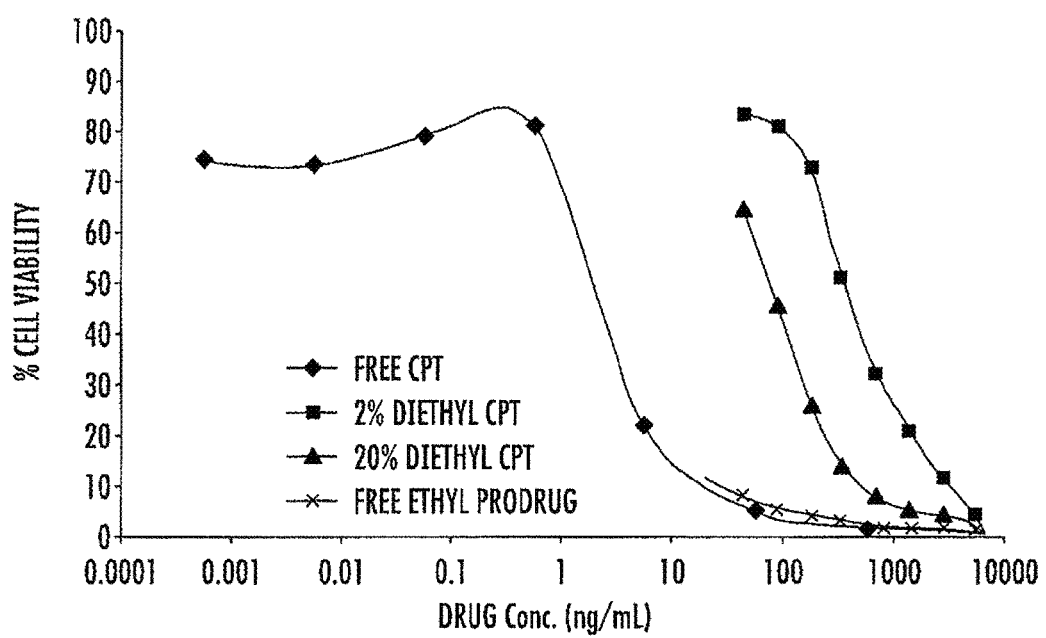
FIG. 5 depicts a percent viability of H460 cells against PRINT particles containing 2 wt % and 20 wt % ABS pro-drug. The particles were compared against free camptothecin and free CPT-ABS pro-drug.

PRINT particles where fabricated with a variety of compositions using a drug loading between 2 and 20 percent by weight. The effect of varying concentrations of CPT loading is depicted in FIG. 5. A 10-fold increase of CPT (20%) resulted in a 10-fold increase in cellular toxicity. Due to facile fabrication of particles containing 20 wt %, and the subsequent increase in cellular toxicity, 20 wt % drug loading was selected as a standard particle load.

Cylindrical nanoparticles with dimensions of 200 nm×200 nm were fabricated with the ABS pro-drug according to PRINT methods, and the remaining bulk of the particle was comprised of a crosslinker (PEGi000diacrylate), a positive charge agent (aminoethyl methacrylate-hydrochloride, AEM-HCl), a fluorescent dye (fluorescein o-acrylate, FOA) and a photo-initiator (1-hydroxycyclohexyl phenyl ketone, HCPK).

TABLE 5

Camptothecin Particle Compositions

| | Et-CPT-2 | Et-CPT-20 |
|---|---|---|
| PEG$_{1000}$DiAcrylate | 76 | 58 |
| AEM-HCl | 20 | 20 |
| FOA | 1 | 1 |
| HCPK | 1 | 1 |
| Pro-Drug | 2 | 20 |
| | 100 | 100 |
| Theor. wt % of Camptothecin | (1.27) | (12.7) |

TABLE 6

Gemcitabine Particle Compositions

| | Et-GEM | iPr-GEM | tBu-GEM | Blanks |
|---|---|---|---|---|
| PEG$_{1000}$DiAcrylate | 58 | 58 | 58 | 78 |
| AEM-HCl | 20 | 20 | 20 | 20 |

TABLE 6-continued

Gemcitabine Particle Compositions

|  | Et-GEM | iPr-GEM | tBu-GEM | Blanks |
|---|---|---|---|---|
| FOA | 1 | 1 | 1 | 1 |
| HCPK | 1 | 1 | 1 | 1 |
| Pro-Drug | 20 | 20 | 20 | 0 |
|  | 100 | 100 | 100 | 100 |
| Theor. wt % of Gemcitabine | (11.36) | (10.70) | (10.14) | (0.00) | b. Cell Viability Assay

Figure 6:
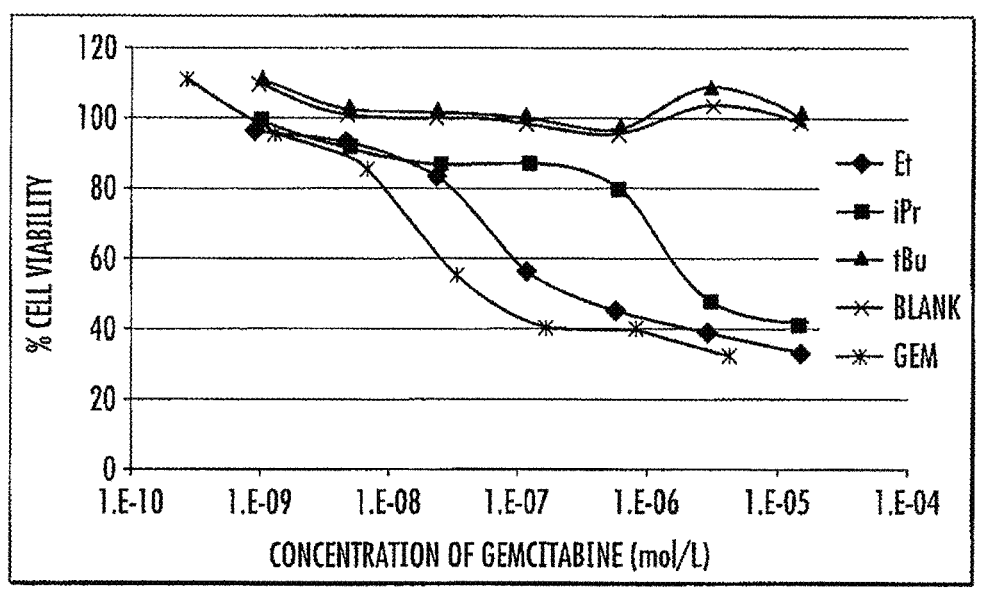
FIG. 6 shows the data from a cell viability assay (Cell-Titer-Glo) of 200 nm×200 nm PRINT particles fabricated from Et-GEM (Diamond), iPr-GEM (square), and tBu-GEM (triangle) ABS pro-drugs versus blank particles (X) and free gemcitabine (*). The assay was performed using LnCAP cells.
Figure 7A:
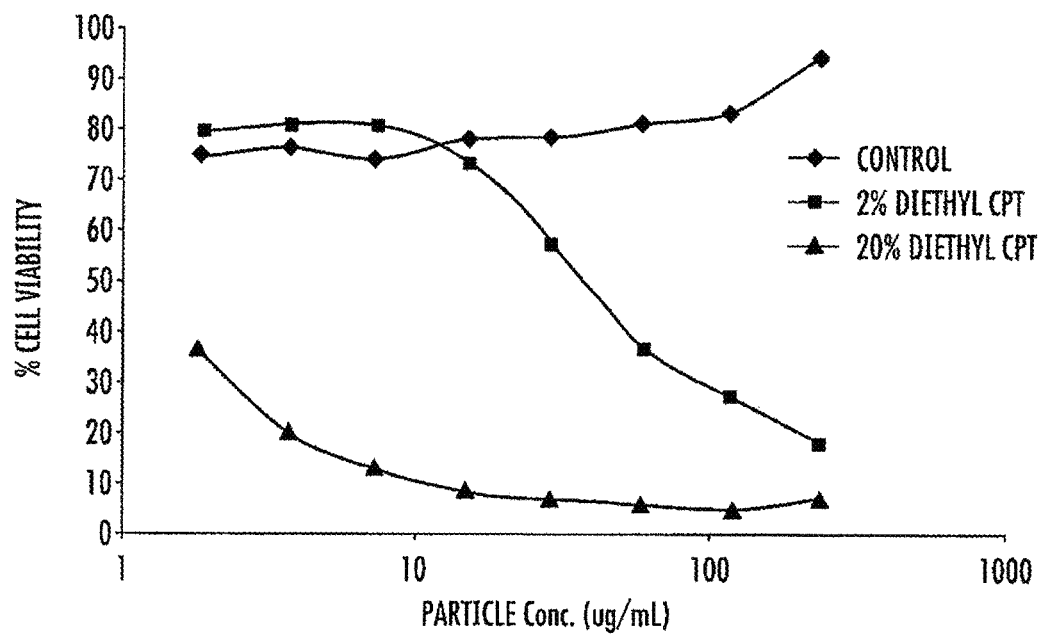
FIGS. 7A-B depict % cell viability versus particle concentration (μg/mL) containing ABS (diethyl) CPT (camptothecin) or ABS (di-iPr) CPT.
Figure 7B:
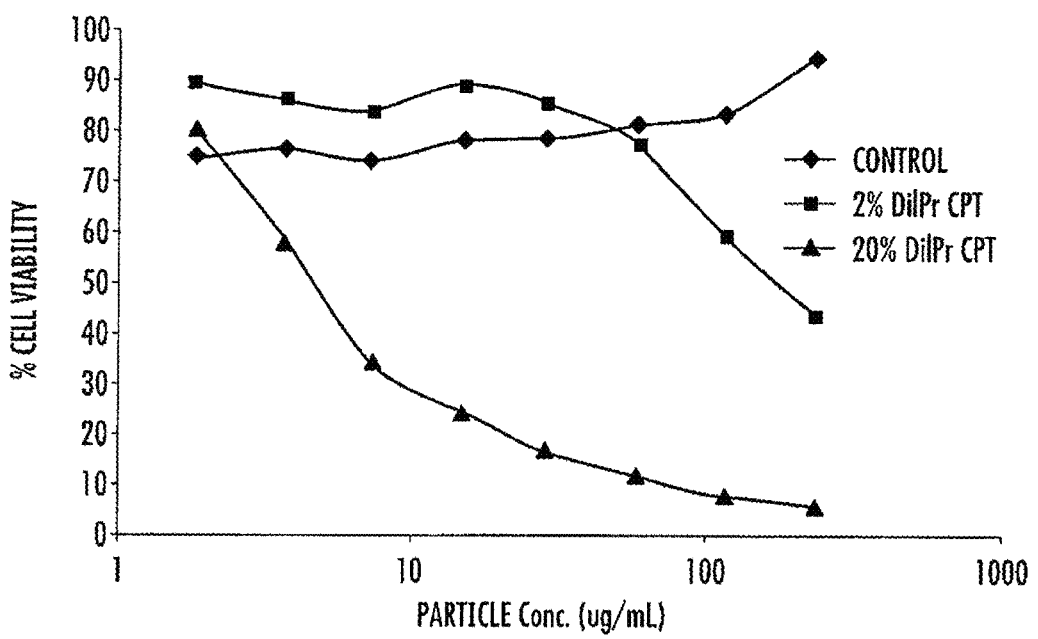
Figure 9:
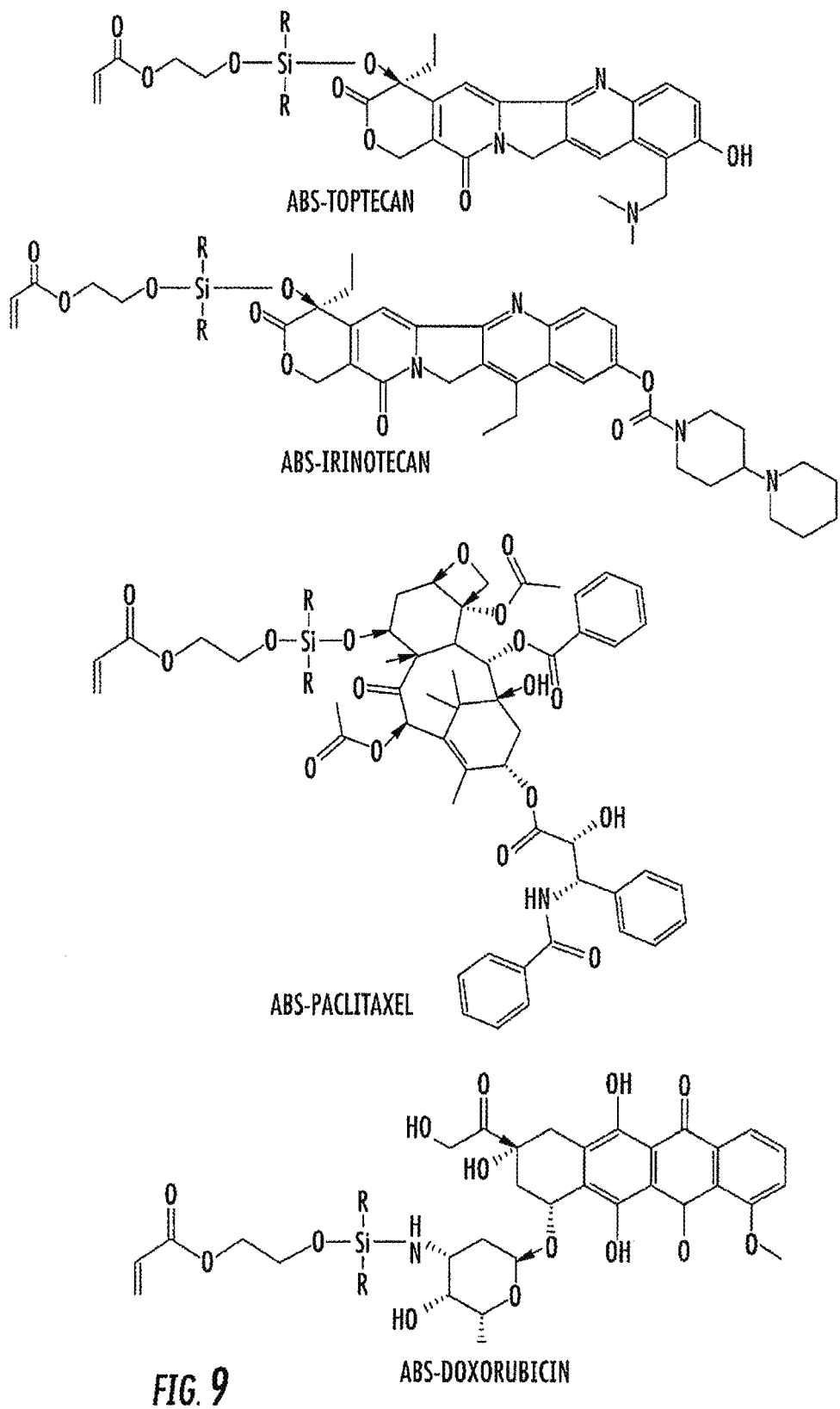
Figure 11:
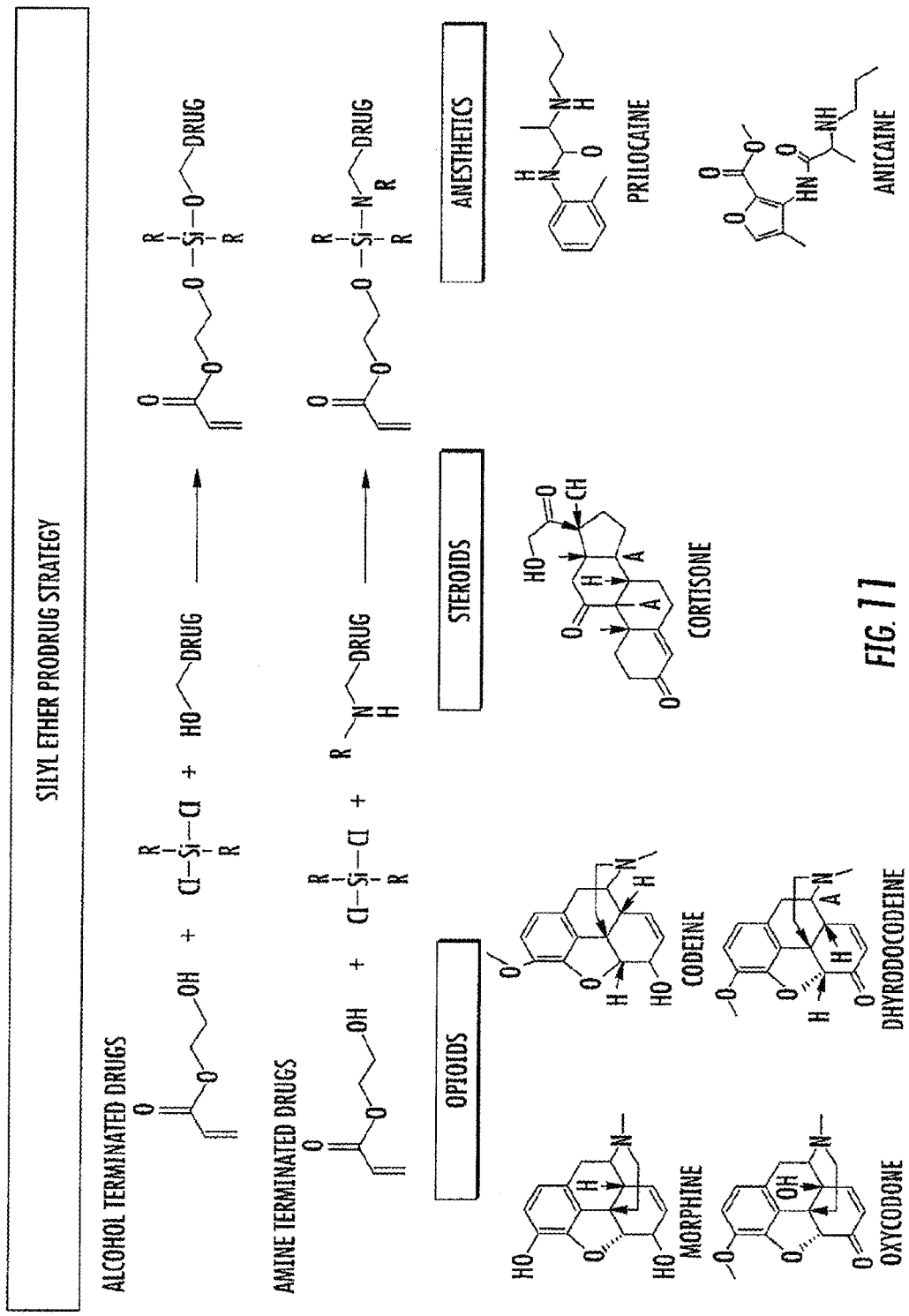

The cytotoxicity of each particle was determined using a CellTiter-Glo luminescent cell viability assay after a 72 hour incubation time (FIG. 6).

The data from the cell viability assay show that particles containing Et-GEM or iPr-GEM performed as well, if not better, than the free gemcitabine. In fact, particles containing the Et-GEM ABS pro-drug actually outperformed the free gemcitabine throughout the in vitro cell assay. This superior efficacy may be due to rapid particle internalization of the positively charged particles, and rapid release of the gemcitabine upon exposure to an acidic cellular compartment. Remarkably, the particles fabricated from the tBu-GEM ABS pro-drug showed almost negligible amounts of cytotoxicity, even at extremely high drug concentrations. This further establishes the tenability of the disclosed ABS pro-drugs. Each can be tuned independently to degrade rapidly, moderately, or even not at all.

Asymmetric bifunctional silyl ether pro-drugs were synthesized and analyzed as potential materials for controlled drug delivery in nanoparticles. Using one-step synthesis, numerous pro-drugs from the chemotherapeutics camptothecin, dasatinib, and gemcitabine were prepared. These ABS pro-drugs were placed under acidic conditions, such as those found under physiological conditions, and subsequent to degradation of the reversible covalent linkage(s), the pro-drug reverted back to the original active form of the chemotherapeutic. The ABS pro-drugs of gemcitabine were incorporated into 200 nm PRINT nanoparticles and showed controlled and tunable released of gemcitabine. The rate of release increased as the steric bulk of the substituent on the Si atom decreased; Rate of Release: Et-GEM>iPr-GEM>>tBu-GEM). It was found that the release of the particle-bound drug was accelerated upon exposure to acidic condition similar to those found in the cellular endocytic cycle. These ABS pro-drugs can be incorporated into nanoparticles and medical devices capable of releasing drugs in a controlled and tunable fashion.

c. Particle Fabrication

A monomer solution (5% in dimethylformamide (DMF)) consisting of the following components is prepared as shown in Table 7.

TABLE 7

| Monomer | No Prodrug (Wt %) | With Prodrug (Wt %) |
|---|---|---|
| PEG$_{1000}$ dimethacrylate | 78 | 58 |
| 2-Aminoethyl methacrylate hydrochloride | 20 | 20 |
| Fluorescein o-acrylate | 1 | 1 |
| 1-Hydroxycyclohexyl phenyl ketone | 1 | 1 |
| Diisopropyl gemcitabine prodrug | 0 | 20 |

A monomer film is cast upon a sheet of poly(ethylene terephthalate) (PET) with a mayer rod (#2) and dried with heat. The PET sheet (monomer film) and mold are laminated under pressure and then delaminated. The mold is laminated with a fresh sheet of PET and then exposed to UV irradiation for 4 minutes. The mold is removed, transferring particles onto the PET. Particles are collected from the PET by gently moving cold Dulbecco's phosphate buffered saline (DPBS) along the sheet with a cell scraper. The harvested particles are washed twice with cold DPBS by centrifugation.

d. Ligand Conjugation to Particles

The particles are washed once with DMF by centrifugation and then resuspended in DMF. Particles are reacted with NHS-PEG$_{5000}$-biotin in DMF in the presence of pyridine for 2 h. The particles are then reacted with acetic anhydride to quench unreacted amines on the particle surface. The particles are washed once with DMF and twice with DPBS by centrifugation and then resuspended in DPBS. To attach avidin, particles in DPBS are shaken with UltraAvidin for 1 h, followed by two washings with DPBS by centrifugation. To conjugate a ligand (either OKT9- or IgG-biotin), particles are reacted with the ligand in DPBS for 30 min at room temperature and then overnight at 4° C. Particles are washed with DPBS by centrifugation to remove unbound ligand.

e. In Vitro Targeting

H460 cells, a lung cancer cell line with high expression of the transferrin receptor (TfR), were incubated first with varying concentrations of free OKT9 for 1 h at 37° C.

Figure 12:
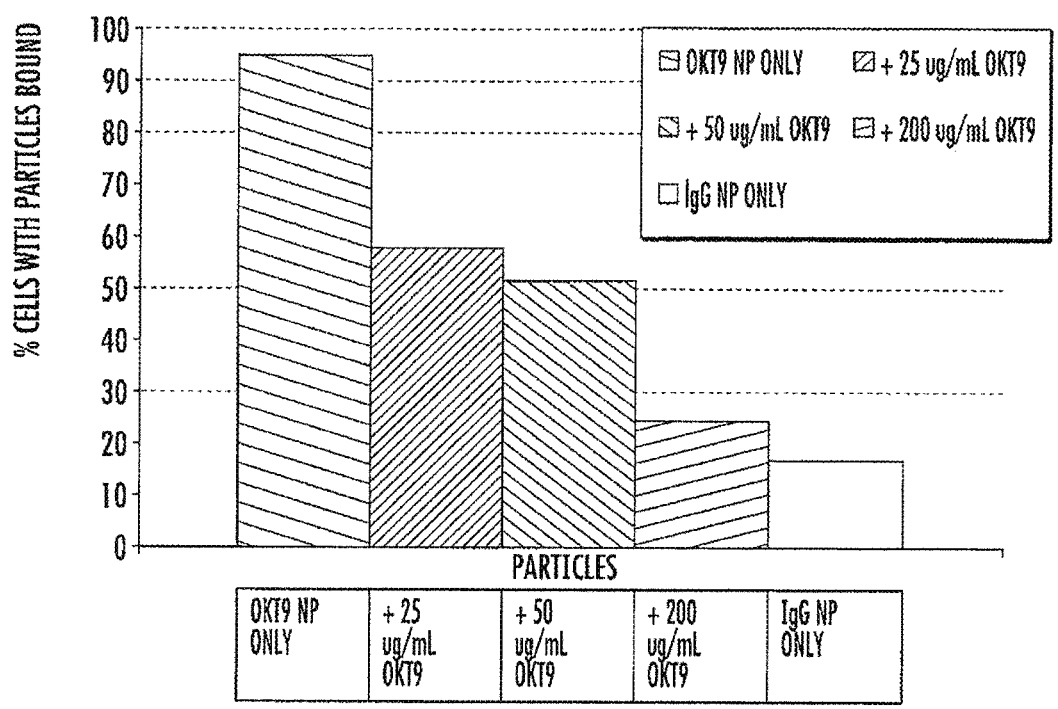
FIG. 12 depicts in vitro selective targeting of OKT9-targeted particles in H460 cells that can be inhibited by competitive binding from free ligand.

Targeted particles were then incubated with the cells and free OKT9 for 4 h at 37° C. Samples were analyzed by flow cytometry. As seen in FIG. 12, without competing free ligand, OKT9-targeted particles bound to the cellular surface and were internalized. However, in the presence of free ligand, OKT9-targeted particles were unable to bind to cells as the TfR on the cellular surface were already bound by free ligand. Increasing concentrations of free OKT9 inhibited greater binding and internalization of OKT9-targeted particles, competitively binding with the TfR. The results suggest that OKT9-targeted particles selectively bind the TfR and internalize into H460 cells via receptor-mediated endocytosis.

Figure 13:
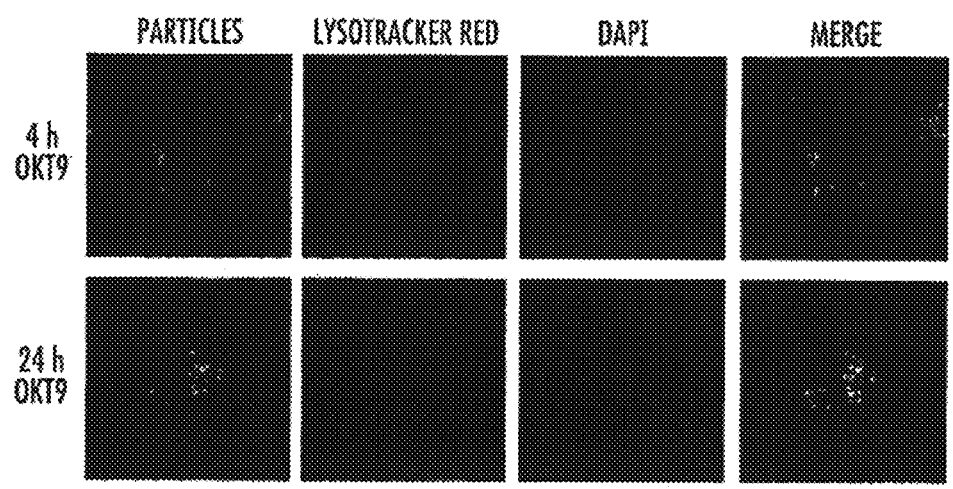
FIG. 13 depicts the selective targeting of OKT9-targeted particles observed by confocal microscopy. At 4 h, binding and some internalization of OKT9-targeted particles is observed, while increased internalization and colocalization is seen at 24 h. IgG-targeted particles do not bind and internalize into the cells.

Selective targeting of OKT9-targeted particles was observed by confocal microscopy as shown in FIG. 13. Targeted particles were incubated with H460 cells for 4 and 24 h. The cellular nucleus was stained with 4',6-diamidino-2-phenylindole (DAPI), and acidic vesicles within the cell were stained with Lysotracker Red; particles were labeled with fluorescein o-acrylate. At 4 h, binding and some internalization of OKT9-targeted particles is observed, while increased internalization and colocalization is seen at 24 h. IgG-targeted particles do not bind and internalize into the cells.

f. In Vitro Cytotoxity

Figure 14:
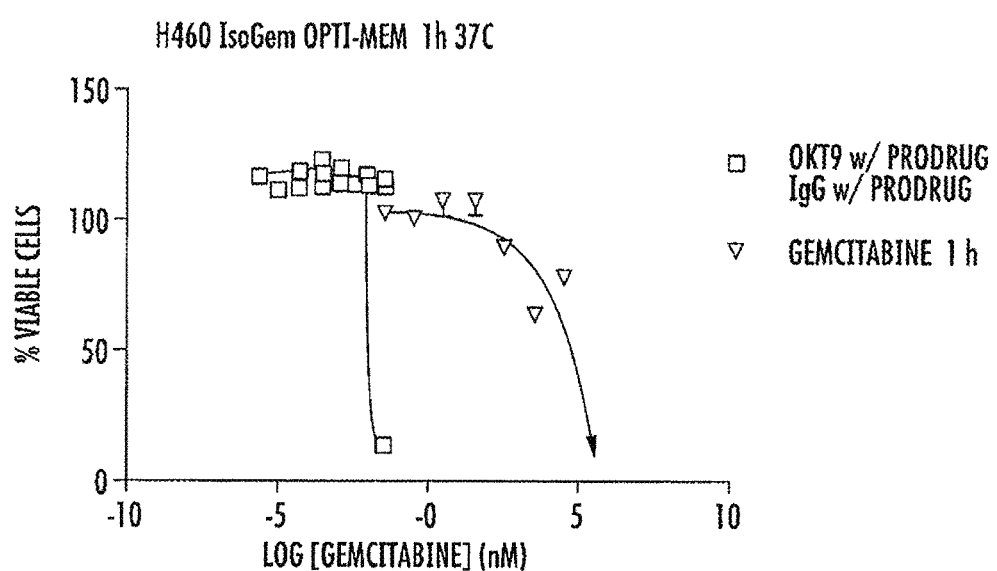
FIG. 14 depicts the cytotoxicity profiles of H460 cells treated with targeted particles containing prodrug. OKT9-targeted particles exhibit enhanced and selective cytotoxicity over free gemcitabine and IgG-targeted particles because of its specific targeting ligands and incorporation of an ABS prodrug.

Targeted particles containing the prodrug were incubated with H460 cells for 1 h at 37° C. to facilitate selective binding of the particles to the TfR. Unbound particles were then removed, and the cells were allowed to incubate at 37° C. for the remainder of 72 h, after which cytotoxicity profiles of cells treated with particles were analyzed with a luminescence assay. OKT9-targeted particles exhibited enhanced cytotoxicity relative to free gemcitabine (FIG. 14). They also exhibited specific cytotoxicity compared to IgG-targeted particles due to the selective TfR targeting of the particles for improved internalization and consequent pro-drug degradation for drug release.

The following references are incorporate herein by reference in their entirety: Reversible hydrophobic modification of drugs for improved delivery to cells, Monahan, Sean D.; Subbotin, Vladimir; Neal, Zane C.; Budker, Vladimir G.; Budker, Tatyana, U.S. Pat. Appl. Publ. (2009), US 20090074885 A1 filed 2009 03 19; Targeted drug delivery by labile hydrophobic modification of drugs, Monahan, Sean D.; Budker, Vladimir G.; Neal, Zane C.; Subbotin, Vladimir, U.S. Pat. Appl. Publ. (2005), US 20050054612 A1 filed 2005 03 10; Protein and peptide delivery to mammalian cells in vitro, Monahan, Sean D.; Budker, Vladimir G.; Ekena, Kirk; Nader, Lisa, U.S. Pat. Appl. Publ. (2004), US 20040151766 A1 filed 2004 08 05; J. Med. Chem. 1993, 36, 3087-3097 3087. Catalytic Functionalization of Polymers: A Novel Approach to Site Specific Delivery of Misoprostol to the Stomach, Samuel J. Tremont, Paul W. Collins, William E. Perkins, Rick L. Fenton, Denis Forster, Martin P. McGrath; Grace M. Wagner, Alan F Gasiecki, Robert G. Bianchi, Jacquelyn J. Casler, Cecile M. Ponte, James C. Stolzenbach, Peter H. Jones, Janice K. Gard, and William B. Wise, Monsanto Corporate Research, 800 North Lindbergh Boulevard, St. Louis, Mo., 63167, and Searle Discovery Research, 4901 Searle Parkway, Skokie, Ill. 60077.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The which is claimed:

1. A method for making a particle comprising:
   a. first, covalently linking a monomer and a silyl via an O, N, S, or carboxyl of said monomer to form a silyl functionalized monomer;
   b. second, covalently linking a nucleic acid to said silyl functionalized monomer to form a first nucleic acid-silyl functionalized monomer; and
   c. third, forming a particle from the first nucleic acid-silyl functionalized monomer of step b, wherein the nucleic acid-silyl functionalized monomer has the structure:

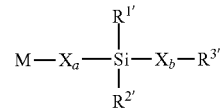

wherein $R^{1'}$ and $R^{2'}$ are independently alkyl;

wherein M is a monomer selected from the group consisting of 2-hydroxyethyl acrylate, 2-hydroxyethyl methacrylate, vinyl pyrrolidone, acrylic acid, ethylene oxide, poly(ethylene oxide), vinyl alcohol, a protein, an amino acid, and a polysaccharide;

wherein $X_a$ and $X_b$ are independently selected from the group consisting of O, NH, S, and a carboxyl; and wherein $R^{3'}$ is a nucleic acid.

2. The method of claim 1, wherein forming the particle comprises molding the first nucleic acid-silyl functionalized monomer in a mold cavity.

3. The method of claim 1, wherein forming the particle further comprises associating a biocompatible polymer with the first nucleic acid-silyl functionalized monomer through a covalent link, physical entanglement, electrostatic association or hydrostatic association.

4. The method of claim 1, further comprising a second nucleic acid-silyl functionalized monomer.

5. The method of claim 4, wherein the second nucleic acid-silyl functionalized monomer comprises the same or different monomer or nucleic acid as the first nucleic acid-silyl functionalized monomer.

6. The method of claim 1, wherein the nucleic acid comprises a ratio of 0.1 mg of nucleic acid to 1 mg of particle.

7. The method of claim 1, wherein the nucleic acid-silyl functionalized monomer comprises between 1 wt % and 50 wt % of the particle.

8. The method of claim 1, wherein the nucleic acid-silyl functionalized monomer comprises between 1 wt % and 40 wt % of of the particle.

9. The method of claim 1, wherein the nucleic acid-silyl functionalized monomer comprises between 2 wt % and 20 wt % of the particle.

10. The method of claim 4, wherein forming the particle comprises molding the nucleic acid-silyl functionalized monomers in a mold cavity.

11. The method of claim 1, wherein the nucleic acid is selected from the group consisting of RNA, siRNA, DNA, and combinations thereof.

12. The method of claim 1, wherein $X_a$ and $X_b$ are both O.

13. The method of claim 1, wherein $R^{1'}$ and $R^{2'}$ are independently selected from the group consisting of methyl, ethyl, n-propyl, iso-propyl, n-butyl, sec-butyl, iso-butyl, and tert-butyl.

14. The method of claim 1, wherein the particle has a release rate of approximately 4 times slower at pH 7.4 relative to a release rate at pH 5.0.

15. The method of claim 1, wherein the particle has a release rate of approximately 50.4 times slower at pH 5.0 and 201 times slower at pH 7.4 relative to a release rate at pH 5.0 wherein $R^{1'}$ and $R^{2'}$ are ethyl.

* * * * *